United States Patent
Masaniello et al.

(10) Patent No.: US 6,813,949 B2
(45) Date of Patent: Nov. 9, 2004

(54) PIPELINE INSPECTION SYSTEM

(75) Inventors: Richard Masaniello, Great Falls, VA (US); Dennis Johnston, Worthington, OH (US); Stephen Christoffersen, Vienna, VA (US); Arthur Turner, Burke, VA (US); John Broussard, Herndon, VA (US); John Kiefner, Worthington, OH (US)

(73) Assignee: Mirant Corporation, Atlanta, GA (US)

( * ) Notice: Subject to any disclaimer, the term of this patent is extended or adjusted under 35 U.S.C. 154(b) by 0 days.

(21) Appl. No.: 10/102,777

(22) Filed: Mar. 21, 2002

(65) Prior Publication Data

US 2004/0031337 A1 Feb. 19, 2004

Related U.S. Application Data

(60) Provisional application No. 60/277,752, filed on Mar. 21, 2001.

(51) Int. Cl.[7] ............................................. G01N 29/04
(52) U.S. Cl. ......................................... 73/623; 73/602
(58) Field of Search .......................... 73/623, 620, 622, 73/599, 600, 602, 865.8, 592, 632, 633

(56) References Cited

U.S. PATENT DOCUMENTS

| | | | | |
|---|---|---|---|---|
| 3,810,384 | A | * | 5/1974 | Evans .......................... 73/611 |
| 4,909,091 | A | * | 3/1990 | Ellmann et al. ........... 73/866.5 |
| 5,127,267 | A | * | 7/1992 | Huebler et al. ............... 73/584 |
| 5,408,883 | A | * | 4/1995 | Clark et al. ................... 73/601 |
| 5,619,423 | A | * | 4/1997 | Scrantz ........................ 702/51 |
| 5,770,800 | A | * | 6/1998 | Jenkins et al. ................ 73/623 |
| 5,907,100 | A | * | 5/1999 | Cook ........................... 73/602 |
| 6,239,593 | B1 | * | 5/2001 | Burkhardt et al. ........... 324/233 |
| 6,339,993 | B1 | * | 1/2002 | Comello et al. ......... 104/138.2 |

* cited by examiner

*Primary Examiner*—Hezron Williams
*Assistant Examiner*—Jacques M. Saint-Surin
(74) *Attorney, Agent, or Firm*—Lava Group Law by Smith & Frohwein, LLC; Gregory Scott Smith

(57) ABSTRACT

The present invention relates generally to a system of addressing pipeline anomalies prior to failure of pipeline integrity, and particularly to a pipeline inspection system integrating a novel serviceability acceptance criteria for pipeline anomalies, specifically wrinkles, with an improved method of correlating ultrasonic test data to actual anomaly characteristics.

9 Claims, 27 Drawing Sheets

Pipeline Wrinkle - 12.75 in - 500 pct. w.t. - l/h = 3 - 270 deg.

Pipeline Wrinkle - 12.75 in - 500 pct. w.t. - l/h = 3 - 270 deg.

Axial Distribution

Pipeline Wrinkle - 12.75 in - 500 pct. w.t. - l/h = 3 - 270 deg.

Circumferential
Distribution

Pipeline Wrinkle - 12.75 in - 500 pct. w.t. - l/h = 3 - 270 deg.

Pipeline Wrinkle - 12.75 in - 500 pct. w.t. - 1/h = 3 - 270 deg.

Pipeline Wrinkle - 12.75 in - 500 pct. w.t. - l/h = 3 - 270 deg.

AISI 1006: Effects of Biaxial Stretching and Cold Rolling

Strain-life plots for two modes of deformation for 1006 steel.

Typical data for total strain versus fatigue life for annealed 4340 steel.

Total strain amplitude vs reversals to failure for Cb (BE), Cb-V (JF) and Cb-V-Si (KF) steels.

Total strain amplitude versus reversals to failure for AISI 50 XF HSLA steel. Upper chart: after balanced biaxial stretching; lower chart: after cold rolling.

Strain-life curves after deformation for AISI 80 DF HSLA steel.

Comparison of Three HSLA Steel Grades, Cb, Cb-V and Cb-V-Si: Strain Life From Constant Amplitude

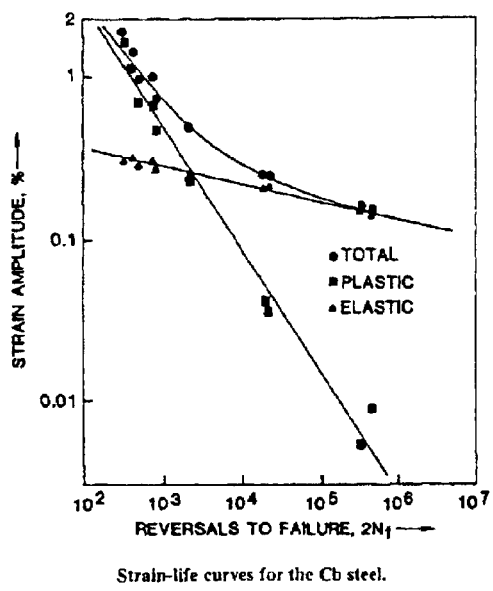

Strain-life curves for the Cb steel.

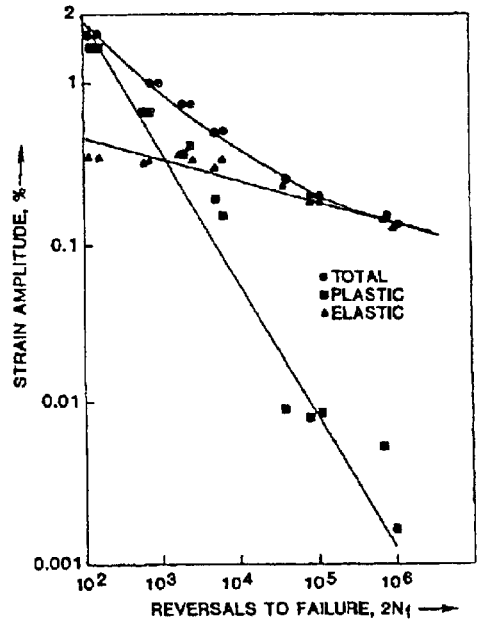

Strain-life curves for the Cb-V steel.

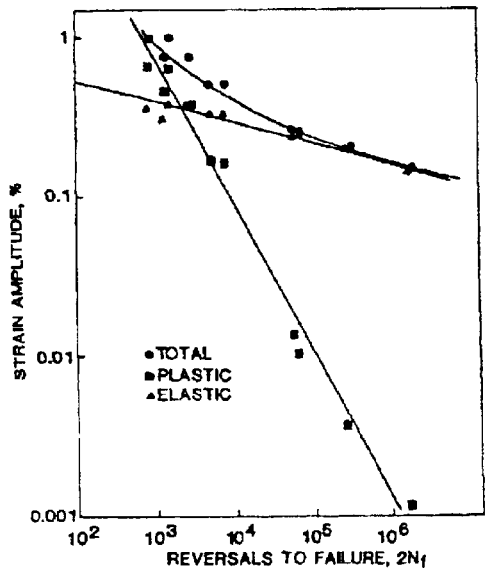

Strain-life curves for the Cb-V-Si steel.

Strain-life curves: Strain-life data from constant-amplitude tests for the three steels are plotted in the three charts here respectively in the form of total strain amplitude versus the number of complete reversals to failure.

FIG. 27

PIPELINE INSPECTION SYSTEM

RELATED US APPLICATION DATA

This application claims priority from U.S. Provisional Application No. 60/277,752 filed Mar. 21, 2001, incorporated herein by reference.

BACKGROUND OF THE INVENTION

1. Field of the Invention

The present invention relates generally to a pipeline safety program, namely a system of addressing pipeline anomalies prior to failure of pipeline integrity, and particularly to a pipeline inspection system integrating a novel serviceability acceptance criteria for pipeline anomalies, specifically wrinkles, with an improved method of correlating ultrasonic test data to actual anomaly characteristics.

2 Description of Related Art

Typically, a pipeline company will have a thorough pipeline safety program that will include a routine for the identification of pipeline defects and review of pipeline integrity. Such a plan should include, but should not be limited to: i) a review of previous internal inspection n report logs by a third party with demonstrated expertise in interpreting inspection report data; ii) excavation of sites identified by this review of the internal inspection report logs for visual examination of anomalies; iii) repairs as necessary; and iv) the use of internal inspection tool surveys and remedial action to the extent needed to address factors in the failure and verify the integrity of the pipeline.

A pipeline safety program can be only as effective as the interpretation of internal inspection reports. If the data recorded by an inspection pig is improperly classified, anomalies that would otherwise require repair may never be identified as serious enough to dig up and inspect. Nearly as problematic, on the other hand, is the great time and energy that may be spent digging up the pipeline searching for anomalies that do not, in fact, warrant inspection.

Proper classification of data recorded by the pig thus is essential for pipeline safety. For example, in one specific case as discussed more fully herein, a 1997 internal inspection of a length of pipeline using sophisticated Ultrasonic Testing (UT) technology identified an anomaly that was misclassified as a pipeline fitting, rather than the true defect—a wrinkle, which wrinkle later led to catastrophic failure of the pipeline. The vast majority of the deformation features examined in the field in this specific case were "ripples" or "wrinkles" that were evident in cold field bends and located on the intradose of the bend. These types of features are characterized by a "sinusoidal" surface waveform with both an inside and outside displacement component. This particular event, and other recent pipeline construction experience (from the late 1980's), has demonstrated that it is often difficult to produce field bends that have smooth contours without the presence of small discontinuities within the bend intrados. Such discontinuities have been referred to generally as "buckles", "ripples", and "wrinkles". Industry research into the structural integrity aspects of wrinkles or buckles in pipelines has been conducted for the past 25 years with the majority conducted since about 1990.

Since the late 1980's, it has become increasing evident that the commonly used field bending "rule-of-thumb"—that pipe could typically tolerate a maximum bend angle of 1.5 degrees per pipe diameter—can no longer be applied universally. It has been found that wrinkles in fact could be formed at smaller bend angles, for example, on the order of 0.75 to 1.0 degree per pipe diameter, and sometimes less.

Bending problems could often be traced to poor field bending practices including the improper setup of bending machines. However, other factors impacted the "bendability" of line pipe, including among others higher yield strengths, increased diameter/thickness ratios, and pipe steel properties, particularly the stress-strain behavior. It also had been found that the heat cycle associated with the application of fusion bonded epoxy coatings also promoted rippling at low bend angles due to alteration of the stress-strain behavior. In some cases, pipe produced to identical specification by different pipe manufacturers could not be bent to the same radius without wrinkling. Even pipe produced by the same manufacturer has exhibited bendability variations during pipeline construction.

Such pipe bending flaws were encountered worldwide, and led to industry research aimed at establishing engineering limits of acceptability for ripples in pipe bends. Thus, not only were there no serviceability acceptance criteria for pipeline wrinkles, but neither was there pipeline inspection data that could be used to develop such an acceptance criterion for wrinkles in pipe bends. Even while pipeline inspection tools became more and more sophisticated, there was no adequate method of correlating that data to represent the true characteristics of the anomaly, which type and severity of anomaly would be found upon repair digs.

Current US Code Requirements for Gas and Liquid Pipelines

For gas pipelines, 49 CFR Part 192 contains requirements for bends in Subpart G titled "General Construction Requirements for Transmission Lines and Mains". With respect to bend contours, Paragraph 192.313 mandates that "a bend must not impair the serviceability of the pipe" and that each bend must have a smooth contour without evidence of buckling, cracks, or other mechanical damage. Also, with some exceptions, longitudinal welds must be near as practical to the neutral axis of the bend. Paragraph 192.315 relates specifically to wrinkle bends in steel pipe. Wrinkle bends are not allowed in pipelines operating at 30% SMYS or higher, and below that, wrinkles must not contain "any sharp kinks". Wrinkles must be separated by at least one pipe diameter and can't have a deflection of more than 1.5 degrees each. The requirements in Chapter 4 of ANSI/ASME B31.8-1999, "Gas Transmission and Distribution Piping Systems" w are similar to those in 49 CFR 192. Paragraph 841.231 provides that bends "shall be free from bucking, cracks, or other evidence of mechanical damage. Like 49 CFR 192, wrinkle bends only are permitted for operation at less than 30% SMYS and must not contain "sharp kinks".

With respect to liquids pipelines, 49 CFR Part 195 contains requirements for pipe bending in Subpart D, "Construction". Bending criteria provided in Paragraph 195.212 prohibit wrinkle bends while "each bend must have a smooth contour and be free from buckling, cracks or any other mechanical damage." Requirements in ANSI/ASME B31.4-1999, "Pipeline Transportation Systems for Liquid Hydrocarbons and Other Liquids" mandate that bends shall be free from buckling, cracks, and mechanical damage. (Paragraphs 404.2, 406.2, and 434.7).

The relevant US code sections therefore do not allow wrinkle bends in pipelines operating at more than 30% SMYS, and prohibit wrinkles anywhere in new pipeline construction.

Wrinkle Acceptance Criteria In Foreign Codes

Several foreign jurisdictions have extensively studied wrinkle problems, including the countries of Australia and Canada that have established acceptance criteria for anomalies like wrinkles. The first acceptance criteria for buckles in Australia was contained in a 1990 amendment to Australian Standard AS 2885-1987, wherein "a buckle shall be deemed to be a defect where it does not blend smoothly with adjoining surfaces or its height is greater than 25% of the nominal thickness and the width of its base is less than eight times its height". Pipeline field bending problems in Australia led to the research that resulted in changes reflected in the current revision of Australian Standard AS 2885.1-1997, "Pipelines-Gas and Liquid Petroleum Part 1: Design and Construction". In this code, a buckle has been defined as "an unacceptable irregularity in the surface of a pipe caused by a compressive stress". The present code also differentiates between "ripples or buckles" formed during cold field bending, and those that may be formed as a result of other factors. In the latter case, the buckle height cannot be greater than 50% of the wall thickness, must blend smoothly with the adjacent pipe, and cannot reduce the internal diameter to less than the approved minimum value.

Section 6.6 of AS 2885.1 covers cold field bends. The bend acceptance limits in this Section include:

Unless approved by the operating authority on the basis of a specific test program, acceptance limits defined in the cold field bending procedure shall be as follows:

The height of any buckle shall not exceed 5% of the peak-to-peak length dimension in the Figures (or wave length).

Ovality shall not exceed 95%. (The minimum ID shall be 95% of the nominal value of the pipe being examined).

Surface strain shall not exceed the lessor of the strain tolerance of the coating being used or 10%.

Appendix J of this code is titled "Procedure Qualification For Cold Field Bends". At the present time, this appendix has also been designated as "informative" which means that it is only for information and guidance. It provides background material needed to guide an operator through a comprehensive bend qualification procedure process.

Another code that contains criteria applicable to the acceptance of wrinkling in pipelines is Canadian Standards Association CSA Z662-1999, "Oil and Gas Pipeline Systems". Pipeline design criteria are provided in Section 4 and Paragraph 4.3.1.1 states that "the designer shall be responsible for determining supplemental local stress design criteria for structural discontinuities". This includes the effects of denting and wrinkling on stress in pipelines.

In one respect the Australian and Canadian codes are similar. Although the Australian code does provide a buckle acceptance criteria, it implies that alternative criteria may be acceptable based on test data. The Canadian code places the responsibility for such analysis on the pipeline designer. In both cases, some level of wrinkle or buckle acceptance is provided for.

Relevant Industry Research

Industry testing has been conducted and includes the initial buckling phase and the post-buckling phase until failure occurred. Some information has been provided as to the conditions needed to promote different forms of buckling plus detailed results. A program was conducted in 1975 and reported in 1976 for Northern Engineering Services to support the design analyses and installation of a high pressure gas transmission pipeline in Canada. The intent was development of a structural design criteria to prevent wrinkling in pipe with and without external sleeve type crack arrestors. Loading due to pressure, temperature, and bending plus the stress state at the crack arrestor ends were considered.

Field bending problems resulting in ripples or wrinkles forming in the compression side led to concern regarding their impact on pipeline integrity. A project was funded by the Australian Pipeline Industry Association beginning in 1990 and completed 1993. This project was aimed at improving the understanding of the field cold bending process and development of acceptance criteria for ripples in bends. This activity resulted in a number of technical publications, and formed the basis for the current wrinkle acceptance criteria in AS 2885.1.

Due to similar concerns regarding field bending difficulties in the US, a project was launched by the Line Pipe Research Supervisory Committee of PRCI. This also included participation in the ongoing APIA project in Australia. Unlike the APIA project, the PRCI effort also included cyclic testing of pipe with ripples. These tests indicated that a large number of cycles (as compared to the number of cycles accumulated in service) would be required to cause failure in a ripple.

Thus, a review of related art indicates that while wrinkles have begun to be addressed in national codes in foreign jurisdictions, it remains apparent that globally the engineering aspects of pipeline wrinkles are little understood. Further, it appears unknown to correlate data gathered from a UT inspection pig to wrinkle deformation. While sophisticated pigging techniques are known, and representatively patented in U.S. Pat. Nos. 6,100,684, 5,864,232, 5,454,276, 5,115,196, 4,747,317, 4,430,613 and 4,072,894, just to identify a few, it still can be seen that a need yet exists for a pipeline inspection system comprising both a novel serviceability acceptance criteria for pipeline wrinkles, and an improved method of correlating ultrasonic test data to actual anomaly characteristics. It is to the provision of such a pipeline inspection system that the present invention is primarily directed.

SUMMARY OF THE INVENTION

Briefly described, in a preferred form, the present invention is an integrity verification program for product pipelines, which program comprises the successful integration of at least three subject areas: pipeline stress analysis, detailed assessment of UT data and disposition of excavated defects uncovered by the UT data. Prior to the present invention, it was unknown whether UT inspection tools could offer any detail regarding pipeline wrinkles.

The present invention arose in relationship with engineering work with a specific pipeline that suffered a leak as a result of a wrinkle that failed. The Piney Point Pipeline is a hot oil pipeline and is comprised of 51.5 miles of steel line pipe insulated with 1 to 2 inches of urethane foam and coated externally with an extruded polyethylene coating. The portion of the pipeline from Piney Point to Ryceville (30 miles) is comprised of 16-inch OD by 0.219-inch w.t. API 5L Grade X42 ERW line pipe. At Ryceville the pipeline is split into two branches, one serving the Morgantown generating facility and one serving the Chalk Point generating facility. Both branches are comprised of 12.75-inch OD by 0.203-inch w.t. API 5L Grade X42 ERW line pipe.

As with most buried pipelines, a hot oil pipeline is generally assumed to be fully restrained. That is, when pressurized with hot oil, it is thought to become stressed as the result of its inability to expand (or contract) due to a change in temperature and due to the "Poisson" effect of internal pressure. Full restraint means that no strain along the axis of the pipeline is permitted to occur. Because the axial stress that results from the restraint can be quite significant, movement of the pipeline may occur in areas where restraint is reduced or lost entirely. Reduction or loss of restraint can occur at bends in the pipeline, in areas of very weak soils, and in the vicinity of points where the pipeline comes above ground. Some movement is tolerable as long as the coating is not damaged by the movement and as long as the movement does not cause buckling of the pipeline.

The Piney Point Pipeline is used intermittently. When in use, No. 6 oil at a maximum temperature of 160° F. is pumped, usually but not always, from Piney Point to one or the other of the two generating facilities. The maximum operating pressure level is 400 psig at the discharge of the pumps. Once the delivery of No. 6 oil has been completed, ambient temperature No. 2 oil is pumped back into the pipeline to flush the No. 6 oil out of the system into heated storage tanks. The temperature of the No. 2 oil is believed to never be below 50° F. and maximum operating pressure for pumping No. 2 oil is also set at 400 psig.

The operation described above results in a cycle of longitudinal stress, but one for which the pipeline is presumably designed. However, a Apr. 7, 2000 release ("Swanson Creek" release) occurred at a buckle which, according to the National Transportation Safety Board's metallurgist, ruptured as the result of progressive cracking in stages presumably from repeated cycles of operation. The cause of the buckle has not yet been fully established, but it is possible that its formation was facilitated by loss of restraint in the particular location of the release.

Following the April 7th release, it was ascertained that the presence of the subject buckle was evident on an internal inspection log in terms of an anomalous reading (loss of ultrasonic signal). The internal inspection tool in this case was run for the purpose of detecting corrosion-caused metal loss, and it has limited capability to quantitatively characterize a buckle. The appearance of the buckle as an "anomaly" on the log when it was reassessed after the failure led to investigation for other like and similar anomalies at other locations. Though no anomaly exactly like the one representing the subject buckle was found, numerous smaller loss-of-signal anomalies were discovered. Upon excavation of representative samples, the anomalies turned out to be wrinkles in the pipe. Though none of the wrinkles was anywhere near as severe as the subject buckle, their existence suggests the need to assess their significance.

It appears that many of the other anomalies corresponded to the type of diamond-shaped wrinkles that can occur when a piece of pipe is subjected to excessively localized deflection during a cold field-bending procedure. It is speculated that because the pipe was cold bent with the urethane foam already on the pipe, the bending contractor was unable to notice that some of the bends were wrinkled. Therefore, whereas the wrinkled bends might have been rejected if noticed, a number of them were installed in the pipeline. The number of locations of such potential wrinkles is large, and it is desirable not to have to address each and every one in terms of remedial measures. It has been established over the past 10 years that minor wrinkles do not pose a significant threat to the integrity of a pipeline.

The analyses described below address the following topics.
Design of the pipeline as per ASME B331.4
Restraint, soil friction, soil passive resistance
Buckling resistance of straight, buried pipe
Propensity of elastically curved pipe to become wrinkled in service
Forces and displacements at bends
Cyclic life of wrinkled pipe.

Several digs were examined to prepare a comprehensive inspection data verification effort in order to provide a clear understanding of the UT tool capabilities. The excavations reliably establishes repeatable relationships between pipe surface deformation patterns (ripples/wrinkles) and UT image information. Considerable knowledge was gained as the result of these efforts that can allow pipeline assessments to be made confidently after inspection by a UT tool, rather than conducting a deformation tool inspection.

Specific field excavation sites were selected from the population of UT "feature" types for the purpose of providing a qualitative understanding of how the UT image type and degree of severity are related dimensionally to the physical shape/condition of the pipe surface. The field data/measurements obtained also allowed direct assessment relative to originally submitted accept/reject criteria for wrinkles.

The vast majority of the deformation features examined in the field were "ripples" or "wrinkles" that were evident in cold field bends and located on the intradose of the bend. These features are characterized by a "sinusoidal" surface waveform with both an inside and outside displacement component. An acceptance/rejection criterion initially was specifically established for these inspections based on the Australian Code and approved by DOT. This original (industry-based) ripple/wrinkle rejection criteria for new pipe was a surface "wave" height greater than 1.5 t (t=wall thickness) and a wave "Aspect Ratio" of less than 12 (aspect ratio=wave length/wave height).

From the detailed analysis of these excavations and the UT data, localized stress data was investigated. The localized stress analyses for various potential wrinkle geometries has led to the conclusion that wrinkles that are less than 180° circumferential arc and have an aspect ratio greater than 7.5 are fit for continued service and need not be repair.

Extensive finite element analyses (FEA) of wrinkle geometries have identified three key characteristics for a wrinkle that control stress levels:
Circumferential Extent;
Wrinkle Aspect Ratio (wrinkle axial extent divided by peak to peak height); and
Wrinkle Profile.

The FEA analysis concludes that a wrinkle is unacceptable if its circumferential extent exceeds 180° or if its aspect ratio (wavelength divided by height) is less than 7.5. Wrinkles with smaller aspect ratios and larger circumferential extents could accentuate with repeated cycling and produce cracks that could extend by a low cycle fatigue propagation mechanism during thermal cycles. The presently proposed acceptance criteria is to allow wrinkles with an aspect ratio of 7.5 or greater and a circumferential extent of 180° or less. These criteria are shown by analysis to conservatively assure that wrinkles left in service are geometrically stable and have adequate fatigue lives, and are thus fit for continued service.

A detailed assessment of UT inspection data with respect to wrinkles was performed in an attempt to understand and characterize the types of UT signals associated with such features. The following can be concluded from this particular initiative:
UT inspection data provides adequate information to quantify the circumferential extent and wave form of wrinkle;

There is a good correlation between circumferential extent of wrinkles and aspect ratio for the features that have been investigated by excavations. Thus, the UT data has provided a sufficient basis for selecting and excavating the features that are a potential structural integrity concern; and There is a very good correlation between the actual field circumferential extent measurements and the UT inspection data associated with the wrinkles excavated and assessed.

The present invention further comprises several types of repair methods, in addition to pipe replacements, including steel reinforcement sleeves (Type B), Composite Sleeves (Clock Spring and Armour Plate), and the PII Epoxy-filled sleeve repair (ESR). The PII ESR is the preferably repair method since most of the locations that contain wrinkles are in proximity to relatively minor bends. These minor bends provide difficulty for a conventional steel reinforcement sleeve installation because they prevent the good fit that is required for effective sleeve performance. Further, the composite sleeves would not provide adequate resistance to axial load introduced by the thermal cycles. Therefore, the best repair option, other than replacing the affected section of pipe, is the PII ESR.

The present invention further comprises an acceptance criteria for pipeline wrinkles. In order to determine the acceptability of local wrinkle deformations in pipe bends, stress analyses were performed using the ANSYS finite element program. A series of finite element models for varying local wrinkle deformation geometries were analyzed using both elastic and elastic-plastic material properties. The wrinkle geometry parameters that were varied include aspect ratio (wrinkle axial length divided by the height), circumferential extent, and maximum height. A model of the Swanson Creek failure wrinkle geometry was also analyzed. The results of these analyses show that:

Elastic peak stress and reversing plastic strain increase with decreasing wrinkle aspect ratio and increasing circumferential extent.

For a given aspect ratio, elastic peak stress and reversing plastic strain decrease with increasing wrinkle height.

The elastic peak stress and reversing plastic strain for the Swanson Creek failure wrinkle geometry are significantly higher than other wrinkle geometries measured during investigative digs.

The investigation of the pipe failure at Swanson Creek identified the failure mechanism as being crack initiation by fatigue with the final rupture occurring by a ductile tearing mechanism. Therefore, it is reasonable to base acceptance criteria for existing wrinkles in the Piney Point pipeline on the remaining fatigue life above the estimated 150 operation cycles experienced to date. Two methods were used to assess the remaining fatigue life for the various wrinkle geometries investigated:

Fatigue Life Based on Experimental Data

Experimental fatigue data showing reversals to failure versus reversing plastic strain in laboratory tests of steels similar to the pipeline's API 5L Grade X42 steel were compared to the reversing plastic strain in the wrinkle calculated by finite element analysis.

Based on the experimental fatigue data, all wrinkles with aspect ratios of 7.5 or greater and circumferential extents of 180° or less have reversing plastic strain values that would result in failure after approximately 2,500 cycles. Additionally, the wrinkle geometry for the Swanson Creek failure was calculated to have reversing plastic strain that would result in failure after approximately 200 cycles. These results demonstrate that the wrinkles that meet the acceptance criteria have large margins on their remaining fatigue lives.

ASME Boiler and Pressure Vessel Code Design Fatigue Life

Section III of the ASME Boiler and Pressure Vessel Code provides rules for determining the design fatigue life of a component based on the alternating stress intensity from an elastic analysis. Finite element analysis was used to calculate the maximum alternating elastic stress intensity for the cases examined.

The results of these calculations show that all wrinkles with aspect ratios of 7.5 or greater and circumferential extents of 180° or less have design fatigue lives greater than the 150 cycles currently experienced, signifying that they are acceptable for immediate return to service. Additionally, the wrinkle geometry for the Swanson Creek failure was found to have a design fatigue life 40% lower than 150 cycles experienced.

The methods of fatigue life assessment detailed above show that:

Wrinkles with aspect ratios of 7.5 or greater and circumferential extents of 180° or less are acceptable for immediate return to service.

Wrinkles with an aspect ratio of 7.5 and a circumferential extent of 180° have expected fatigue lives ten times greater than the Swanson Creek failure wrinkle geometry, based on experimental fatigue data.

Thus, an object of the invention is to provide an improved pipeline inspection system. These and other objects, features, and advantages of the present invention will be more apparent upon reading the following specification in conjunction with the accompanying drawings.

BRIEF DESCRIPTION OF THE DRAWINGS

FIGS. 1–27 depict preferred embodiments of the present invention.

DETAILED DESCRIPTION OF PREFERRED EMBODIMENTS

Figure 1:
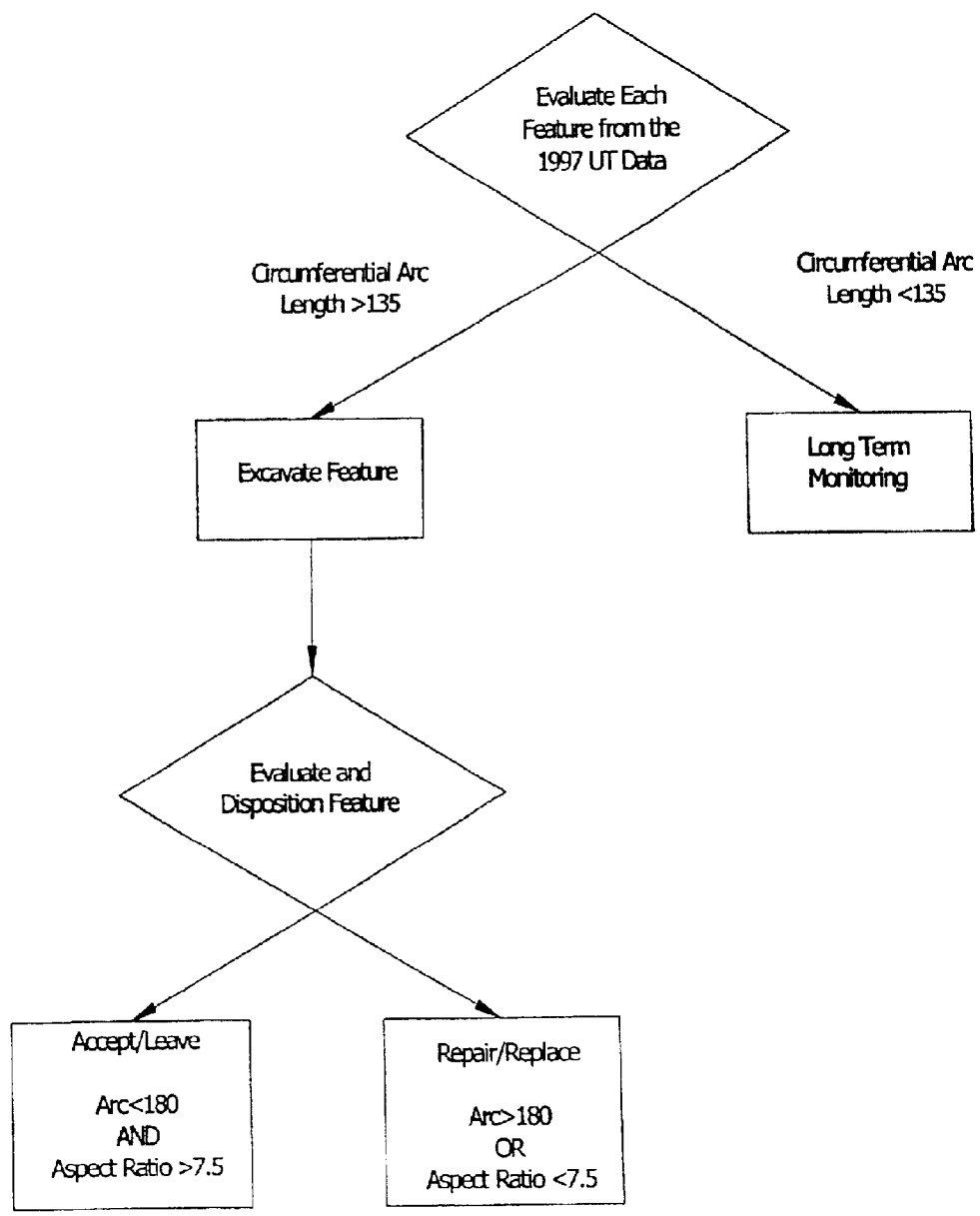

The present invention comprises in part a system of excavation for a pipeline integrity routine whereby any wrinkle with a circumferential extent greater than 135°, as determined by a UT inspection tool, will be excavated and assessed. Features with a circumferential extent less than 135°, as determined by the UT inspection tool, will not be excavated. The 135° circumferential extent limit is quite conservative based on FEA analyses, which show acceptable fatigue lives for wrinkle features with a circumferential extent of up to 180° provided the aspect ratio is 7.5 or greater. This novel excavation criterion provides an adequate safety margin to account for any uncertainty in the UT signal characterization and correlation of the wrinkle's circumferential extent to other important parameters (e.g., aspect ratio) associated with wrinkle geometry. An overview of this system of excavation utilizing evaluated UT data and related field features is shown in FIG. 1.

Prior criteria required a repair for any wrinkle where the peak-to-valley amplitude exceeded 1.5 times the wall thickness and where the aspect ratio was less than 12. The present design analyses demonstrate that wrinkles with aspect ratios as high as 7.5 are acceptable for continued service under conservative stresses and pipe displacements, provided that the circumferential extent is limited to 180° or less. Consistent with ASME and other industries where code and the general body of experience data do not result in establishment of standards, setting a standard through design analysis as proposed by the present invention is appropriate.

The present invention further comprises a correlation system between field inspections and UT data features to enable smart selection of pipeline locations requiring attention. An extensive and detailed assessments of UT image pattern data and the corresponding physical field measurements involving a selected population of distinct UT "features" led to the present correlation system. This comprehensive inspection data verification effort provided a clear understanding of the UT tool capabilities and reliably establishes repeatable relationships between pipe surface deformation patterns (ripples/wrinkles) and UT image information.

In the review of the UT pig inspection logs for the entire pipeline, the complete UT data set was sorted in a manner that categorized all physical deformation "features" into six (6) distinct pattern types (U, A, B, C, D and E) based on the geometric shape of the UT signal and sequenced by the "seriousness" of the pattern type ranked from U to E. These were in turn sub-sorted by degree of signal intensity from the most intense to the least intense (0, 1, 2, and 3).

With UT deformation pattern types formally categorized, excavation and inspection of the four (4) most severe (worst) features plus three (3) additional features on each of the pipeline segments were conducted. References to "Swanson Creek" refer to an anomaly originally evaluated as a field bend, but in fact was a wrinkle that burst. The primary objective of this UT signal classification and site excavation program was to correlate UT image pattern data with the physical condition of the pipe to gain a better understanding of the nature and extent of the physical features and the interpretation capabilities of the UT technology.

Field Inspection Methodology:

Specific field excavation sites were selected from the population of UT "feature" types. Examinations of the pipe surface consisted of: Pi tape/micrometer measurements of the pipe diameter, mechanical measurements of the surface contour (wave form), Wet Fluorescent Magnetic Particle Examination (WFMT) examination of the outside pipe surface (OD) for cracking; and Time Of Flight Diffraction (TOFD) for detection of cracks on the inside pipe surface (ID). A set of specific Defect Assessment Criteria was used to disposition each of the features examined as a "pass" or "fail".

Mechanical measurement of the pipe surface contour was made using both traditional measurement techniques and a state-of-the-art 3-D, portable computer Coordinate Measuring Machine (CMMFARO Arm). The FARO Arm data can be viewed to show the deformation feature in any orientation and has been used to validate the close correlation of UT data to actual feature geometry.

Field Inspection Results:

A general summary of the field inspection findings for the features examined, representing the worst features in the pipeline, is provided as follows:

Extensive field NDE examinations confirm no cracks—Specialized, state-of-the-art, field UT examinations were conducted of the features. These results were obtained by leading NDE industry experts. The results were that there were no cracks were found in either the base metal or seam welds in or around wrinkles.

UT image characterizations are an indication of deformation significance—The qualitative designations of UT pattern types (designators U-E) developed from review/interpretation of the UT logs directly correlates to the significance found by direct field assessments. The methodology of using UT data to assess and reasonably characterize the severity of wrinkles or surface damage has been demonstrated to be valid. The data identifies even the most minor pipe surface deformations as evidenced by examinations of patterns on acceptable field bends that had barely visible surface ripples. No minor surface deformations were found that had not been revealed by the UT data. The type-C, type-D, and type-E features examined in the field were confirmed to be much less significant (severe) than the type-U, type-A and type-B features consistent with the ranked UT data. All of these lower level features passed the original acceptance criteria.

Figure 2:
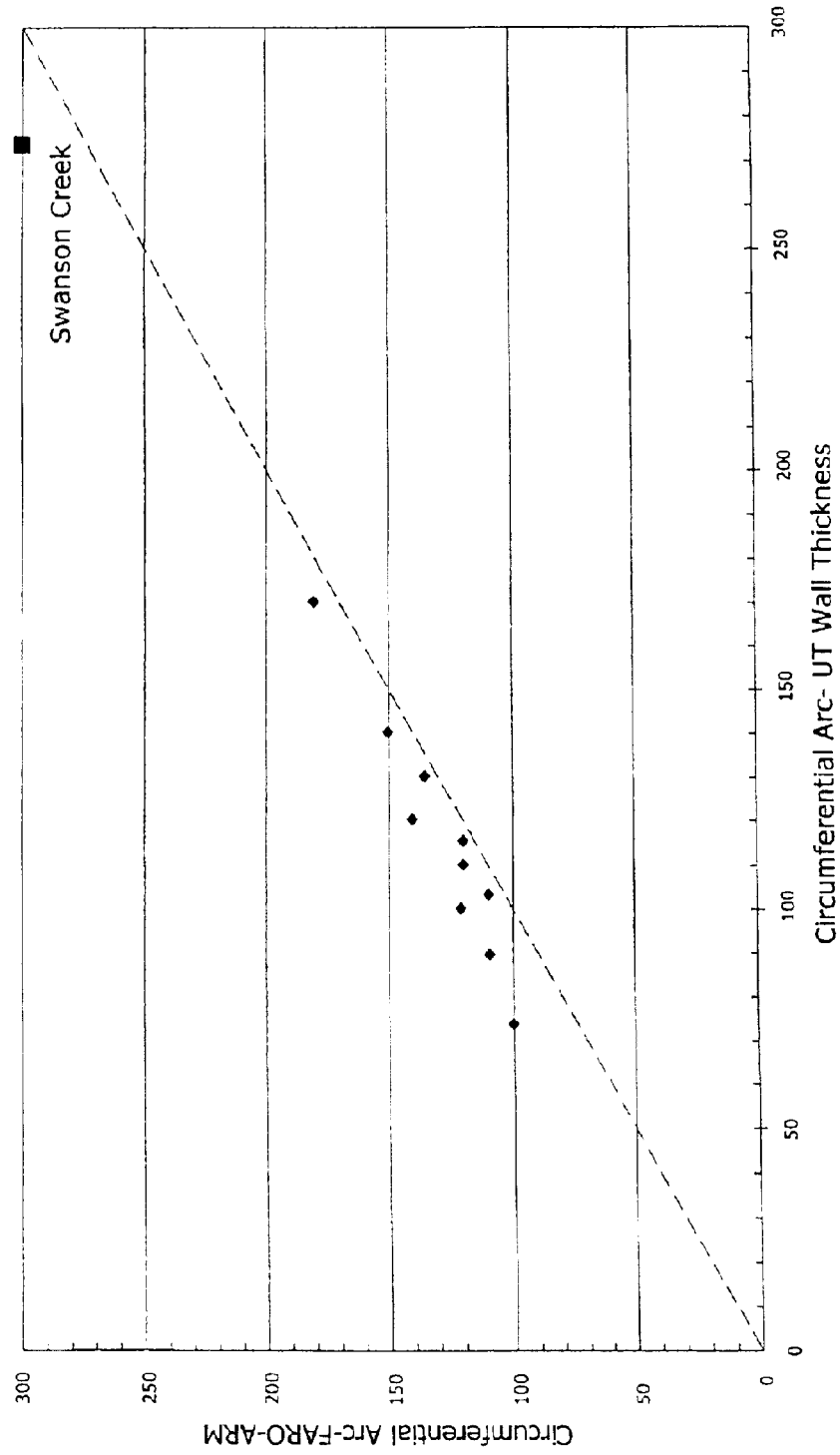
Figure 3:
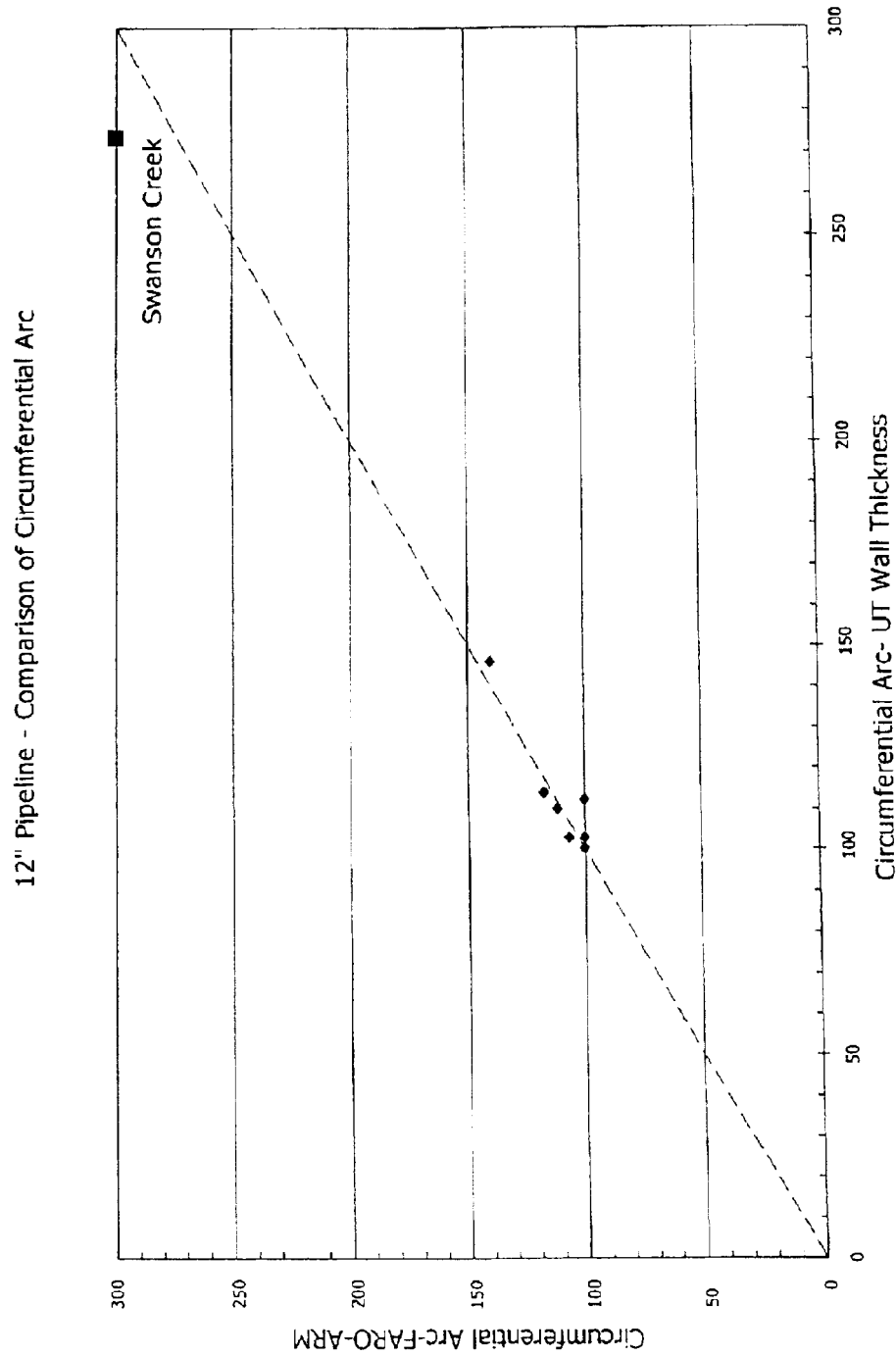

UT data correlates with physical data—The degree of circumferential arc impact as measured in the UT log correlates directly with field arc measurements for wrinkles as shown in FIGS. 2 and 3. UT arc data, therefore, provides a valid means to accurately predict the field arc and length and to reasonably predict the aspect ratio.

No other features exhibited deformation as extensive as found at Swanson Creek—Field examinations of the four (4) most severe UT image patterns and the other severe patterns that failed the original wrinkle acceptance criteria were less extensive than Swanson Creek. There were no other features like the one that failed at Swanson's Creek (Aspect Ratio of 3.25). The rapture site is shown as an "outlier" in the data set as depicted in FIGS. 2 and 3. Unlike any of the others examined, the Swanson Creek wrinkle had a distinctively outside-only (bulge) waveform that had no sinusoidal element.

UT detection sensitivity—The UT data identifies even the most minor of pipe surface deformations as evidenced by examinations of patterns for acceptable field bends that have barely visible or tactically detectable surface ripples. No minor surface deformations were found that had not been revealed in the UT data.

UT Data is effective for locating the worst deformation (wrinkles)—Field measurement correlation with the UT image patterns that include the worst features confirm the ability to identify and locate the most severe damage areas on the pipeline.

UT Data-Based Repair Acceptance Criteria—The conventional wrinkle rejection criteria (>1.5 t and aspect ratio<12) was based on industry testing analysis for new pipe and intended for broad applicability to the fall range of pipeline sizes and wall thickness. Design-based criteria have been specifically developed for 16" pipeline. These criteria indicate a wrinkle is not acceptable when its aspect ratio is less that 7.5 or its circumferential extent is greater than 180°.

Figure 4:
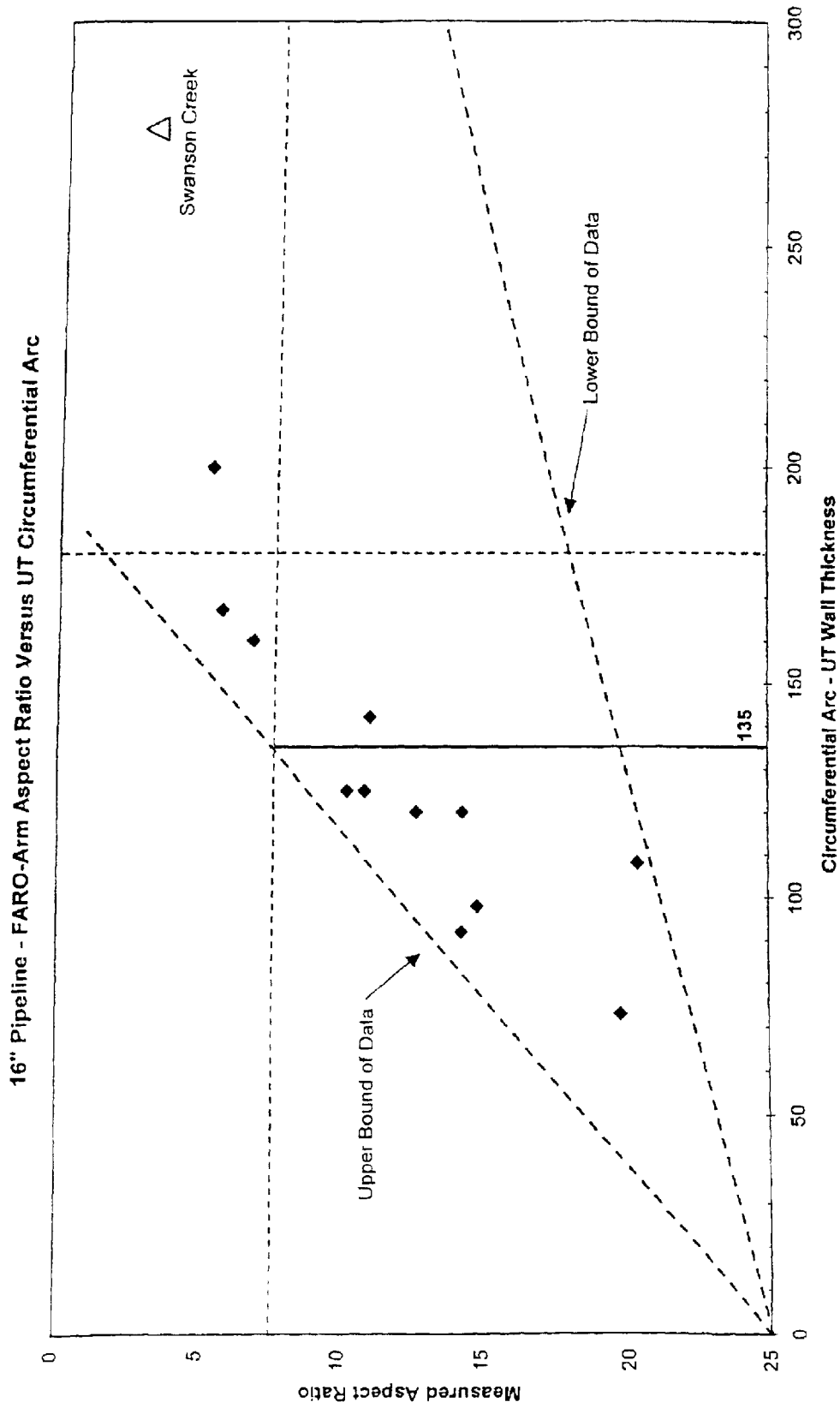
Figure 5:
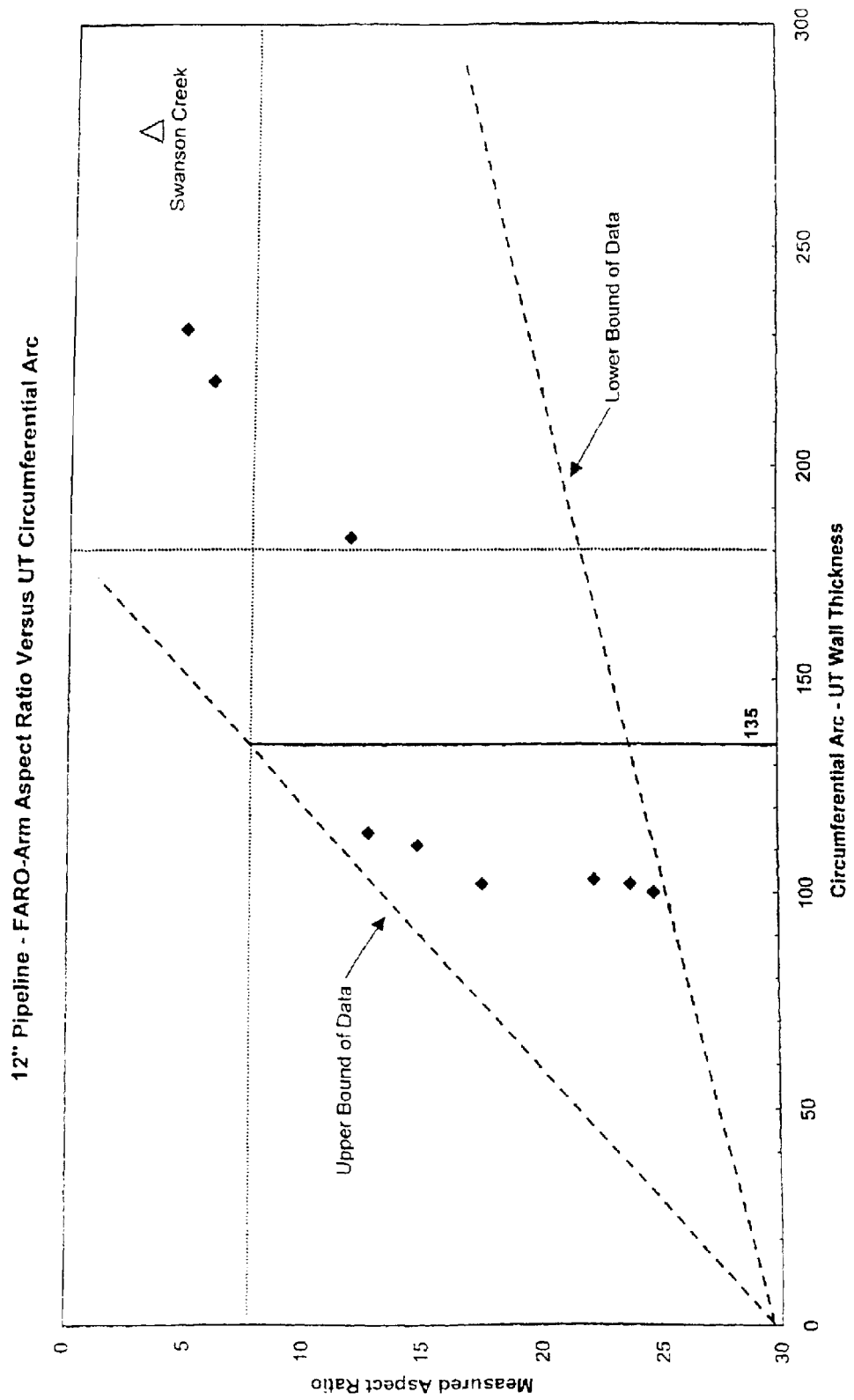

UT Data-Based Wrinkle Excavation Criterion—The UT data shown in FIGS. 4 and 5 demonstrate that features with a circumferential extent of 135° or less (as identified by the UT inspection tool) will have an aspect ratio of greater than 7.5.

UT Data-Based Dent Identification—The UT tool data may be used to distinguish dents from wrinkles.

As demonstrated above, a distinctive relationship exists between the UT circumferential arc and the magnitude of the ripple/wrinkle waveform; this allowed selection of the worst features in each image category type (U, A, B, C, D, E) for field inspection.

The present invention further comprises an analysis based on classical engineering-mechanics principles of the design and wrinkling potential. The purpose of this analysis is to determine the extent of the risk, if any, that other existing wrinkles in the pipeline could cause a failure in the future.

Design Of The Pipeline As Per ASME B31.4

ASME B31.4, 1998 Edition, Paragraph 402.3.2(c) provides for an allowable equivalent tensile stress not to exceed 90 percent of SMYS (specified minimum yield strength) of the pipe material for expansion stresses in a restrained pipeline. For Grade X42, SMYS is 42,000 psi so $S_E$, the equivalent stress, may not exceed 0.9 times 42,000 or 37,800 psi.

As per Paragraph 419.6.4(b), the net longitudinal compressive stress due to temperature rise and internal pressure $S_L$ is $$S_L = E\alpha(T_2-T_1) - \nu S_h \quad (1)$$

$$S_h = \frac{PD}{2t} \quad (2)$$

where $S_L$=Longitudinal compressive stress, psi $S_h$=Hoop stress due to fluid pressure, psi $S_E$=The equivalent stress that is used to check against failure (yielding) due to the maximum shear stress reaching one-half the uniaxial tensile yield strength of the material $T_1$=Temperature at time of installation, °F.

$T_2$=Maximum operating temperature, °F.

E=Modulus of elasticity of steel, psi $\alpha$=Linear coefficient of thermal expansion in/in/°F.

$\nu$=Poisson's ratio

Relevant data for the Piney Point Pipeline are

P=normal operating pressure, 400 psig $T_1$=50° F.

$T_2$=160° F.

E=30×10⁶ psi $\alpha$=6.5×10⁻⁶ psi $\nu$=0.3

D=Outside diameter of pipe, inch t=Wall thickness of pipe, inch

Therefore, for the 12.75-inch OD by 0.203-inch w.t. pipe $S_h$=PD/2t=400(12.75)/[(2)(0.203)]=12,562 psi $S_L$=30(10⁶)(6.5)(10⁻¹)(160−50)−0.3(12,562)=21,450−3,769=17,681 psi $S_{E12}$=$S_h$−$S_L$=12,562−(−17,681)=30,243 psi For the 16-inch OD by 0.219-inch w.t. pipe $S_h$=PD/2t=400(16)/[(2)(0.219)]=14,612 psi $S_L$=30(10⁶)(6.5)(10⁻¹)(160−50)−0.3 (14,612)=21,450−4,384=17,066 psi $S_{E16}$=$S_h$−$S_L$=14,612−(−17,066)=31,678 psi In both cases, the equivalent stress is less than the allowable stress: 37,800 psi or 90 percent of SMYS.

The straight pipe design of the pipeline (both sizes of pipe) is adequate. In fact, the 12.75-inch OD pipe would still be in compliance if the temperature differential were 148° F. This is found by letting the allowable $S_L$=37,800−$S_h$ where $S_h$ is 12,562. Therefore, $S_L$=25,233 psi.

$$\Delta T_{12} = \frac{S_L - \nu S_h}{E\alpha} \quad (3)$$

$$= \frac{25,2338) + 0.3(12,562}{(30)(10^6)(6.5)(10^{-6})}$$

$$= \frac{29,007}{195}$$

$$= 148.78° \text{ F.}$$

Similarly, for the 16-inch pipe $S_L$=37,800−14,612=23,188 psi $$\Delta T_{16} = \frac{23,188 + 0.3(14,612)}{(30)(10^6)(6.5)(10^{-6})}$$

$$= \frac{27,572}{195}$$

$$= 141.4° \text{ F.}$$

Restraint Soil Friction, Soil Passive Resistance

The previously discussed ASME B31.4 calculations are based on the assumption that the pipeline is fully restrained from any axial movement by the soil in which it is buried. Various authors have addressed the conditions that determine when full restraint exists and what happens when fall restraint changes to partial restraint or no restraint at anchors, bends, or transitions to above-ground pipe.

Restraint

Restraint of axial movement may be effected by burial in soil or by artificial means (i.e., the building of anchoring foundations). The thrust force on a fully restrained (unyielding) anchor foundation arises from three sources, restrained axial thermal expansion or contraction, restrained axial tension from the Poisson effect of hoop stress, and internal pressure acting on the end of the pipe at or beyond the anchor foundation.

$$F = A[E\alpha(T_2-T_1)-\nu S_h+PD/4t] = A[E\alpha(T_2-T_1)-0.3S_h+0.5S_h] = A[E\alpha(T_2-T_1)+0.2S_h] \quad (4)$$

where

A=The cross-sectional area of the pipe material, $\pi Dt$, in², and the other parameters are the same as described previously.

For the 12.75-inch OD pipe with P=400 psig, $T_2$=160° F. and $T_1$=50° F.

$$F_{12} = \pi(12.75)(0.203)\left[30(10^6)(6.5)(10^{-6})(110) + 0.2(400)(12.75/2)\left(\frac{1}{0.203}\right)\right]$$

$$= 194,843 \text{ lb.}$$

Similarly, $$F_{16} = \pi(16)(0.219)\left[30(10^6)(6.5)(10^{-6})(110) + 0.2(400)(16/2)\left(\frac{1}{0.219}\right)\right]$$

$$= 268,295 \text{ lb.}$$

Soil Friction

Long buried pipelines are fully restrained by soil friction. Near points where a pipeline emerges from below ground, the restraining effect of soil friction ranges from fall restraint to no restraint. Usually, it is assumed that the restraint varies linearly from full restraint to zero over a pipeline axial distance called the "active" length or the "transition" length. The active length depends on the coefficient of friction between the pipe (or its coating) and the soil, the diameter of the pipe, the depth of cover over the pipe, and the unit weight of the soil. The authors of the various references, as listed in Appendix A, present data and/or opinions concerning soil friction coefficients and methods for calculating the friction force on the pipeline. The relevant parameters are summarized in Table 1. As one can see, values of parameters and equations for their calculation vary considerably for several reasons. First, any measured value would have to depend on the type of soil, its degree of compaction, and its moisture content at the time of measurement. Second, direct measurements of forces using strain gages as was done in Reference 7 clearly depended on soil types and moisture contents. Third, assumptions clearly varied from researcher to researcher. Fourth, soils tend to be inherently non-homogeneous, and their behavior is often difficult to characterize. Certainly, they are not linear-elastic materials even though assumptions of soil linear elasticity are often made in order to calculate the behavior of a buried pipeline.

Certain factors and forces in Table 1 are reasonably consistent. One is the thrust force.

The thrust force against an unyielding anchor is $F=A(S_L+S_h/2)$, the same as Equation 4 described previously. Most of the references utilized this equation. References 5 and 6 contained slightly different equations, but it was not clear what the authors intended. Another factor calculated consistently among the various references is the active length of pipeline over which full restraint develops near a free end. The active length is defined as F (Equation 4) divided by the friction force "f" in pounds per foot. For the purposes of this report, we will also define, L, the active length as $$L=F/f \qquad (5)$$

A third quantity calculated consistently is the axial deflection of the pipe at a free-end. This deflection is assumed to be zero at the "virtual anchor point" and to increase linearly with distance from the virtual anchor point to the free end (a total distance equal to L). We will henceforth use this approach to calculate the movement, y, at a free end.

$$y=6F^2/AEf, \text{ inches} \qquad (6)$$

The area of greatest disagreement among the various references (4–16) was that of how to calculate the friction force. In principle, all of the references agreed that the axial friction force opposing axial movement in the soil is equal to the external force of the soil pressing on the pipe or "normal" force times the coefficient of friction. There was no consistent definition of the normal force, and the values of coefficients of friction varied over a wide range as shown in Table 1. One of the three variations of friction force definitions is that shown in References 4 and 8, namely $$f=\mu(\gamma DH/6+W_p), \text{ lb/ft} \qquad (7)$$

where $\mu$=is the coefficient of friction $\gamma$=is the unit weight of the soil, lb/ft$^3$ D=is the outside diameter of the pipe, inches H=is the depth of soil cover to the top of the pipe, ft (Note: H as used here is not necessarily the same as H as used in some of the references; however, our H is equivalent to the depth of cover to the top of the pipe.)

$W_p$=is the weight of the pipe and its contents, lb/ft.

This definition embodies the assumption that the normal force consists of the weight of the soil above the pipe acting on top of the pipe plus the reaction to the weight of the soil and the weight of the pipe and its contents acting on the bottom of the pipe. Also, an inherent assumption is that the soil is cohesionless. The reasonableness of this approach stems from its similarity to the manner in which the sliding friction force is calculated for an object resting on a horizontal surface. We use this definition of f in this analysis because it makes sense and gives mid-range values in comparison to the other methods as shown in Table 2. The format shown in Reference 6 is a slight variation on Equation 7. The term "B" means the width of the ditch in the same context as used in the "Marston" formula and the coefficient 0.85 is based on a H/B ratio of 1.0. Basically, it is a "weight-of-the-overburden" approach. Because it uses B instead of f, we believe it is better to use Equation 7.

A second definition of friction force is that shown in References 5 and 14, namely $$f=\mu(\gamma H\pi D/12), \text{ lb/ft} \qquad (8)$$

where

H and $\gamma$ are defined for Equation 7 above and $\pi$D is the surface area of the pipe per unit length (inches$^2$/ft).

This definition appears to be equivalent to assuming that the normal force is the "hydrostatic pressure" of the soil acting over the entire surface area of the pipe. As in the Equation 7 definition, the soil is assumed to be cohesionless. The format shown in Reference 13 appears to be a slight variation of Equation 8 in which the coefficient of friction, $\mu$, is equal to the tangent of the soil-pipe friction angle$^i$, and a coefficient, $K_{av}$, is used to represent the effective earth overburden weight. The effective weight can be influenced by "arching" if the soil is cohesive or has an inherent angle of repose. In this case, it is not 100 percent effective. The author of Reference 13 suggests using $K_{av}$=0.75. The soil-pipe friction angle is the angle between vertical (direction of gravity) and the line perpendicular to the slope of the pipeline at which the pipe would slide due to its own weight. The author suggests that a minimum angle of 20 degrees could be expected so that minimum value of $\mu$ expected is tan 20 degrees or 0.36.

The third definition of friction force appears in References 9 and 10, namely $$f=80(D/12)^2 \text{ lb/ft.} \qquad (9)$$

As shown in Table 2, this definition of f yields the lowest predicted values. Again, we believe it is better to use Equation 7. A vague reference to "tests" suggests that this definition was determined by experiments. As a point of interest, the experiments described in Reference 7 resulted in measured values of friction force ranging from 245 lb/ft to 5,614 lb/ft for a 20-inch diameter pipeline. Equation 9 predicts 222 lb/ft. Obviously, the experimental conditions depicted in Reference 7 varied considerably. The description of the tests is not sufficient for the reader to understand the large variations. It is suspected that the readings were taken over short periods of time that did not allow the creep behavior of the soils to be effective. Therefore, the extremely high values of friction force likely could not be realized over a long period of time.

At least two attempts have been made to measure coefficients of friction between pipes and soil both with and without coatings on the pipe. These attempts have produced coefficients ranging from 0.33 for bare pipe to as high as 0.91 for pipes with coal-tar enamel coatings. For bare pipe and smooth coatings such as fusion-bonded epoxy or polyethylene tape, it appears that a value of 0.3 is a lower bound. The use of a lower-bound value such as 0.3 will produce conservative estimates of active length and movements of free ends to be used in further analyses herein.

Having settled on using the Equation 7 definition of friction force and a coefficient of friction of 0.3, we then calculated as shown in Table 2 the friction forces, active lengths, and free-end movements of both the 12.75-inch pipe and the 16-inch pipe of the Piney Pont Pipeline.

The results are

|  | 12.75-Inch OD | 16-Inch OD |
| --- | --- | --- |
| Friction force, lb/ft | 260.9 | 332.6 |
| Active length, ft | 746.8 | 806.7 |
| Free-end movement, inches | 3.58 | 3.93 |

Soil Passive Resistance

In order to predict the behavior of the pipe under various circumstances, it is necessary to know or to calculate reasonable estimates of three additional soil parameters or soil-pipe-behavior parameters: uplift resistance, passive lateral resistance, and coefficient of subgrade reaction. In theory, bearing capacity should also be known, but in practice it is reasonable to assume that bearing capacity will always exceed passive lateral resistance. Hence, the latter will give lower-bound values of deformation behavior.

Uplift resistance arises from the weight of the soil overburden and the weight of the pipe and its contents. Uplift resistance keeps a pipeline subjected to axial compressive stress from buckling upward. A simple and conservative estimate of uplift resistance is $$R_u = \gamma HD/12 + W_p, \; lb/ft \tag{10}$$

where $R_u$ the lift resistance in, lb/ft $\gamma, H, D$, and $W_p$ are as defined previously.

Reference 13 gives a variation of uplift resistance that relies not only on the weight of the overburden and the pipeline, but the added weight of the wedges of soil that are defined by the triangles of soil area above the top of the pipe to each side of the overburden immediately above the pipe. This material can be partly effective in providing resistance based on the "angle of repose" of the soil. Reference 13 uses an angle of repose, $\phi$, of 30 degrees that is typical for granular non-cohesive soils. We will instead use Equation 10 because it is more conservative and can be expected to give the minimum level of uplift resistance.

Passive lateral soil resistance serves to prevent sidewise buckling of a pipeline subjected to axial compressive stress and the movement of anchors or bends. It is defined in both Reference 4 and Reference 13 as $$R_p = \frac{\gamma}{2}\left(H + \frac{D}{12}\right)^2 \tan^2\left(45 + \frac{\varphi}{2}\right), \; lb \; ft \tag{11}$$

where $R_p$ = Passive lateral resistance, lb/ft $\gamma, H, D$, and $\phi$ are as defined previously.

Equation 11 is used to calculate passive lateral resistance for both types of pipe in the Piney Point Pipeline as shown in Table 3.

For the purposes of this report, we assume that the soil behaves as a linear-elastic material. This assumption is probably valid only for very low levels of soil stress and is highly a function of the type of soil. It is a necessary simplifying assumption for the simple conceptual analyses contained herein, and it does permit us to make bounding estimates of the behavior of the pipeline. An elastic soil property called the coefficient of subgrade reaction is assumed to exist for the purpose of calculating moments and shears in a beam supported on an elastic foundation. This coefficient can be viewed as a spring constant for the soil. It has units of inches of deflection per pound per inch of load.

Reference 4 defined this coefficient as $$K = \frac{U}{0.015\left(H + \frac{D}{12}\right) \times 144} \tag{12}$$

$$= 0.2315\gamma\left(H + \frac{D}{12}\right)\tan^2\left(45 + \frac{\varphi}{2}\right), \; lb/in^2$$

where

U = is defined by Equation 11

$H, D, \gamma$ and $\phi$ are as defined and previously.

The K values for the Piney Point Pipeline are given in Table 3.

Buckling Condition For Straight Pipe

Axial Buckling Load

The column buckling load for an infinitely long, initially straight buried pipeline on an elastic foundation is given on Page 142 of Reference 17. The load $N_{cr}$ is defined as $$N_{cr} = 2\sqrt{KEI}, \; lb \tag{13}$$

where

K = is the coefficient of subgrade reaction, $lb/in^2$

E and I are defined previously.

The use of this equation to calculate $N_{cr}$ is based on the assumption that the soil offers identical resistance in all directions. While not exactly true, it will be seen that as long as the pipeline is straight, the foundation resistance required to prevent buckling is relatively small. Based on the values of K calculated via Equation 12, we show in Table 3 that the $N_{cr}$ values for the Piney Point Pipeline are

|  | $N_{cr}$, lb | Maximum Axial Load in the Pipe, F, lb |
| --- | --- | --- |
| 12.75-inch OD by 0.203-inch w.t. | 2,644,465 | 194,834 |
| 16-inch OD by 0.219-inch w.t. | 3,987,785 | 268,295 |

The $N_{cr}$ loads required for buckling are roughly fourteen times the maximum axial loads in the pipe segments. Therefore, no axial buckling is to be expected.

Strictly speaking, the resistance to uplift would be expected to govern buckling. This is because the weight of the soil overburden and the weight of the pipe and its contents offer less resistance than the passive lateral resistance of the soil. To show that this upward buckling of the straight pipe is not a reasonable possibility, we first calculate the "Euler" buckling length of the pipe materials. The Euler buckling equation, named for its 18th-century developer, gives the relationship between axial load at elastic buckling and the geometric and elastic properties of a pinned-end column. The Euler buckling solution for critical maximum length for a given applied axial load is $$l = \sqrt{\frac{\pi^2 EI}{F}}, \; inches \tag{14}$$

where

F is the maximum axial load in the pipe and E and I are as defined previously. As shown in Table 3, these lengths are: 12.75-inch OD×0.203-inch w.t. pipe: 501 inches 16-inch OD×0.219-inch w.t. pipe: 623 inches. To show that these lengths are actually characteristic of elastic buckling, we need to calculate the radius of gyration of each pipe ($\bar{r}=\sqrt{I/A}$), and the ($l/\bar{r}$) ratio. As shown in Table 3, the radii of gyration are

| | |
|---|---|
| 12.75-inch OD × 0.203-inch w.t. pipe: | 4.51 inches |
| 16-inch OD × 0.219-inch w.t. pipe | 5.66 inches | and the $l\bar{r}$ values are 111 and 110, respectively. Generally, for $l\bar{r}$ ratios greater than 60, the Euler buckling will be totally an elastic phenomenon.

We can now consider the possibility that a length of pipeline equal to the Euler length would buckle against the uplift resistance of the soil and the weight of the pipe and its contents. On Page 96 of Reference 18, the following equation is given for the buckling of an Euler beam column (pinned ends) on an elastic foundation. The critical level for the single sine wave mode of buckling of such a beam column is $$P_u = \frac{\pi^2 EI}{l^2}\left(1 + \frac{Kl^4}{\pi^4 EI}\right) \quad (15)$$

where

K is the coefficient of subgrade reaction, lb/in$^2$ and E, I, and l are as defined previously. If we assume that K is at least equal to the uplift resistance shown in Table 3 for any incipient buckling deformation, we can calculate an effective $K_u$ equal to $R_u/12$. In that case, $K_u$ for each pipe material becomes

| | |
|---|---|
| 12.75-inch OD by 0.203-inch w.t. | $K_u$ = 39.28 lb/in$^2$ |
| 16-inch OD by 0.219-inch w.t. | $K_u$ = 50.73 lb/in$^2$ |

By Equation 15, we then calculate that $P_{cr}$ for the 12-inch pipe is 1,193,456 lb and for the 16-inch pipe it is 2,260,094 lb. These loads are approximately six and eight times the maximum axial loads in the two pipe segments, respectively.

The above calculations indicate that burial of the Piney Point Pipeline in reasonably stable soil prevents, by a wide margin, initially straight portions of the pipeline from buckling due to temperature change. The fact that no such buckling has been observed in service also indicates that straight pipe buckling is not expected.

Buckling Conditions For Pipe With Initial Elastic Curvature

While straight pipe is clearly not at risk from elastic buckling, we also need to assess the situation with respect to pipe that has initial elastic curvature. The worst case expected would be an elastically formed overbend where the prevention of buckling depends on uplift resistance. For this case, we refer to Pages 30–32 of Reference 18. On the one hand, we learn that a beam column with an initial deformation $$y_o = a\sin\frac{\pi x}{l}$$

has a total deformation of $$y = \frac{a}{1-\beta}\sin\frac{\pi x}{l}, \text{ inches} \quad (16)$$

where

β=is the ratio of axial load to the Euler critical buckling load.

a=is the mid-point (i.e., maximum) deflection of the beam column.

On the other hand, we learn that the single sine-wave deformation of a beam column with a uniform lateral load is equal to $$y = \frac{4ql^4}{\pi^5 EI}\sin\frac{\pi x}{l}\left(\frac{1}{1-\beta}\right), \text{ inches} \quad (17)$$

where q=is the uniform lateral load, lb/in and β, l, E, and I are as defined previously.

By assuming that any portion of the pipeline with an initial elastic overbend curvature according to Equation 16 is equal to the y of Equation 17, we can calculate an "a" value of upward defection that would be exactly offset by the deflection downward caused by a uniform axial load, q for the Euler critical length of each pipe material (via Equation 14). The uniform load q is equal to $W_p/12$ where $W_p$ was defined previously. The corresponding "a" values are 6.53 inches for the 12-inch pipeline and 9.45 inches for the 16-inch pipeline. It is important to note that these deflections are about the maximum possible elastic deflections for the Euler lengths of the pipeline. This can be ascertained from the maximum stress level and maximum deflection in a uniformly loaded simply supported beam, so any sharper overbend would have to be made intentionally.

$$S_S = \frac{ql^2\left(\frac{D}{2}\right)}{8\pi\left(\frac{D}{2}\right)^3 t} \text{ and } y_3 = \frac{5ql^4}{384EI}$$

For the two pipe materials, the values are

| | $S_s$, psi | $y_s$, inches |
|---|---|---|
| 12 inch | 47,550 | 6.5 |
| 16 inch | 55,896 | 9.4 |

These calculations suggest that even with the maximum possible elastically curved overbend, the axial load due to temperature change will not cause upward buckling of the pipeline. Any tendency to buckle upward will be offset by downward deflection from the weight of the soil overburden and the weight of the pipe and its contents.

Forces, Moments, Deformations, And Stresses At Cold Field Bends

For purposes of examining cold field bends, we will assume that the radius of each bend, R, is 18D, the maximum amount of cold field bending permitted by ASME B31.4. For the two materials, these values are

| | | Bend Radius, R | |
|---|---|---|---|
| | Diameter | Inches | Feet |
| 12-inch pipe | 12.75 | 229.5 | 19.125 |
| 16-inch pipe | 16.00 | 288.0 | 24.000 |

According to Reference 12, the radial-force reaction at a bend, $P_s$, is $$P_s = F/R \text{ lb/ft} \quad (18)$$

where

F = is the axial force exerted by the pipeline, lb

R = is the bend radius, feet.

For bends in the Piney Point Pipeline, the radial reactions are

|  | F, lb | R, feet | $P_s$, lb/ft |
|---|---|---|---|
| 12-inch pipe | 194,843 | 19.125 | 10,188 |
| 16-inch pipe | 268,295 | 24.000 | 11,179 |

As seen in Table 3, the passive lateral resistances are 3,094 lb/ft and 3,252 lb/ft, for the 12 and 16-inch pipes, respectively. Because the radial force reaction necessary to restrain the line exceeds the internal passive soil resistance, one may reasonably conclude that movement will take place at bends in response to temperature changes exceeding about 30 percent of the maximum temperature change.

Longhand analysis of the forces and moments generated by deformations at a bend are difficult to execute. Therefore, we will take two approaches. In the first instance, we will analyze side bends of several degrees by treating them as miter bends. This work allows one to understand the concepts involved and provides a bounding upper limit on the forces and moments because the flexibility of a large-radius bend significantly reduces the forces and moments. In the subsequent section we present an analysis of actual bends using CAEPIPE™. Then, we compare solutions. Finally, we calculate stresses in the pipe at the bends assuming a wrinkle amplitude of 1.5 times the wall thickness. The results will show that the existence of wrinkles no greater in amplitude than 1.5 ties the wall thickness is not a threat to the integrity of the pipeline.

Simplified Analysis of Forces and Moments Using the Rigid Miter Bend Configuration If one assumes that each bend consists of a single rigid miter joint, one can calculate by relatively simple equations, the forces, moments, and displacements at the bend due to a change in temperature. Actually, a miter bend is not rigid but we will assume it to be.

Figure 6:
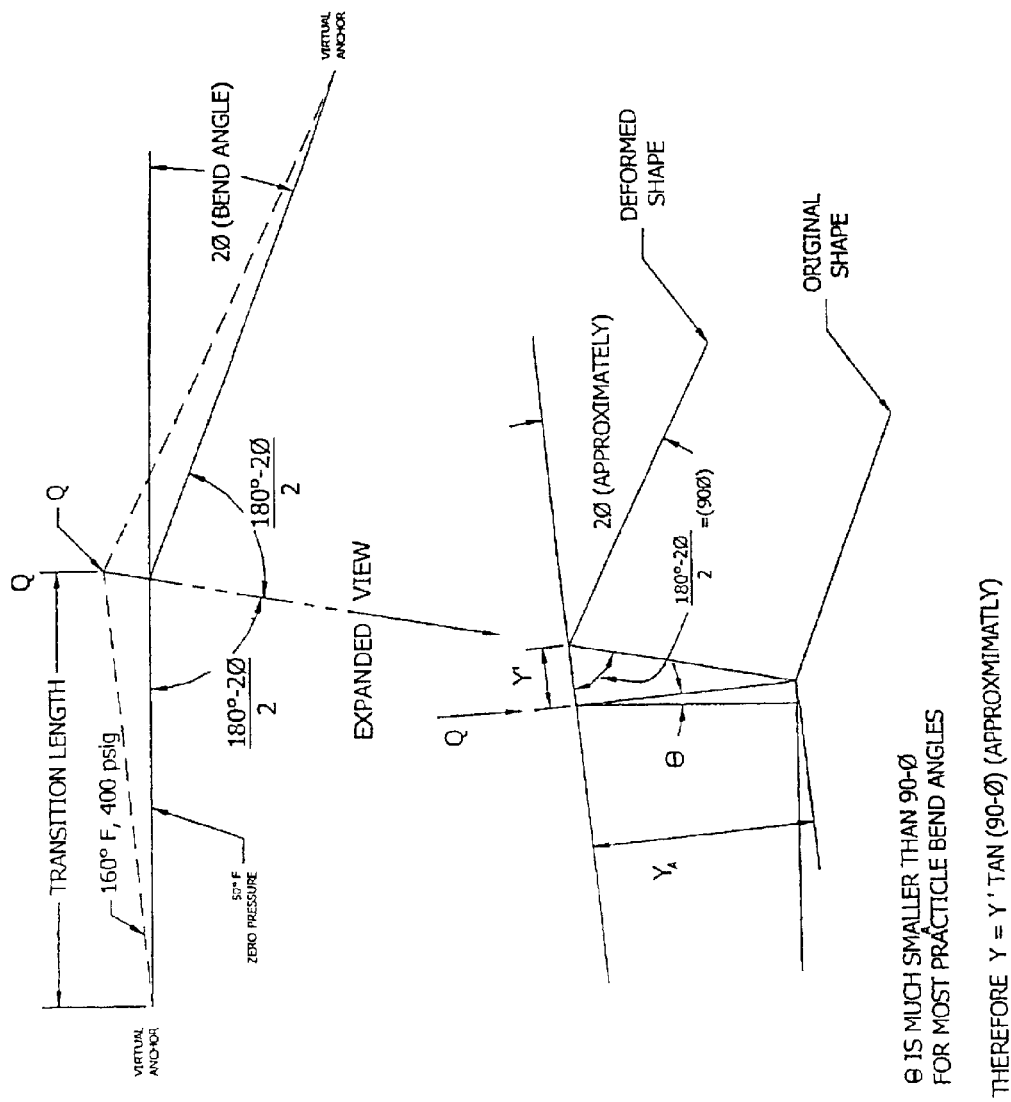

For any miter bend of angle $2\phi$, knowing that y is the free end movement, one can postulate a movement y' as defined in FIG. 6 such that the axial load in the pipe will be $$N = F\left(1 - \frac{y'}{y}\right) \quad (19)$$

The axial load, N, is less than the total anchor force, F, because the movement, y', takes place. However, the movement is resisted by the elastic reaction of the soil. The latter creates a force, Q, perpendicular to the end of each leg at the miter joint. For equilibrium to exist $$N\sin 2\phi = Q + Q\cos 2\phi$$

and therefore $$N = Q\sin 2\phi/(1 - \cos 2\phi) \quad (20)$$

Also, from FIG. 6, one can see that the y' end movement of each leg creates a movement perpendicular to each leg, $y_A$, that is approximately equal to $$y_A = y'[\tan(90 - \phi)]$$

Thus $$y' = \frac{y_A}{\tan(90 - \varphi)} \quad (21)$$

Based on FIG. 6, the reaction load, Q, perpendicular to the pipe at the miter joint will be $$Q = F\left(\frac{1 - \cos 2\varphi}{\sin 2\varphi}\right)\left(1 - \frac{y_A}{y\tan(90 - \varphi)}\right) \quad (22)$$

From Reference 17 pp 52, 53 one can determine that the moment applied to the miter bend is:

$$M_0 = Q/2\lambda \quad (23)$$

where:

$$\lambda = \left(\frac{K}{EI}\right)^{\frac{1}{4}} \quad (24)$$

This circumstance arises from the superposition of the "concentrated force" case and the "concentrated moment at one end" case when the sum of the slopes for the two cases are assumed to be zero, sinhL is approximately equal to cosh$\lambda$L and sinhL is much greater than sinh$\lambda$L.

Because we note that the deflections caused by $M_o$ and Q must add to equal (27) can determine that $$Q = \frac{y_A K}{\lambda} \text{ and} \quad (25)$$

$$M_o = \frac{y_A K}{2\lambda^2} \quad (26)$$

We can now solve Equation 22 for $$y_{A.} = \frac{F(1 - \cos 2\varphi)/\sin 2\varphi}{K/\lambda + F(1 - \cos 2\varphi)/[y\sin 2\varphi \tan(90 - \varphi)]}$$

For the 12.75-inch OD pipe
$\lambda_{12} = 0.01155$ in$^{-1}$
$K_{12} = 52.7$ lb/in$^2$
$F_{12} = 194,843$ lb The deflections, reactions, moments, and axial loads for several bend angles are as follows.

| 12.75-inch pipe | | | | | |
|---|---|---|---|---|---|
| 2 $\varphi$ degrees | 2 $\varphi$ radians | $y_A$, in | Q, lb | $M_o$, in-lb | N, lb |
| 10 | $\pi/18$ | 0.551 | 16,817 | 728,014 | 192,221 |
| 12 | $\pi/15$ | 0.658 | 20,083 | 869,412 | 191,081 |
| 15 | $\pi/12$ | 0.815 | 24,883 | 1,077,182 | 189,004 |
| 30 | $\pi/6$ | 1.516 | 46,285 | 2,003,690 | 172,739 |
| 60 | $\pi/3$ | 2.311 | 70,568 | 3,054,904 | 122,228 |
| 90 | $\pi/2$ | 2.293 | 70,030 | 3,031,590 | 70,030 |

For the 12.75 inch OD pipe
$\lambda 16 = 0.0097128$ in$^{-1}$
$K_{12} = 376.2$ lb/in$^2$
$F_{12} = 268,295$ lb The deflections, reactions, moments, and axial loads for several bend angles are as follows.

16-inch pipe

| 2 φ degrees | 2 φ radians | $y_A$, in | Q, lb | $M_o$, in-lb | N, lb |
|---|---|---|---|---|---|
| 10 | π/18 | 0.708 | 23,067 | 998,511 | 263,652 |
| 12 | π/15 | 0.844 | 27,500 | 1,190,474 | 261,645 |
| 15 | π/12 | 1.043 | 33,967 | 1,470,438 | 258,006 |
| 30 | π/6 | 1.894 | 61,697 | 2,670,880 | 230,258 |
| 60 | π/6 | 2.691 | 87,665 | 3,795,018 | 151,840 |
| 90 | π/2 | 2.495 | 81,280 | 3,518,615 | 81,280 |

CAEPIPE Results

The analyses cases run with the CAEPIPE software produced the following results for the 12.75-inch and 16-inch pipes.

| | Bend Angle 2φ degrees | Analysis Point | Deflection, inch X | T | Moment ft-lb | in-lb | N, lb | Nominal Stress $S_{LC}$, psi |
|---|---|---|---|---|---|---|---|---|
| CAEPIPE Results for 12.75-Inch Pipe | | | | | | | | |
| Tangents | 12 | 248 | 0.068 | −0.240 | −13856 | −166,272 | 161,882 | 13,497 |
| Mid-bend | 12 | 310B | 0.072 | −0.586 | 37538 | 450,456 | 162,733 | 37,396 |
| Tangents | 15 | 248 | 0.102 | −0.268 | −18242 | −218,904 | 160,984 | 11,355 |
| Mid-bend | 15 | 320A | 0.109 | −0.723 | 42035 | 504,420 | 162,202 | 39,413 |
| Tangents | 30 | 248 | 0.321 | −0.299 | −33403 | −400,836 | 155,171 | 3,621 |
| Mid-bend | 30 | 350A | 0.370 | −1.259 | 48161 | 577,932 | 157,605 | 41,684 |
| Tangents | 60 | 248 | 0.768 | −0.234 | −34467 | −413,604 | 143,335 | 1,672 |
| Mid-bend | 60 | 360B | 0.898 | −1.471 | 25466 | 305,592 | 145,225 | 29,653 |
| Tangents | 90 | 248 | 1.132 | −0.208 | −28165 | −337,980 | 133,705 | 3,406 |
| Mid-bend | 90 | 390A | 1.196 | −1.067 | 19843 | 238,116 | 135,069 | 25,801 |
| CAEPIPE Results for 16-Inch Pipe | | | | | | | | |
| Tangents | 12 | 246 | 0.091 | −0.158 | −25,019 | −300,228 | 219,206 | 13,092 |
| Mid-bend | 12 | 310B | 0.095 | −0.795 | −59,634 | 715,608 | 220,430 | 36,273 |
| Tangents | 15 | 246 | 0.121 | −0.149 | −31,100 | −373,200 | 217,719 | 11,299 |
| Mid-bend | 15 | 320A | 0.129 | −0.865 | 66,438 | 797,256 | 219,416 | 38,035 |
| Tangents | 30 | 248 | 0.396 | −0.497 | −59,586 | −715,032 | 207,843 | 2,639 |
| Mid-bend | 30 | 350A | 0.448 | −1.530 | 77,415 | 928,980 | 211,682 | 40,324 |
| Tangents | 60 | 248 | 0.973 | −0.413 | −67,625 | −811,500 | 187,123 | −1,434 |
| Mid-bend | 60 | 380B | 1.165 | −1.918 | 46,473 | 557,676 | 190,740 | 29,989 |
| Tangents | 90 | 248 | 1.117 | −0.210 | −28,179 | −338,148 | 134,088 | 4,499 |
| Mid-bend | 90 | 340A | 1.189 | 1.096 | 20,384 | 244,608 | 135,467 | 17,859 |

If we take the worst case CAEPIPE results for the 12.75 inch pipe (mid-bend of the 30 degree bend), we find that the peak stress range $$\Delta S_{P12} = 3.8 S_{LC} = 4.2 \left[ \frac{157,605}{8.13} + \frac{577,932(12.75/2)}{\pi(12.75/2)^3(0.203)} \right]$$

$$= 4.2[19386 + 22298]$$

$$= 4.2[41684]$$

$$= 175,073 \text{ psi}$$

Figure 7:
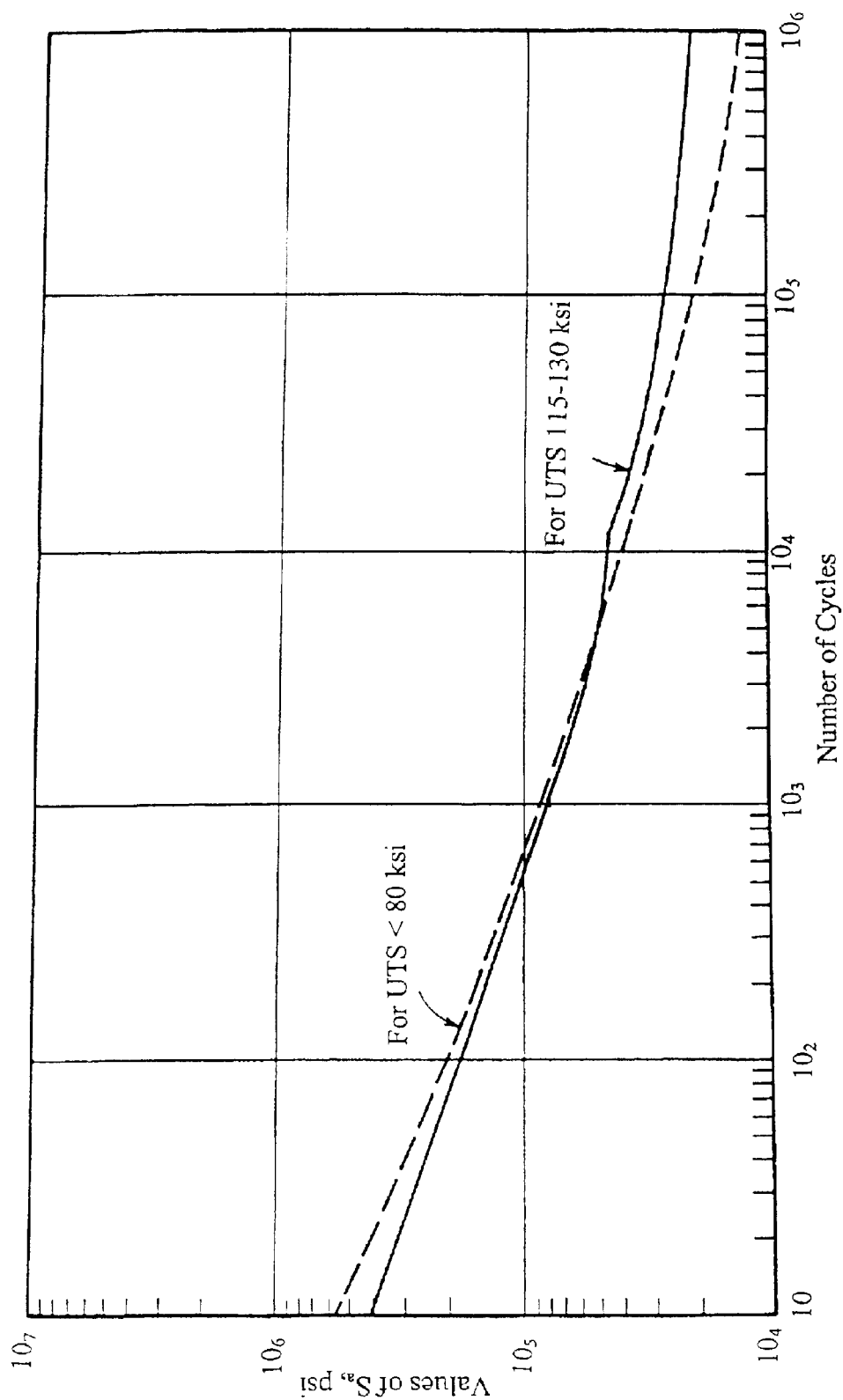

This stress level clearly exceeds the yield strength of the material, but that is not an indication of a failure condition. In terms of piping stresses this is a condition which calls for an estimation of the "design life" of the bend. One basis for design life is the ASME Boiler and Pressure Vessel Code, Section VIII, Div 2, FIG. 7. In this figure, $S_a$ is the cyclic stress amplitude, equal to one-half the stress range of 175,073 psi. Using the design curve for an 80,000 psi ultimate tensile stress material, we find that the number of cycles allowed for this stress amplitude within the design limits of the code is 855 for the 12-inch pipe. Therefore, wrinkles with h/t values not exceeding 1.5 would have a design life of at least 855 cycles for the conditions we assumed. The conservative nature of our assumptions and analyses suggests that the design life of these wrinkles would be at least 855 cycles, and that the number of cycles required to produce failure would be much larger.

Similarly, for the 16-inch pipe, one finds that the stress intensification factor for a wrinkle h/t value of 1.5 is 3.8. Therefore (for the mid-bend area of the 30-degree bend), $$\Delta S_{P16} = 3.8 S_{LC}$$

$$= 3.8 \left[ \frac{211,682}{11.01} + \frac{928,980(16/2)}{\pi(16/2)^3(0.219)} \right]$$

$$= 3.8(19226 + 21098)$$

-continued $$= 3.8(40324)$$

$$= 153,231 \text{ psi}$$

On the basis of the of the ASME design life curve mentioned above, the wrinkles in the 16-inch pipe with an h/t ratio of 1.5 would have a design life of 1,240 cycles. The results of these analyses show that there is no reason to expect the formation of new wrinkles in straight segments of the Piney Point Pipeline in locations where the soil is stable. An overly conservative analysis of the field bends suggest that even those that contain wrinkles having crest-to-trough heights less than or equal to 1.5 times the wall thickness have a substantial amount of serviceability in terms of fatigue life. The analysis reveals the design levels to be a minimum of 855 cycles of operation for the 12-inch pipe and a minimum of 1,240 cycles of operation for the 16-inch pipe for a temperature change of 110° F. (50° F. to 160° F.). The assumption of a relatively weak soil produced these predicted cyclic design lives. With the soil constants selected, the elastic stresses in some of the larger bends would slightly exceed the ASME B31.4 design limit. In contrast, we ran one case of CAEPIPE with a stiff soil. In that case, the elastic stresses in the bends are within the design limits and the design life of the 1.5 t wrinkle increased to 37,000 cycles.

Pipeline Failure Mechanisms

Some types of failures that can occur in pipelines can be classified into the following categories:

Infant Mortality Failures from Fabrication Flaws. These include failures at defective welds and failures resulting from material flaws such as excessively brittle properties. As the term implies, these failures occur quickly after the pipeline is placed in service and are not of concern for pipelines, such as the Piney Point pipeline, with many years of service experience.

Failures Caused by Ground Instability. A common cause of pipeline failure is a response to ground stability problems such as earthquake motion and landslides. This is not considered to be a problem for the Piney Point pipeline because Southern Maryland is not a seismically active region and the land topography is not prone to landslides or other instabilities.

Corrosion Related Failures. Pipe wall thinning from either internal or external corrosion can 1 cause wall failures and leaks. The primary method for prevention of such failures is monitoring the pipe for thinning by periodic in-line inspections. The Piney Point pipeline has been monitored for corrosion by inspections and repaired when significant corrosion has been detected. There are currently no unrepaired locations in the Piney Point pipeline where the corrosion depth is more than 40% of the original wall thickness. Remaining wall thicknesses in the pipeline are well above required thickness.

Failures Resulting from Progressive Failure Mechanisms Such as Fatigue Cracking. This is the type of failure that occurred in the Piney Point pipeline at Swanson Creek. Such failures occur at locations where the pipeline experiences high loading which causes progressive damage such as fatigue. Progressive damage failures typically after prolonged periods of service and are the equivalent of "wear out" failures of machine components.

Based on the failure experienced at Swanson Creek and evaluation of recent in-line inspection data, the progressive failure mechanism is of primary concern, and relates to fatigue cracking at high stress locations, notably wrinkle bends. Evaluations of the potential for additional failures by this mechanism must include consideration of the following:

Current condition of the pipe at other identified geometric anomalies, which are assumed to be wrinkles based on UT inspection data and results from sample excavations of the pipe.

Evaluation of the possibility that additional wrinkle bends will be formed during service.

Evaluation of the possibility the identified wrinkle bends can rapidly increase in severity such that 1997 inspection data are no longer applicable.

Mechanics of Heated Buried Pipelines

Unlike free hanging pipe systems, which are designed with frequent 90 degree direction changes to provide flexibility for thermal expansion, buried pipelines are typically nearly straight over long distances so that they must accommodate thermal expansion by developing an axial compressive elastic strain. Because the end-to-end length of a buried pipe does not change when it is heated and lateral motions are prevented by the soil, the pipe develops an essentially uniform compressive elastic strain along its length equal and opposite to the thermal expansion strain that would occur in a free pipe. This elastic strain F has a value of $$\epsilon = -\alpha \Delta T \tag{28}$$

where $\alpha$ is the coefficient of linear expansion ($6.4 \times 10^{-6}/°$F. for steel) and $\Delta T$ is the temperature change. The stress $\sigma$ induced by the constrained thermal expansion is $$\sigma = E\epsilon = -E\alpha\Delta T \tag{29}$$

where E is the Young's modulus of the pipe ($30 \times 10^{-6}$ psi for steel near ambient temperature). Assuming a temperature rise of 110° F. (from 50 to 160° F.), the stress induced by constrained thermal expansion is $$\sigma = -30 \times 106(6.4 \times 10-6)(110) = 21,120 \ psi \tag{30}$$

This thermally induced stress acts parallel to the axis of the pipe and is of the same order of magnitude as design hoop stress in the pipe wall from internal pressure.

Using the cross sectional area of the pipe wall, the axial force in the pipe from the constrained thermal expansion can be calculated. The calculated forces are 172,000 lb for the 12 in. OD pipe and 232,000 lb for the 16 in. OD pipe.

The thermal expansion induced stress is of an acceptable magnitude and causes no problems with the pipe provided that the pipe is prevented from bending excessively as a result of the axial force in the pipe. The axial force could conceivable induce bending in the pipe in two ways: (1) as a result of buckling in straight lengths of pipe or (2) from the lateral components of the axial force at locations where the pipe changes direction. Bending from these effects is resisted by the support that the pipe receives for the soil.

Figure 8:
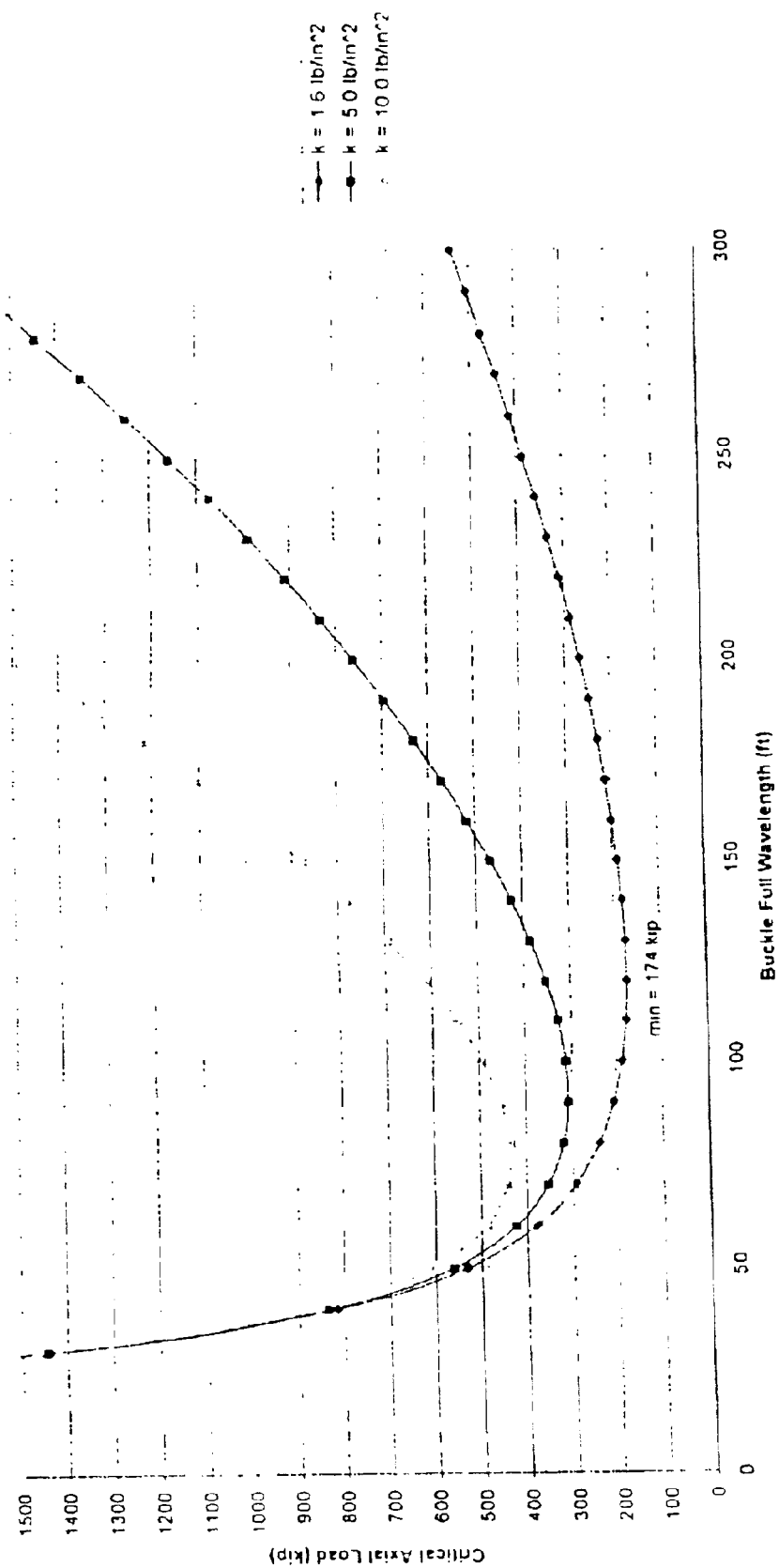

Buckling: A straight length of pipe subjected to a compressive axial force would be expected buckle when its length exceeds the critical buckling length if it does not receive lateral support. However, it can be shown easily that the backfill around a buried pipe provides sufficient lateral support to prevent buckling in an unlimited length of straight pipe. The pipe is analyzed as a beam on an elastic foundation. It can be shown that a beam with elastic lateral support (a beam on an elastic foundation) has a critical buckling load that has a minimum value at intermediate lengths (FIG. 8). For short pipe lengths, buckling is primarily resisted by the bending stiffness of the pipe. The critical buckling load from the pipe bending stiffness decreases as the pipe becomes longer. For long lengths, the buckling resistance is provided primarily by the lateral spring support. The critical buckling load from the lateral spring support increases as the pipe becomes longer. The two effects combined produce a minimum in the critical buckling load value as shown for a 12 in nominal OD pipe in FIG. 8. The minimal critical Q buckling loads for the 12 in. OD pipe occur near 100 ft characteristic wavelength.

As can be seen from the figure, the soil does not need to provide very much lateral support for the buried pipe to keep the minimum buckling load above the calculated 172,000 lb (172 kip). An effective spring constant for the soil of 1.6 lb/in. of deflection/in. of pipe length (19.2 lb/in of deflection/ft of pipe length) maintains the critical buckling load for the 12 in. OD pipe above 174,000 lb. Clearly the soil around the pipe is capable of resisting lateral deflection of the pipe by 19.2 lb per foot of pipe length, which corresponds to a soil pressure of only 18 psf if the pipe deflects an inch laterally. The 16 in. OD pipe has greater buckling resistance than the 12 in. OD pipe. As will be shown in the following, the requirements for soils support of the pipe to resist buckling of straight lengths are much more modest than the requirements to resist bending at locations where the pipe changes direction. Therefore, buckling of straight lengths of buried pipe heated by 110° F. is not expected. Therefore, buckling of straight pipe is not a mechanism for formation of wrinkles.

Bending at Direction Changes

Where heated buried pipes make small changes in direction, the axial force from thermal expansion resolves to create a local lateral force. For example, at a five degree direction change in the 12 in. OD pipe, the 172,000 lb axial force produces a 15,000 lb lateral force component. This lateral force in the pipe must be resisted by the soil if the pipe is to be prevented from bending excessively. In general, the soil can easily provide the required support to the pipe. If one considers that the lateral force created by the axial constrained thermal expansion force and the direction change is supported by the soil over a pipe length of 10 pipe diameters on either side of the center of the direction change, and using the 12 in. OD pipe as an example, the force that the soil must apply to the pipe is 706 lb/ft of pipe length. (10 diameters was chosen because the stiffness of the pipe is sufficient to spread the load over that length without creating excessive bending stresses in the pipe.) This force corresponds to a pressure exerted by the soil on the pipe OD surface of only 660 psf. (This calculation does not take credit for the large effective OD surface area of the pipe created by the insulating jacket). For reference, 600 psf is approximately the pressure exerted on the soles of the feet of a 200 lb person standing still with both feet flat on the ground. Where the pipe is buried in compacted backfill, the soil easily provides the lateral support for the pipe required to prevent large bending stresses from being experienced by the pipe wall.

At most locations, direction changes in the pipeline are accomplished by smooth bends. In this case, the pipe acts as an arch to distribute the lateral support forces from the soil over a long length of pipe with minimal bending moments. Only where the direction change of the pipe occurs over a relatively short length is bending resistance required to transfer the forces from the pipe to the soil. Such abrupt direction changes occur in the Piney Point pipeline only at locations where wrinkles have formed at bends or where forged elbow fittings are used. Extensive stress analysis of wrinkles is described in a separate report. Evaluation of the forged fittings in the pipeline is a part of the return to service program not covered by this report.

Comparison of the soil pressure required to support a five degree direction change (660 psf) and the soil pressure required to prevent buckling of straight pipe (18 psf) demonstrates how little is required from the soil to prevent straight lengths of pipe from buckling under the action of the thermal expansion induced axial force.

Characteristics of Wrinkle Bends

Evaluation of the data from the 1997 in-line inspection of the of the Piney Point pipeline using the ultrasonic system identified a number of anomalous features where the reflected UT signal was lost as the inspection pig passed the feature. One of these anomalies was at the location of the Swanson Creek pipe wall failure in 2000. Excavation and examination of several of the features have shown them to be wrinkles in the pipe wall where there is a small change in direction of the pipe (wrinkle bends). Wrinkles are through wall bending distortions of the pipe wall on the intradose of the pipe bend. The distortion takes the shape of a smooth wave of deflection of the pipe wall from its nominal position. The wrinkle may have a single radially inward or outward bulge or more than one bulge alternating inward and outward. The wrinkles that have been examined have various heights and wavelength of bulge. In most cases, the ratio of the bulge wavelength to maximum height (aspect ratio) is large (greater than eight) representing a gradual smooth distortion of the pipe wall. Wrinkles generally extend less than 180 degrees around the circumference of the pipe. The excavated wrinkle features (other than Swanson Creek) have been examined by ultrasonic tests (UT) that have been qualified for detection of ID cracks. No cracks have been found.

The wrinkle at the location of the Swanson Creek failure is an outlier compared to the other wrinkle bends that have been excavated. The wrinkle at the Swanson Creek failure has a significantly larger outward bulge in the pipe wall than those observed at other locations. At the same time, the wavelength of the Swanson Creek wrinkle is shorter than typical giving the wrinkle a very small aspect ratio of approximately 3. The outward bulge at the Swanson Creek wrinkle bend extends approximately 270 degrees around the pipe circumference, which is significantly greater than is the case for other wrinkle bends that have been examined. The Swanson Creek wrinkle is also a single outward bulge with no associated regions of inward deflection of the pipe wall. Most of the other wrinkle features examined are more sinusoidal in nature with both inward and outward deflections. Thus the Swanson Creek wrinkle is an outlier relative to the more common wrinkle features found at other locations on the pipeline in both its quantitative qualitative characteristics.

Formation of Wrinkles

It is difficult to be certain how the wrinkles observed in the Piney Point pipeline were initially formed. The best estimate of how wrinkles were formed, based on industry experience and laboratory studies is that wrinkles form when the pipe is bent either during fabrication or by service-induced loads. In many cases, at least a small amplitude wrinkle was probably formed during pipeline fabrication. All wrinkles are associated with small angle direction changes in the pipe. In some cases, the wrinkles may have become accentuated when the line was subjected to additional loading in service. Stresses induced by bending moments at small angle chance bends with wrinkles are greater when the wrinkle height is small than when it is large. This indicates that small wrinkles are likely to increase in height if they are subjected to high bending moments.

The increase in wrinkle height increases the compliance of the pipe wall, which spreads out the deformation and reduces peak stresses and plastic strain amplitudes caused by pipe bending moments.

The objective in pipeline fabrication, as set forth in the relevant construction codes, is to accomplish all direction changes in the pipeline with smooth wrinkle free bends. However, many of the wrinkles in the pipe were probably initiated as part of the construction process. When thin wall pipe is bent, it has a tendency to ovalize and wrinkle on the intradose of the bend. To prevent this, bending guides (shoes) are used on the OD of the pipe to force it to remain round while it is bent. When the Piney Point pipeline was laid, field bending was done with the insulating jacket on the pipe. Because of the compliance of the insulation, this process made it difficult to fully constrain the pipe to remain round and wrinkle free while it was being bent. As a result, there were probably a number of locations where small amplitude wrinkles were produced in field bends. In addition, several of the excavated wrinkles appear to be the result of unusual construction damage greater than allowed by the pipeline specification and construction code. These should have been repaired during the construction process if they were observed, but they apparently were not.

Several of the excavated features are what is characterized in the pipeline technical literature as "diamond wrinkles." These are alternating inward and outward bulges around the pipe circumference slightly offset axially. Diamond wrinkles are frequently produced by bending thin walled pipes without proper restraint to keep the pipe from deforming out of round. Other wrinkles are predominantly inward bulges. Wrinkles with inward bulges are most likely formed by bending of the pipe when it is not pressurized. Outward bulges are favored when thin walled pipes are bent with applied internal pressure, but they can also occur if the pipe is bent with restraint against ovalization but insufficient guidance to force it to take a smooth radius of curvature.

Some of the wrinkles in the Piney Point pipeline may have become more severe as the result of deformation in service. The pipeline operates at slightly elevated temperature (up to 160° F.) when transferring heavy oil. Thermal expansion produces a large axia compressive force in the pipe when it is heated (approximately 172,000 lb for the 12 inch pipe, 232,000 lb for the 16 inch pipe). This axial force produces bending, moments in the pipe at direction changes. The magnitude of the bending moment depends on how well the pipe is restrained by the soil in which it is embedded. As discussed above, relatively low support pressures from the soil react unbalanced loads at direction changes so that bending stresses in the pipe are kept small. Firm soil provides sufficient lateral restraint to the pipe to minimize bending. This limits the load on the pipe to a uniform compressive force along the length of the pipe that produces stresses below the elastic, limit for the pipe material. Where the soil does not provide adequate lateral restraint for the pipe, the axial force produces bending moments in the pipe where there is a direction change. Additional bending moments may have been present in the pipe when it was buried as the result of minor cold springing introduced during construction. When bending moments are added to the axial thermal expansion force in the pipe, the yield strength may be exceeded on the side of the pipe where the bending stress is compressive (i.e., on the intradose of direction changes). If a small wrinkle is already present at such a location, the wrinkle geometry creates through wall bending stress from residual and thermally induced axial forces. This can result in sufficiently high stresses to cause local plastic deformation. This localized plastic deformation may change the shape of preformed wrinkles and can create wrinkles in originally smooth bends. Because thermal expansion of the pipe occurs coincident with pressurization of the pipeline, deformation is expected to favor outward deflection of the pipe wall. If cold springing loads were present in the pipe when it was buried, plastic deformation at wrinkle bends can relieve these loads and reduce the stored elastic strain energy in the pipe.

Stability of Wrinkles During Service

Where accentuation or formation of wrinkles in the Piney Point pipeline during service have occurred, it is expected that this happened during the first few heat/pressurize cycles. Finite element analyses that have been performed to evaluate the stresses produced in wrinkles indicate that when soil support is inadequate, localized plasticity is expected to occur at direction changes and wrinkles on the first heat up cycle. This deformation stabilizes the wrinkle geometry in the following ways:

The plastic deformation redistributes the stress in the bend and wrinkle such as to reduce peak stresses.

Changes in the geometry of the wrinkles act to reduce peak stresses and spread loading to more of the pipe wall.

The plastic deformation strain hardens the pipe material.

The plastic deformation relieves cold springing forces that may have been present when the pipe was buried.

Residual stresses are created as the load is removed such that on the next application of the load, the pipe returns to its condition at the peak of the previous load cycle with little or any additional plastic deformation.

All of these effects act to stabilize the pipe for subsequent load cycles. Additional inelastic deformation on subsequent cycles is only expected to occur under the following conditions:

The strain range is sufficiently large to cause reverse plasticity on each unloading and reloading cycle (strain ratcheting). Finite element analyses of a variety of wrinkle geometries indicates that such reverse plasticity is limited to small regions of pipe wall that are restrained by surrounding elastic material that prevents significant changes in the wrinkle geometry after the first loading, cycle.

Loads are increased on subsequent cycles. This is not expected to occur in the future because the pipeline will be operated at pressures and temperatures enveloped by past operating experience.

Soil support conditions degrade. With stable ground conditions (no earth quakes, landslides, or significant subsidence) soil support of buried pipelines is expected to improve with time as backfill consolidates as the result of natural processes. In most cases, soil support is minimum immediately after the pipeline is constructed and trenches have been backfilled. Thus minimum support is available during the first application of loading on a new pipeline. Specifications for compaction of backfill during construction are designed to assure that adequate soil support is generally available for new construction. This minimizes the locations where wrinkles will occur or accentuate.

Results from finite element analyses of pipes with wrinkle bends show that only severe wrinkles characterized by (1) large bulges, (2) small aspect ratios, and (3) large circumferential extents are expected to undergo cyclic plastic deformation leading to ratcheting and continual accentuation of the wrinkle geometry (strain ratcheting). For any wrinkle geometries, ratcheting will occur only for cases where there is minimal support to the pipe provided by the soil. Therefore, the wrinkle bends in the Piney Point pipeline have probably been stable for many years. The existing wrinkles represent locations of elevated stress, but they do not cause concern for additional failures in the short term, and they will be monitored in the future by in-line inspections that will detect any changes in the geometry that might be a precursor to failure. Additional evidence that the existing wrinkle bends are stable comes for the results of excavation and inspection of the pipe at locations where the 1997 UT inspection showed anomalous features. In all cases, the wrinkle geometry found after excavation in 2000 is consistent with the UT signals recorded in 1997. The excavations also provide assurance that none of the existing wrinkles at bends represent possibilities of failures in the near term because UT examinations of the excavated wrinkles have not identified any initiated cracks in the highly stressed material in the wrinkles.

As was noted previously, the wrinkle bend at Swanson Creek that failed was an outlier compared to the other wrinkle bends that have been examined. The wrinkle at the Swanson Creek failure location had the three characteristics listed above that are conducive to continual strain ratcheting.

The failure location was also in poor soil conditions that probably resulted in inadequate support for the pipe at a direction change. It is probable that the wrinkle geometry at Swanson Creek accentuated over several years of service until it became sufficiently severe to allow crack initiation by low cycle fatigue. Even for this outlier, the entire failure scenario took years of operation to complete.

Pipe Wall Failure Mechanisms

The laboratory investigation of the pipe failure at Swanson Creek identifies the failure mechanism as being crack initiation by fatigue with the final rupture occurring by a ductile tearing mechanism. Brittle failure of the material is not indicated by examination of the fracture surface and would not be expected based on the pipe material properties. The mechanism for the failure that occurred is progressive in nature and requires many operating cycles to progress to a through wall leak in the pipe. Such progressive failure mechanisms can be addressed by a long-term reliability program through inspections and monitoring of anomalous features in the pipeline to detect chances that could indicate progression of the failure mechanism.

If additional failures are to occur, they will probably result from a similar mechanism as that experienced at Swanson Creek. No potential failure mechanisms that could lead to pipe wall ruptures in the short term have been identified for the Piney Point pipeline. Based on tests performed on pipe material removed from the pipeline near the failure location, the material is not brittle. Thus, crack propagation can only occur by progressive mechanisms such as fatigue. Unstable tearing fracture can only occur after a precursor crack through most of the pipe wall has been created by a progressive mechanism. No precursor cracks have been found at any of the wrinkle bend locations that have been excavated and inspected. Therefore, no ruptures of the pipe wall are anticipated in the near term.

Acceptance Criteria For Pipeline Wrinkles

In order to determine the acceptability of local wrinkle deformations in pipe bends, stress analyses were performed using the ANSYS finite element program. The purpose of this section is to describe the finite element model used for the analyses, present the results of the finite element model, and to use these results in the development of a set of acceptance criteria for wrinkles in pipe bends. The criteria developed in this appendix are intended for use as a return to service acceptance basis; i.e., wrinkles meeting the criteria developed in this appendix will not require repair or replacement for the Piney Point pipeline to return to service. The results of the analyses performed may also be incorporated into a long-term integrity management program for the pipeline.

Finite Element Model of Wrinkle Geometry

1. Model Geometry

Figure 9:
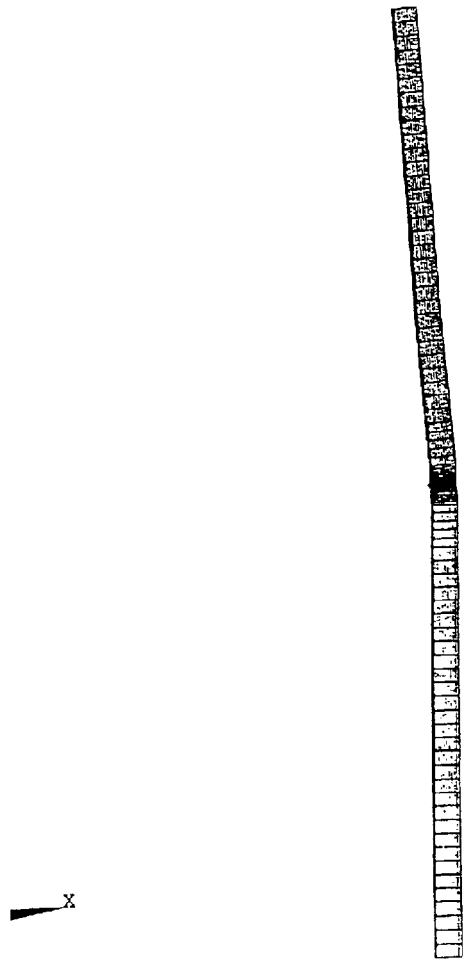

Finite element analyses of a wrinkle in a pipe bend were performed using Revision 5.6 of the ANSYS finite element program from ANSYS, Inc. (Reference 23), on an HP B2000 workstation. As shown in FIG. 9, the overall model consists of a 5 degree horizontal bend of 12.75 or 16 inch OD pipe, with approximately 20 pipe diameters of straight pipe on each side of the bend. Wall thicknesses of 0.203 inches and 0.219 inches were used for the 12.75 inch OD and 16 inch OD models, respectively. The length of the straight piping on each side of the bend is an important boundary condition assumption; further discussion is provided later in this section. The five degree bend is modeled using a radius of 18 times the OD, which is the minimum allowable bend radius for a field bend. All portions of the piping are modeled using 20-node SOLID92 (3-D structural solid) elements.

2. Modeling of the Wrinkle

The finite element model also includes a wrinkle centered in the bend and located at the intrados of the bend. The wrinkle is created as part of the original model, i.e., it is assumed to be a residual-stress free discontinuity on the pipe bend intrados. These analyses do not intend to address the formation of wrinkles in piping; further discussion of the formation of wrinkles is contained in (Reference 21).

Figure 10:
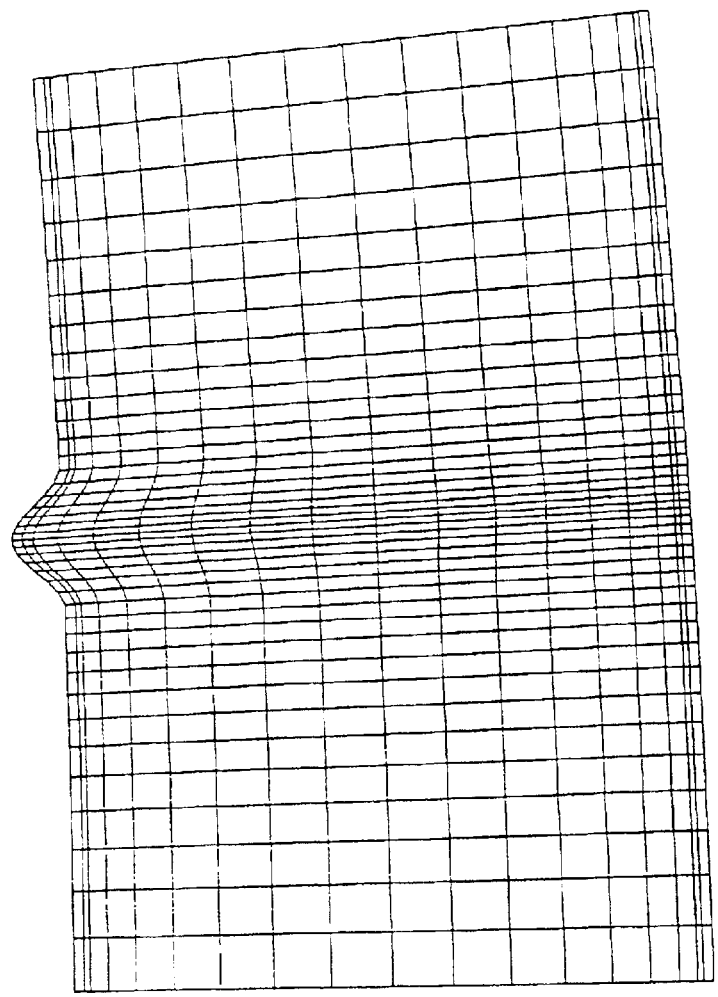
Figure 11:
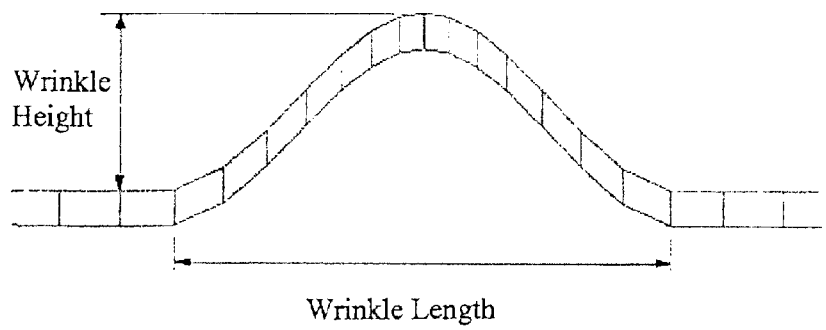
Figure 11:
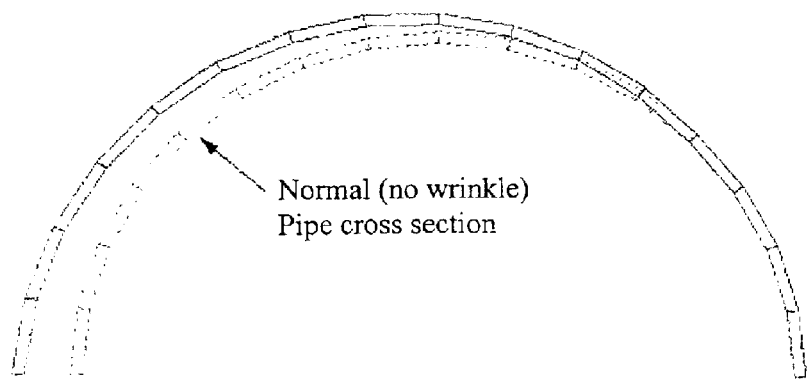

The shape of a single wrinkle is idealized as following a cosine-squared distribution in height versus axial extent and a linear distribution in height versus circumferential extent, with the maximum height occurring at the center of the bend intrados. FIG. 10 is a local view of the wrinkle model, and FIG. 11 shows how a typical wrinkle varies in height circumferentially and axially.

In order to assess the impact of a wrinkle with a given geometry on the thermal expansion stresses in the region, the configuration and specific geometry of the wrinkle are varied as follows:

a. Aspect Ratio

The aspect ratio of a wrinkle is defined as the ratio of the length of the wrinkle, as measured from tip-to-tip of the discontinuity with the pipe nominal OD (see FIG. 11), to the height of the wrinkle, as measured from the nominal pipe OD to the apex of the wrinkle. Aspect ratios of 12, 9, and 6 are analyzed for all variations in wrinkle height and circumferential extent. Limited cases of aspect ratios equal to 7.5 and 3 are also analyzed.

b. Wrinkle Height

Along with being part of the aspect ratio, the height of the wrinkle was treated as an independent variable. Wrinkle heights of 150%, 300%, 400%, and 500% or 600% of the nominal wall thickness are analyzed.

C. Circumferential Extent

Wrinkle circumferential extents of 90, 180 and 270 degrees were analyzed for all variations in aspect ratio and wrinkle height for the elastic analyses performed (see below). For elastic-plastic analyses (see below), circumferential extents of 120, 150, and 180 degrees were analyzed for all variations in aspect ratio and wrinkle height. Limited cases of circumferential extent equal to 270 degrees are also analyzed.

3. Material Properties

Figure 12:
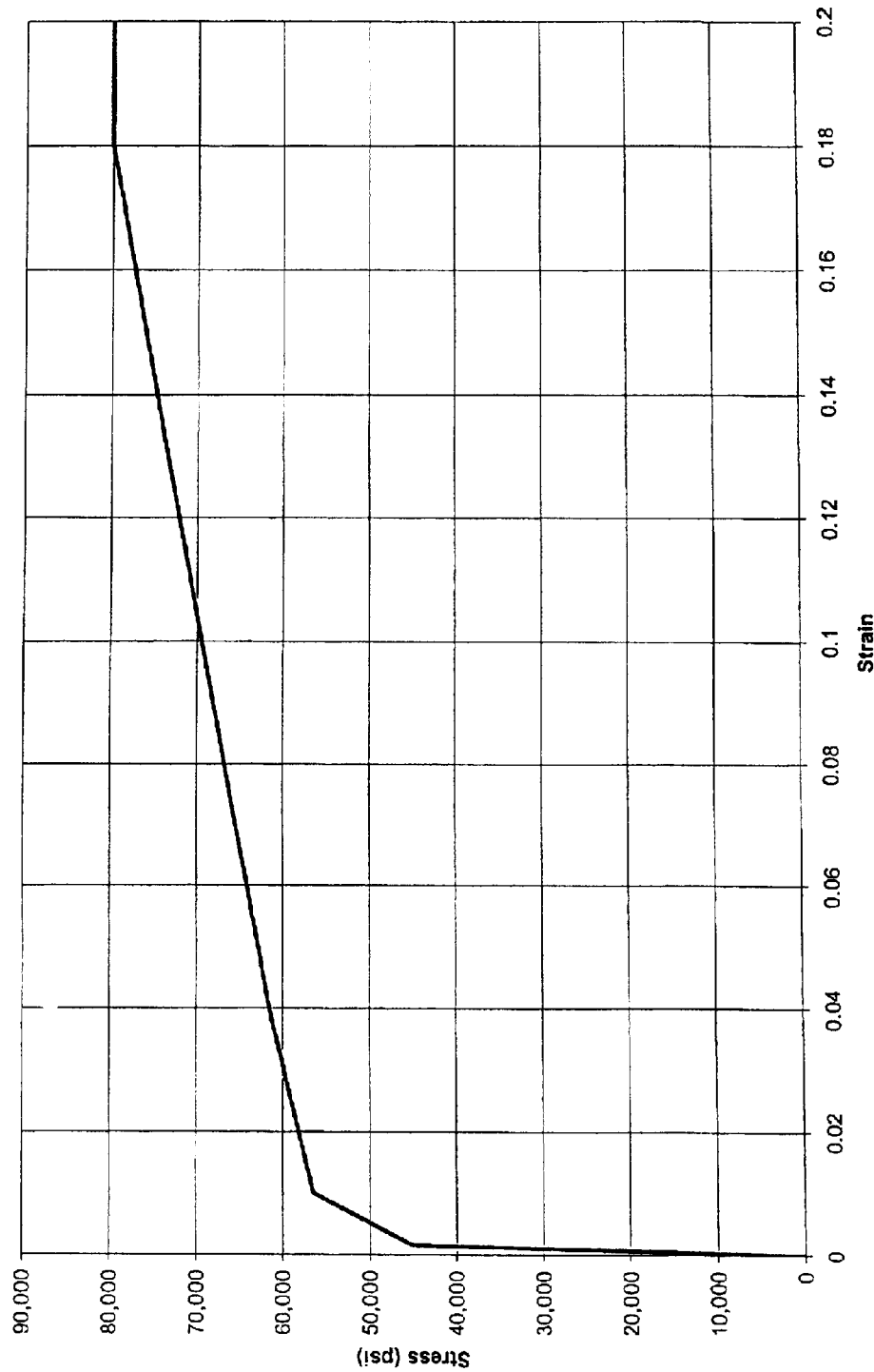

The model geometry was analyzed with elastic material properties as well as elastic-plastic material properties. Material properties appropriate for carbon steel at the temperature range experienced by the pipeline (E=30E6 and v=0.3) were used in both the elastic and elastic-plastic analyses. In addition, a multilinear stress-strain curve was used in the elastic-plastic analyses. A plot of the stress-strain curve input into ANSYS for the pipe material is shown in FIG. 12.

4. Effects of Soil Restraint

When a portion of a buried pipeline consisting of two long, straight runs connected by a change in direction (such as a bend with a wrinkle) is heated, the thermal growth in the straight runs tends to be accommodated by deflection at the change in direction. As the point of change in direction (center of the bend) deflects, the runs of pipe attached to it will deviate from their as-laid, straight configuration. However, all pipe deflection is resisted by the force required to compress or move the soil surrounding the pipe. Depending on the constraint provided by the soil, the amount of deflection at the center of the bend will vary, as will the extent of run piping that deviates from its original configuration.

In the finite element model, the effects of the soil limiting the displacement of the bend center and the piping around it were approximated by preventing the ends of the model from deflecting laterally and allowing the rest of the model to move freely (i.e., no soil restraint). This modeling technique captures the effect of the soil limiting the axial extent of straight pipe that will deviate from the original configuration, while conservatively assuming no restraint from the soil as the bend center deflects. Straight run lengths were selected for the 12 inch and 16 inch piping that were found to produce bend center deflections of approximately 1, 1.5 and 3 inches in models using elastic-only material properties. For the elastic-plastic models, straight run lengths were selected that produced bend center deflections of approximately 1.5 inches in the elastic model; these run lengths typically produced bend center deflections between two and three inches, as discussed later in this section.

5. Boundary Conditions and Loading

Figure 13:
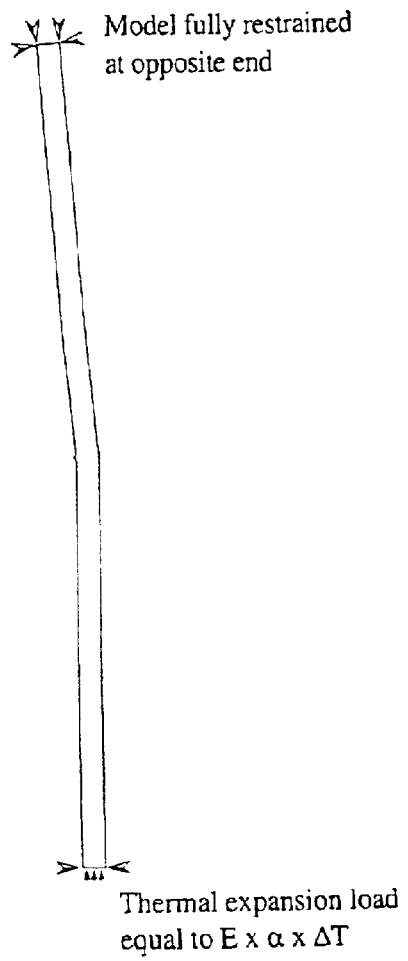

The boundary conditions and loading used in the finite element model are shown in FIG. 13. The model was loaded at the end of one of the straight pipe runs by placing a pressure equal to the thermal expansion stress in a fully constrained cross section, or $P = E \times \alpha \times \Delta T$, where E is 29.5E6, $\alpha$ is the coefficient of thermal expansion, or 6.5E-6, and $\Delta T$ is the change in temperature, assumed to be 110° F. At the same end as the pressure load, the pipe was held in motion transverse to the pipe axis. At the other end of the model, the pipe was held in all degrees of freedom. Because a one-half model was used, symmetry boundary conditions were enforced along the plane of symmetry, located at the vertical midpoint of the piping model.

The loading scenario used causes the pipe model to always carry an axial force equal to the thermal expansion force of a fully constrained section. It is important to note that this model is force loaded and not displacement loaded. Therefore, many of the soil mechanics variables that are difficult to characterize, such as the axial length between the change in direction and the point at which soil friction forces prevent the pipe from further expanding (commonly referred to as the "virtual anchor"), are not required. The force load on the model conservatively causes the piping to deflect until it reaches equilibrium, and therefore does not require an assumed end displacement as an input.

Finite Element Analysis Results

6. Results of Model Using Elastic Material Properties

Figure 14:

When the finite element model is loaded as described previously, the center of the bend tends to deflect outward, or away from the center of the radius of curvature for the bend, as shown in FIG. 14. The wrinkle at the intrados of the bend flexes as the overall geometry deflects.

The loading creates an axially compressive stress in the entire cross section as well as a bending stress that is axially compressive on the intrados and axially tensile on the extrados of the bend. In addition, the flexure of the wrinkle at the intrados creates local bending stresses through the wall of the pipe that are axially tensile or compressive depending on whether the wrinkle is inwardly or outwardly directed. At the wrinkle center, outward wrinkles have compressive axial stresses on the pipe ID and tensile axial stress on the pipe OD; at the wrinkle edge, the compressive stresses are on the pipe OD and the tensile stresses are on the pipe ID. This pattern is reversed for inward wrinkles, with compressive stresses on the OD at the wrinkle center and on the ID at the wrinkle edge. For both inward and outward wrinkles, the compressive stresses are larger in magnitude than the tensile stresses. This is a result of the net compressive axial stress that exists at the intrados of the bend due to axial and bending loads.

The axial stress results from the parametric variations of the elastic model described earlier in this section tuned to yield a bend displacement of approximately 3 inches is listed in Table 4. Selected data from Table 4 are plotted in FIGS. 15–17. It should be noted that the peak stresses calculated using the elastic model are well above the material yield strength and are therefore not realistic. They are useful, however, in demonstrating relationships between the different parametric cases.

Figure 15:
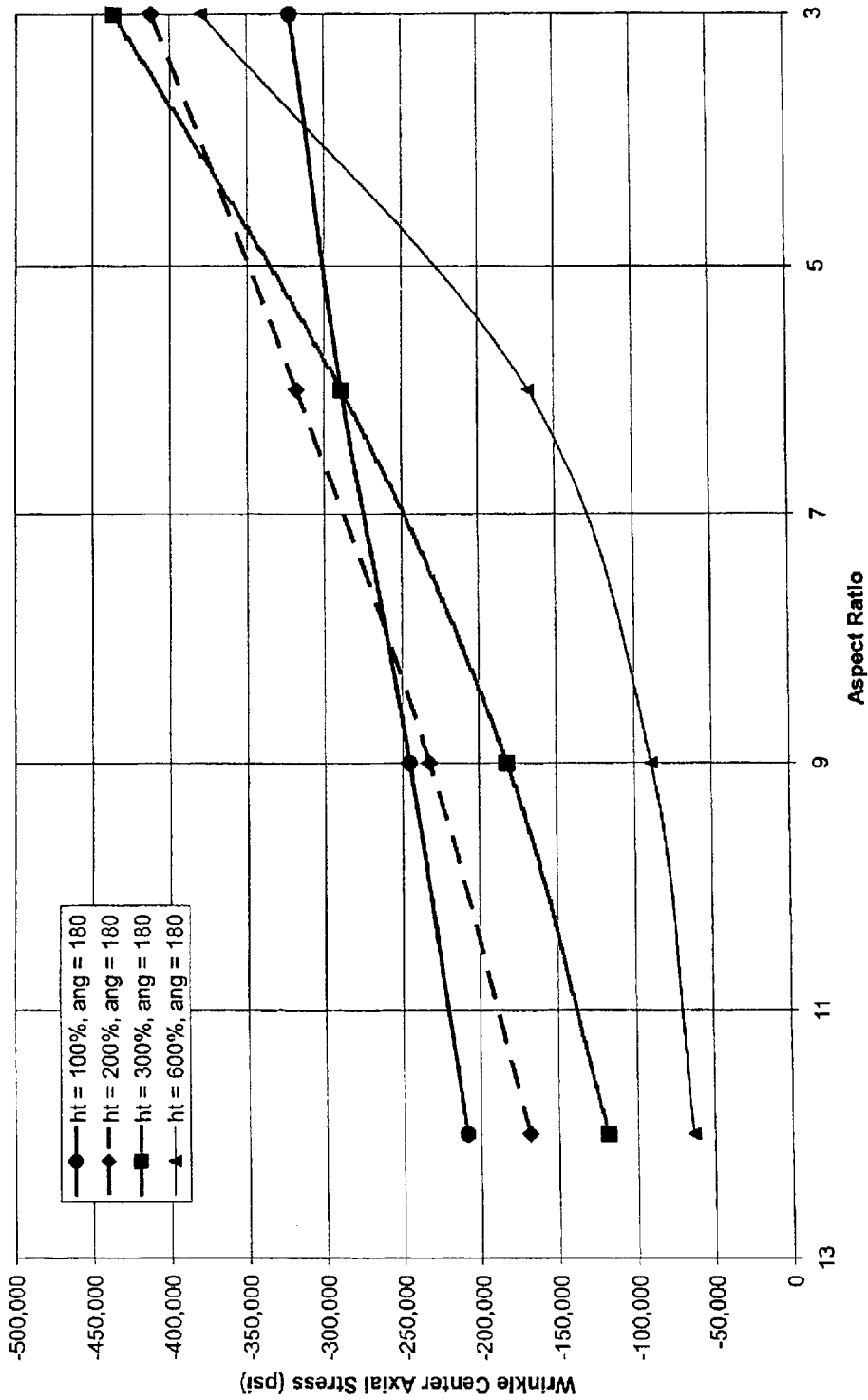
Figure 16:
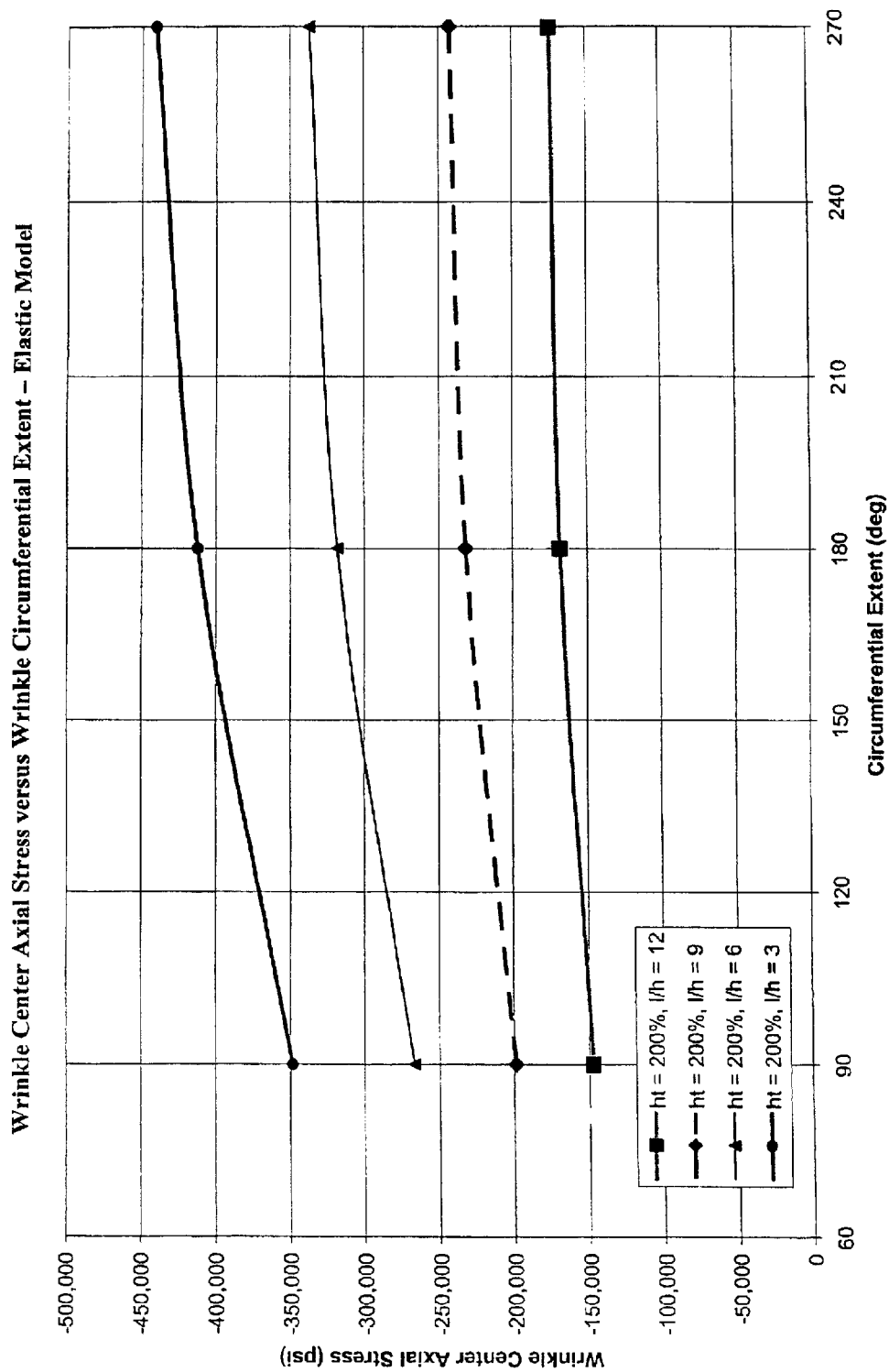
Figure 17:
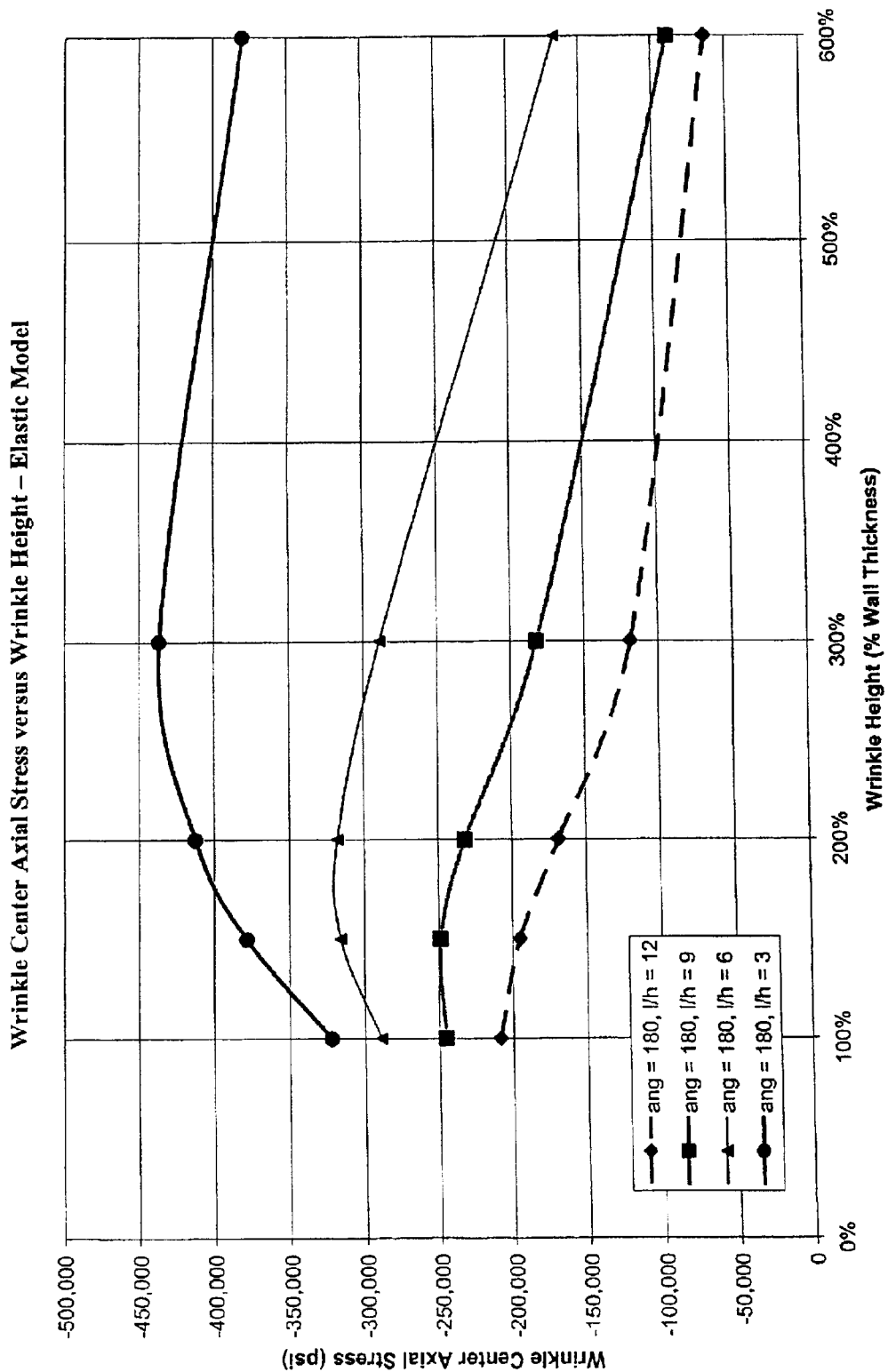

Examination of FIG. 15 shows that peak stresses tend to increase (in absolute magnitude) as aspect ratio decreases, with the effect more pronounced at larger wrinkle heights. Additionally, as shown in FIG. 16, increasing circumferential extent causes peak stresses to increase only slightly. With a few exceptions, bend displacement is very consistent for the elastic model, with nearly all cases within 1% of each other. Another trend, displayed in FIG. 17, is that for larger aspect ratios such as 12 and 9, peak stresses tend to decrease (in absolute magnitude) with increasing wrinkle height. As an example, the maximum stress for the case of a wrinkle with an aspect ratio of 9 occurs when the wrinkle height is 150% of the wall thickness. However, for smaller aspect ratios such as 3, the maximum peak stress increases until the wrinkle height is approximately 300% of the wall thickness, then it decreases again. It should be noted that in no case does the limiting peak stress occur at the maximum wrinkle height for a given aspect ratio. This trend is reasonable since the larger aspect ratios allow for smoother wrinkles with lower stress concentrations and larger wrinkle heights increase the local bending compliance of the pipe wall, which reduces stresses.

7. Results of Model Using Elastic-Plastic Material Properties

As discussed previously, finite element stress calculations using elastic material properties unrealistically resulted in peak stresses well above the material yield strength. In order to more accurately model the true stress and deflection state of the wrinkle region, it was necessary to use elastic-plastic material properties as described earlier in this section. Changing the material properties from elastic to elastic-plastic allows for the material to strain harden, or gain strength as plastic deformation occurs to raise the flow stress above the original yield strength. This tends to spread out the strain in regions with high stresses, such as the wrinkle center. Additionally, when an elastic-plastic model is loaded past the yield point of the material, removing the load does not return the stress and deflection state to zero as an elastic model does. Instead, it is possible to determine the residual stress state of the model once the load has been removed. Therefore, the analysis simulates the application of a single thermal load cycle from ambient to maximum temperature and back to ambient. It should be noted that the wrinkle geometry is created in strain and residual stress free material. In actuality, most of the plastic strain that occurs during the application of the load occurred when the wrinkles were formed. Strain hardening and residual stresses resulting from wrinkle formation will act to reduce the plastic strain that occurs on the first application of a series of load cycles to much less than that calculated by the FEA model.

For the elastic-plastic model parametric variations, stress and deflection data were determined when the model was loaded and after the load had been removed. The Von Mises equivalent stress and the plastic strain (i.e., the amount of strain above the elastic yield point) were calculated for the wrinkle center and wrinkle edge at the pipe wall ID and OD. Additionally, the amount of extra plastic strain accumulated once the load was removed was calculated for each of the four points. This additional plastic strain is the amount of plastic strain that is being reversed as the pipe is thermally cycled. The plastic strain that occurs on unloading is the reversed plastic strain that will be repeated on each thermal loading cycle unless additional cyclic strain hardening increases the material strength sufficiently to prevent additional plastic straining. The stress and strain data for the first load application and removal are reported in Tables 5 and 6 for outward and inward wrinkle shapes, respectively. Selected reversed plastic strain data from Tables 5 and 6 are plotted in FIGS. 18 through 21.

Figure 18:
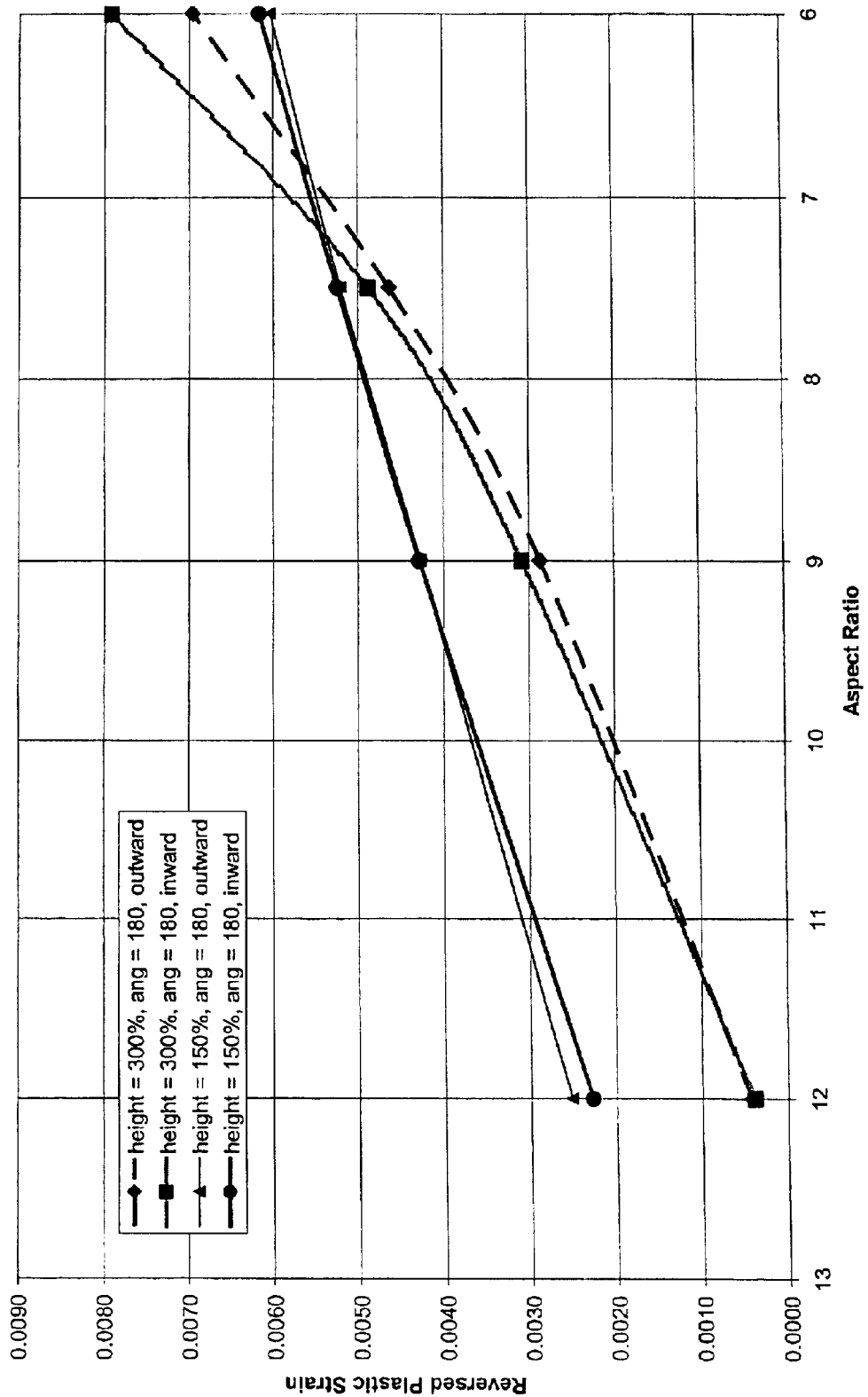
Figure 19:
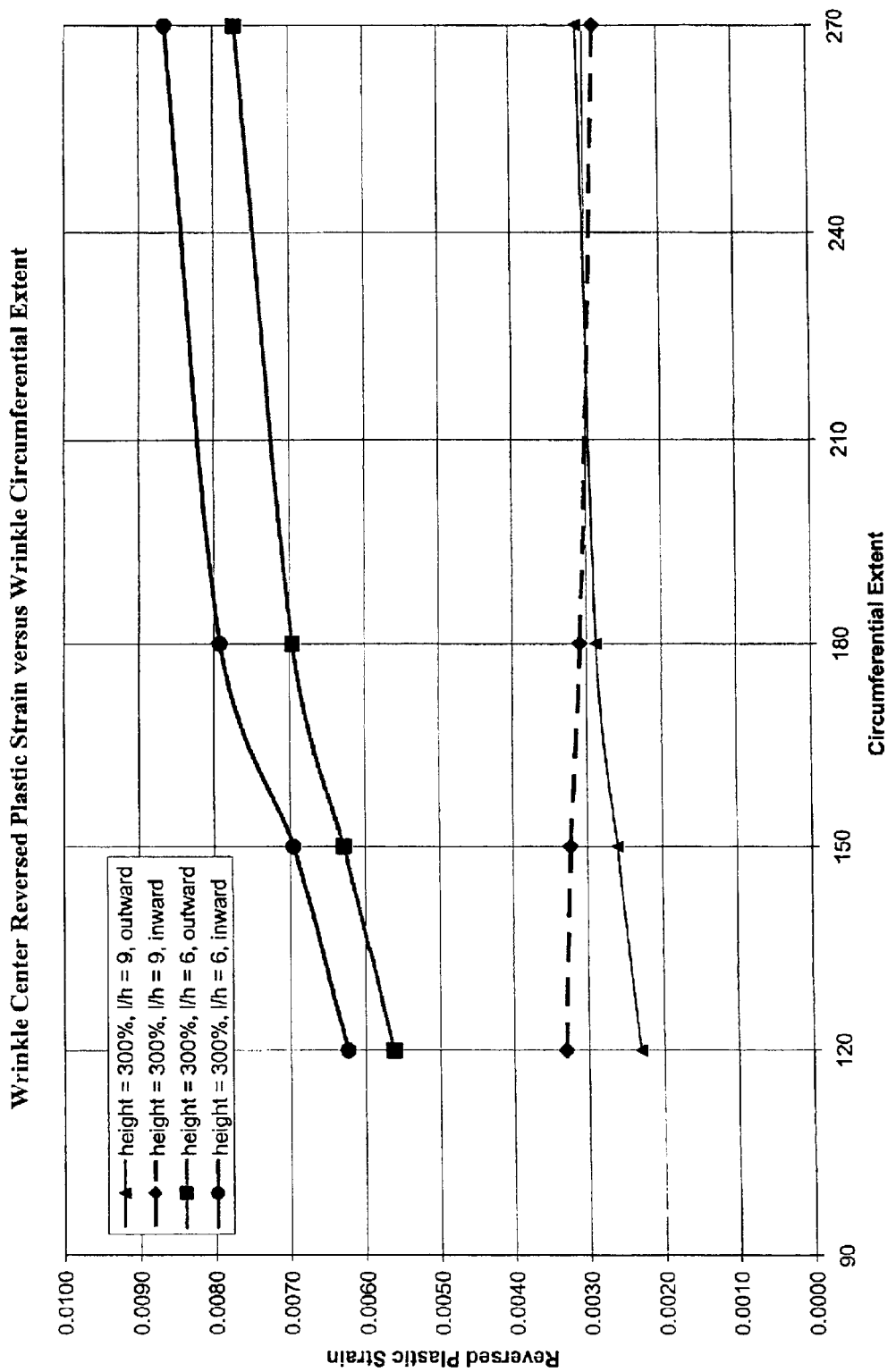
Figure 20:
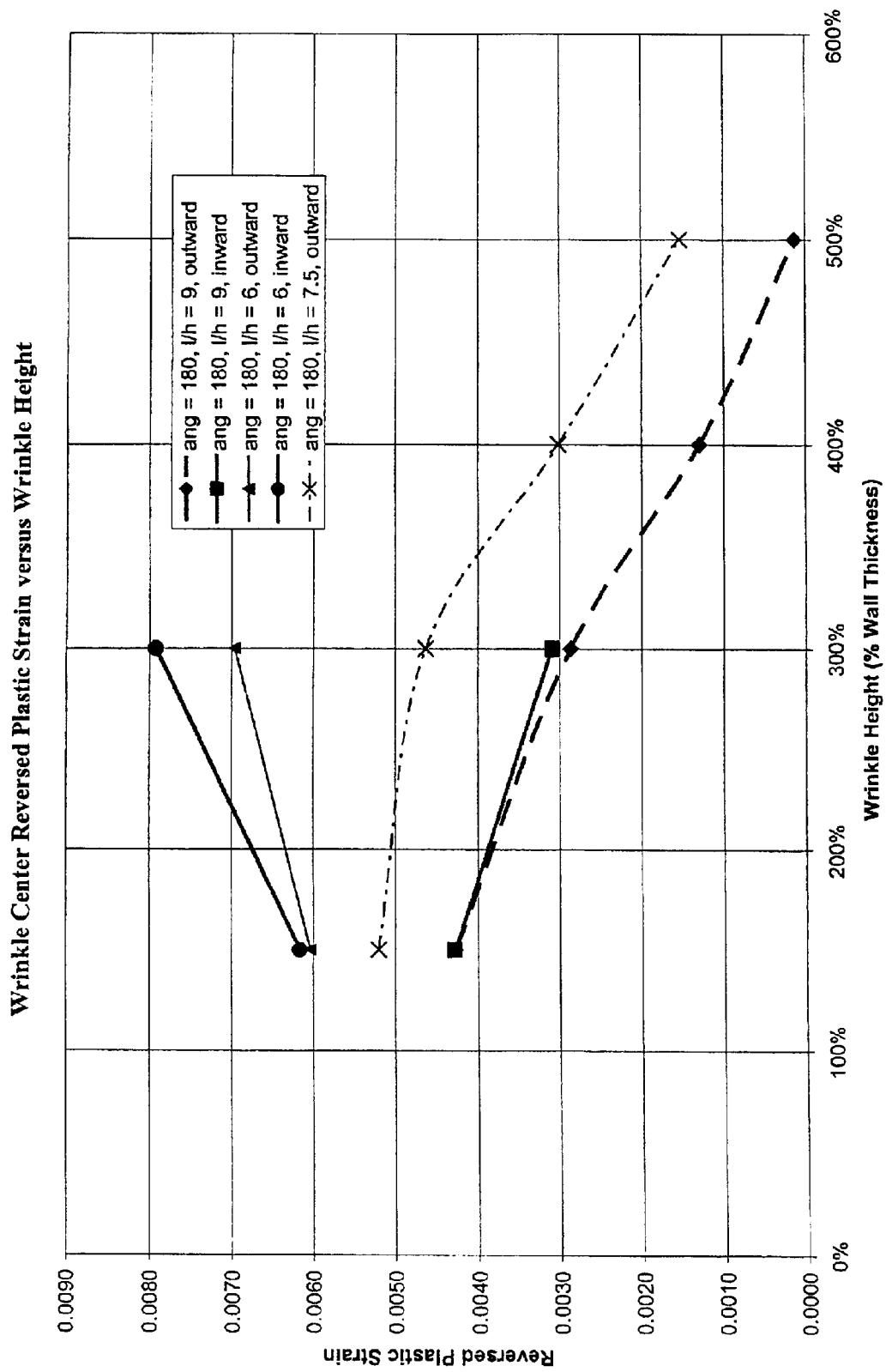
Figure 21:
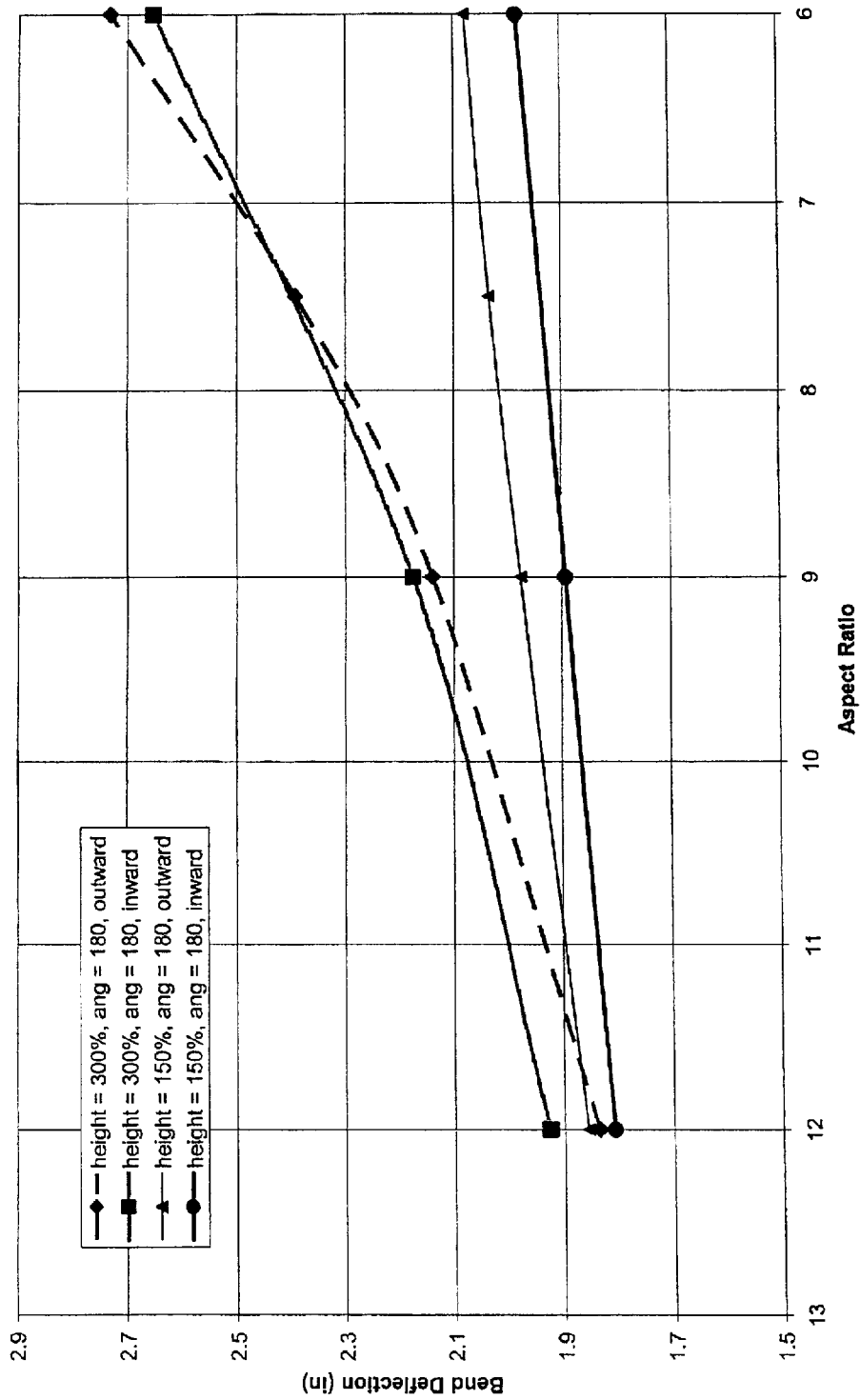
Figure 22:
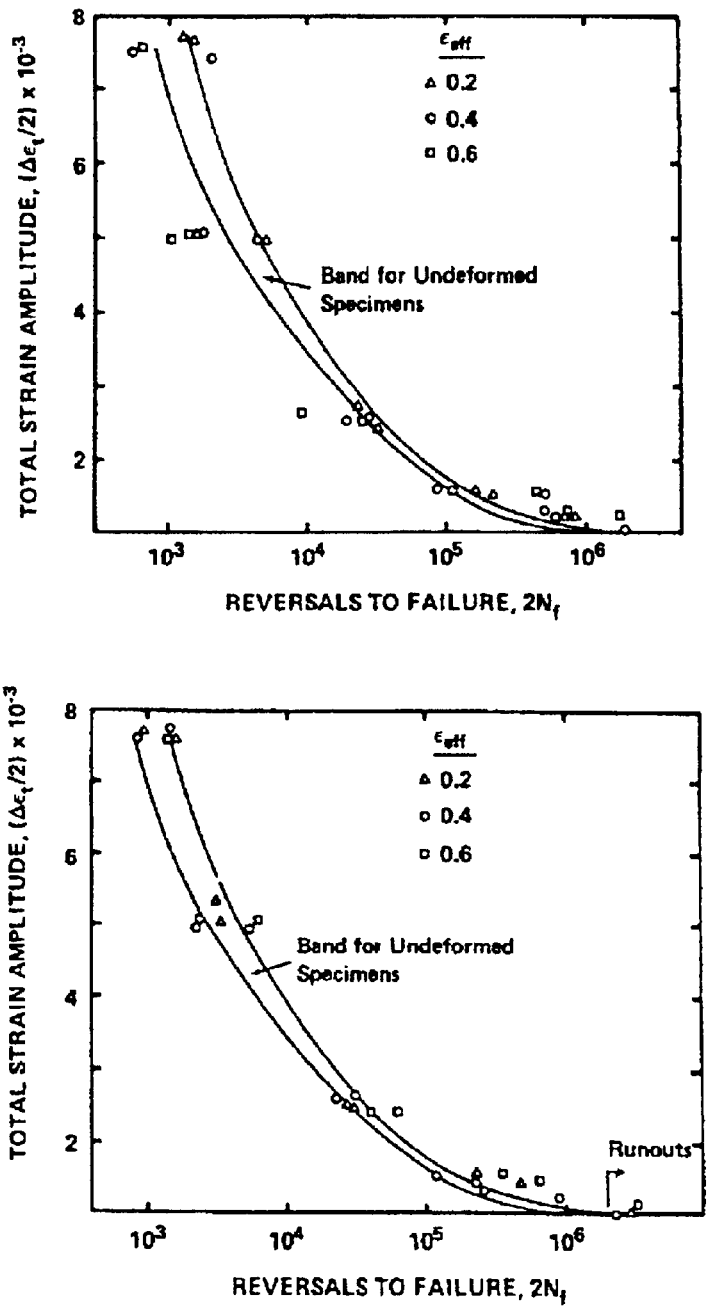
Figure 23:
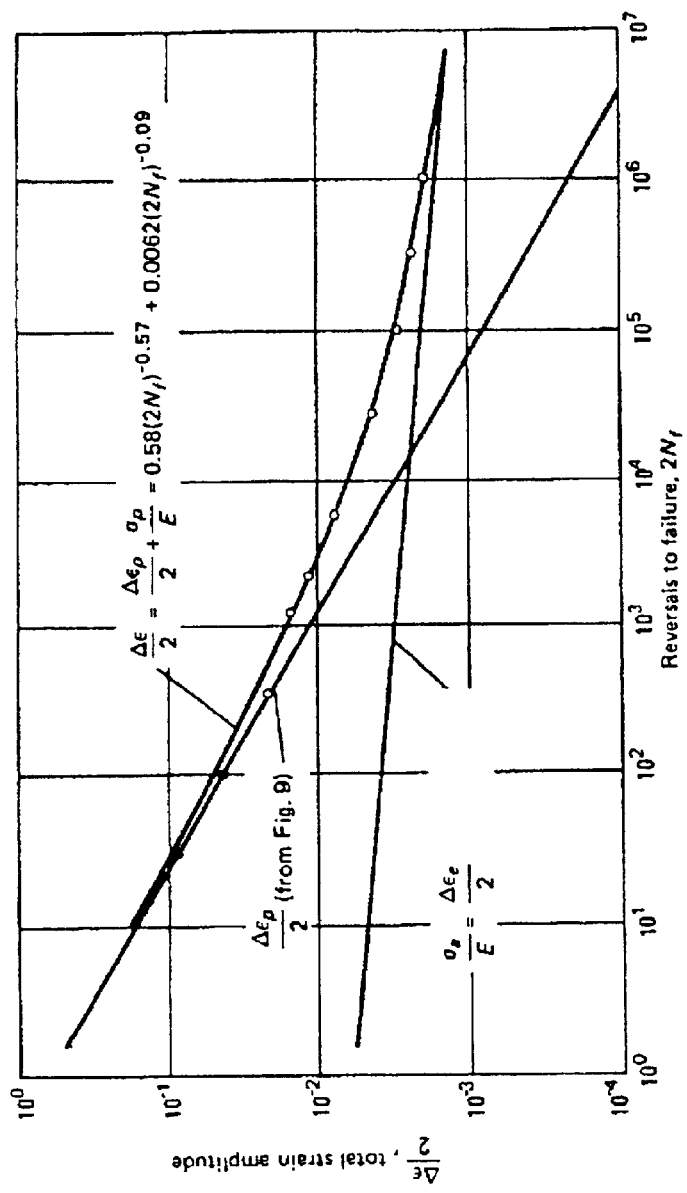
Figure 24:
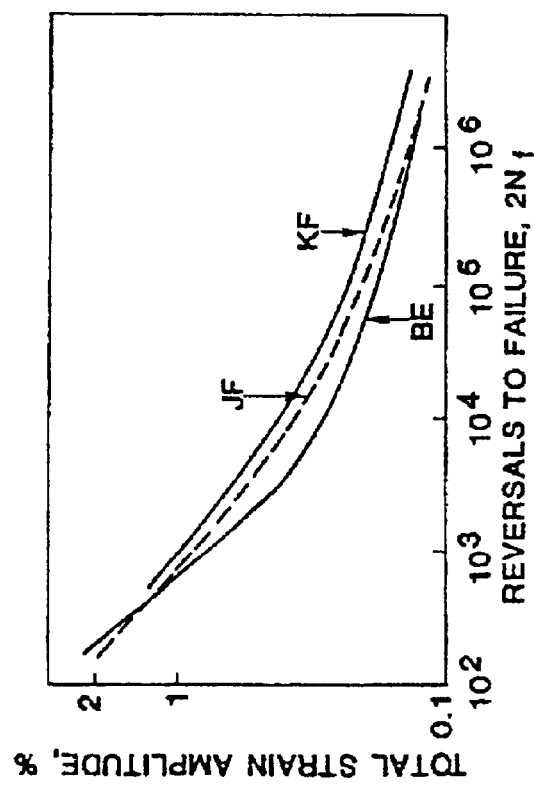
Figure 25:
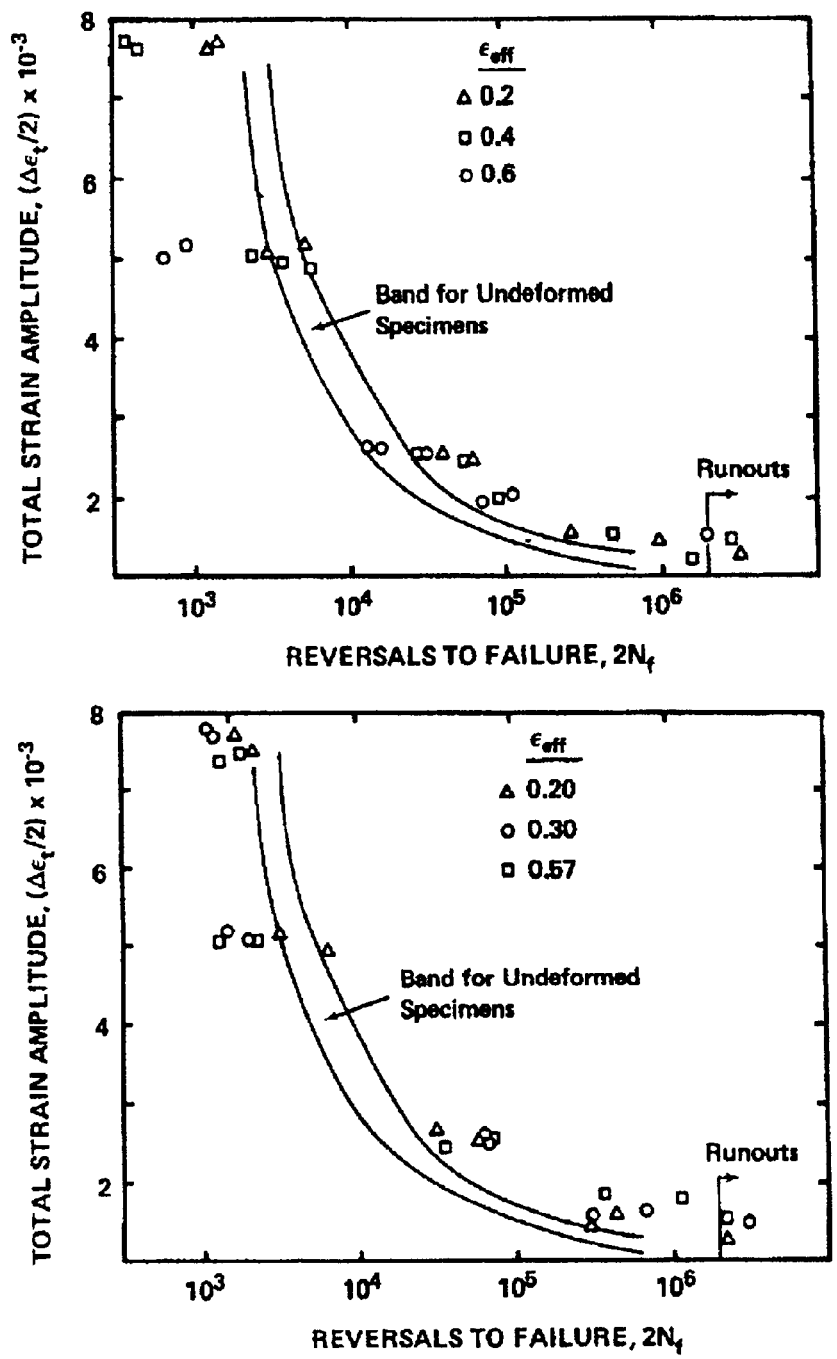
Figure 26:
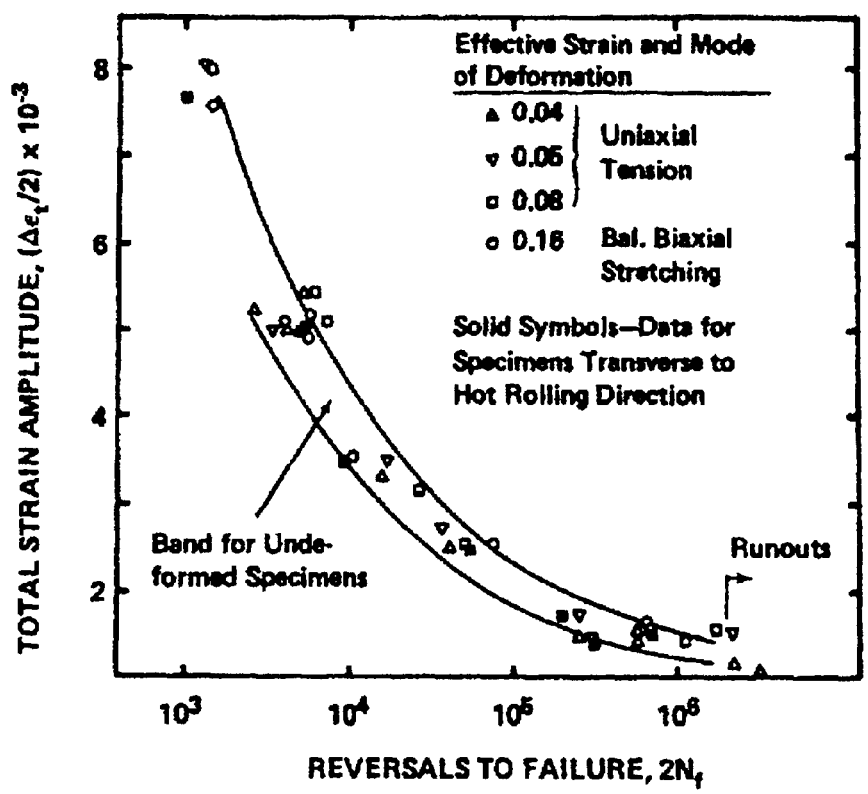

Examination of FIG. 18 shows that, like the elastic model, decreases in aspect ratio lead to larger reversed plastic strain values, with minor differences between inward and outward wrinkles. FIG. 19 shows that circumferential extent has little impact on larger aspect ratios such as 9; however, for an aspect ratios of 6, reversed plastic strain increases significantly with increased circumferential extent. FIG. 19 also demonstrates that inward wrinkles have higher reversed plastic strain than outward wrinkles at smaller aspect ratios. FIG. 20 shows that reversed plastic strain decreases with increasing wrinkle height for larger aspect ratios such as 9 and 7.5; however, an aspect ratio of 6 produces increasing reversed plastic strain with increased wrinkle height. Unlike the elastic model, the effect of the wrinkle geometry (local wall crippling) on the bending deflection of the pipe is clearly shown in the elastic-plastic models, with the maximum deflection increasing significantly as the wrinkles become sharper. FIG. 21 shows that the maximum bend deflection for loaded conditions increases significantly as the aspect ratio decreases.

Tables 5 and 6 show that the Swanson Creek failure geometry is a significant outlier relative to the parametric variations considered. The deflections for the Swanson Creek geometry are significantly higher than the most limiting of the parametric cases considered in these analyses. The Swanson Creek geometry case is also a significant outlier when reversing plastic strain is considered. Whereas the parametric cases considered tend to have some reversing plastic strain at the wrinkle center on the pipe ID or OD (depending on whether the wrinkle is inward or outward), with little to none elsewhere, the Swanson Creek failure geometry case has substantial reversing plastic strain at the wall ID and OD at both the center and edge of the wrinkle.

Wrinkle Acceptance Criteria

Based on the metallurgical analysis documented in (Reference 24) and more fully discussed in (Reference 21), the failure that occurred at Swanson Creek is characterized as crack formation and propagation by low cycle fatigue with a ductile tearing final failure surface. Therefore, it is reasonable to assume that other failures for this pipeline will also be fatigue based; this assumption is also discussed in greater detail in (Reference 21).

Currently, there are no defined limits of acceptability for local wrinkle deformations at the intrados of a pipe bend. The finite element analysis results provided in this section may be used to demonstrate that certain wrinkle geometries in the Piney Point pipeline are acceptable for continued service.

Based on the results of the finite element analysis, acceptance criteria for continued use can be formulated. There are two considerations that must be addressed by the acceptance criteria: (1) the wrinkle geometry must be stable so that it does not become more severe as it is cycles and (2) the cyclic stresses and strains in the wrinkle must be consistent with a fatigue life greater than the service cycles experienced from the beginning of operation until the next time the wrinkle will be evaluated (following the next in-line inspection to be performed in 2001). Stability of the wrinkle geometry is considered to be demonstrated by the elastic-plastic FEA for all cases where the reverse plastic strain occurs in only one or two small regions and does not extend through the pipe wall thickness. For all cases in the parametric elastic-plastic analyses with aspect ratios greater than 6, the reverse plasticity occurs on only one side of the pipe wall at the center of the wrinkle and, for a few cases, on one side of the pipe wall at the wrinkle edge. Therefore, wrinkles with aspect ratios greater than 6 are considered to be geometrically stable.

The fatigue lives for wrinkles are evaluated using two approaches: (1) comparing total strain amplitudes calculated by the elastic-plastic model to published low-cycle fatigue data, and (2) applying the fatigue design curve from the ASME Code, Section III using the elastic analyses results.

The effect of a local geometric discontinuity (such as a corrosion pit) on the surface of a wrinkle is not explicitly considered in the finite element model, but may be described as follows. As noted above, the potential failure mechanism for a wrinkle in the Piney Point oil pipeline is low cycle fatigue, where the crack life is dominated by growth and not initiation. A corrosion pit would tend to shorten the small number (relative to the total crack life) of cycles to crack initiation but would not have a significant accelerating effect on the crack growth phase.

8. Fatigue Life Based on Elastic-Plastic Analyses

Because the failure mechanism for the Piney Point pipeline is fatigue based, a method that may be used to provide a measure for the acceptability of wrinkles uses published experimental data relating reversing strain to reversals to failure as a basis. FIGS. 22 through 27 are experimental fatigue data contained in (Reference 25) for various carbon and high strength low alloy steels. The data are presented as plots of reversing strain amplitude (typically total strain amplitude) versus the number of reversals to failure at that strain amplitude. Examination of the figures reveals that fatigue life as a function of strain amplitude does not differ greatly for the various carbon and low alloy steels represented. Therefore, these fatigue data are also considered applicable to the API X42 steel used in the Piney Point pipeline. FIGS. 15 through 19 show actual test results of fatigue cycles to failure. Therefore, the data indicate more cycles to failure than would be given by a design curve such as the ASME Code curve.

Turning to Tables 5 and 6, a bounding value for reversing plastic strain of a wrinkle with an aspect ratio of 7.5 may be selected as 0.0052. This value is converted to total strain range by adding the amount of reversing elastic strain, or 2×0.0027 (80,000 psi calculated equivalent stress divided by an E of 30×10$^3$ psi)=0.0054. Therefore, the total strain range for this aspect ratio is 0.0106, which is then divided by two to calculate a total strain amplitude of 0.0053, or 5.3×10$^{-3}$. The data contained in FIGS. 15 through 19 show that, for this amount of total strain amplitude, the number of reversals to failure is no less than approximately 5,000 reversals (2,500 total cycles) which is more than ten times the number of operational cycles experienced to date by the pipeline.

A similar calculation can be performed for the Swanson Creek geometry results to assess the reasonableness of this evaluation. Table 5 shows the reversing plastic strain for this case to be 0.0271, which is added with the reversing elastic strain of 0.0054 to give a total strain range of 0.0325 and a total strain amplitude of 0.016, or 1.6×10$^{-2}$. For many of the experimental data plots, this level of strain amplitude is not charted, signifying the number of reversals to failure is significantly less than the minimum plotted 1,000 reversals. The two plots that do contain data with this amount of strain amplitude show the number of reversals to failure to be approximately 400 reversals (200 cycles). This is reasonably close to the estimated 150 cycles required to cause the failure at Swanson Creek. It is also noted that the 2,500 cycles to failure determined for an acceptable wrinkle geometry (aspect ratio of 7.5) is more than ten times the number of cycles to failure determined for the Swanson Creek geometry.

9. ASME Boiler and Pressure Vessel Code Design Fatigue Rules

Another fatigue-based method that may be used to provide a measure for the acceptability of wrinkles uses the ASME Boiler and Pressure Vessel Code Section III Class I fatigue rules as a basis. The ASME Code presents a fatigue design curve for steel. This design curve is conservative and bounding for experimental data. Therefore, the use of the design curve provides significant margin in the acceptance criteria.

According to the ASME Code rules, the maximum alternating stress intensity is determined from an elastic analysis of the component; this alternating stress intensity is then used to determine an allowable number of cycles for a given loading scenario. Using the elastic model, stress intensity results were recorded for a more limited number of parametric variations; based on earlier model results, the circumferential extent was limited to 180° and aspect ratios of 6, 7.5, 9, and 12 were analyzed. The maximum stress intensity under loading was determined for these cases, and the number of allowable fatigue cycles was determined using the values in Table I-9.1 of the Code. For comparison purposes, the Swanson Creek failure geometry was also analyzed and the number of allowable cycles calculated. Using these rules as a basis for acceptance criteria, any configuration that has a design fatigue life greater than the estimated 150 operation cycles the pipeline has experienced to date is acceptable to be returned to service without modification.

Table 7 is a summary of the ASME Code allowable fatigue cycles for various wrinkle geometries. Examination of Table 7 shows that inward wrinkles have slightly lower allowable design fatigue lives than an outward wrinkle with the same aspect ratio. For outward wrinkles, the most limiting cases for aspect ratios as low as 6 have fatigue lives well in excess of the estimated 150 pipeline operation cycles. For inward wrinkles, the most limiting cases for aspect ratios as low as 7.5 have fatigue lives greater than the estimated 150 operation cycles. Therefore, a global acceptance criterion for wrinkles can be set at an aspect ratio of 7.5; i.e., any wrinkle with an aspect ratio of 7.5 or greater (and a circumferential extent of 180° or less) is acceptable for continued service.

It should be noted that the Piney Point pipeline has operated on average 5 to 10 times per year; therefore, even a geometry with a design fatigue life of 180 cycles would require another 3 to 6 years before its design fatigue life is reached. Table 7 also reveals that the Swanson Creek failure geometry has a design fatigue life of 90 cycles, or 60% of the estimated 150 cycles. This is further indication that this method of wrinkle assessment is conservative and reasonable.

In summary, the above work shows that reasonable and conservative continued service acceptance criteria for a local wrinkle at the intrados of a bend on the Piney Point pipeline may be determined. The acceptance criteria are set by wrinkle aspect ratio and wrinkle circumferential extent. The above work shows that any wrinkle with an aspect ratio of 7.5 or greater and a circumferential extent of 180° or less is acceptable for immediate return to service.

Repair Methods

Wrinkle anomalies in SEMA's (formerly PEPCO's) 12-inch and 16-inch hot oil pipelines that do not pass the acceptance criterion can be repaired by either one of the following methods: Cut outs and Epoxy-filled shells.

Cut outs and replacements can be done if the pipelines are out of service and drained-up. A cylinder of the anomaly-affected pipe is removed and replaced with a new piece of pipe. Enough pipe must be stripped of cover to allow sufficient flexibility at both ends of the pipeline for tying in the new piece without inducing significant stress into the pipeline.

Epoxy-filled shells can be used to repair wrinkle anomalies. An epoxy-filled shell comprises of a concentric steel sleeve made of two half-cylinders welded or bolted together around an anomaly-affected region of the pipeline with an inside diameter ¼ to 1-½ inches greater than the outside diameter of the pipeline. The shell is adjusted to fit concentrically around the pipe so that a reasonably uniform-thickness annular space exists. The ends of the shell are plugged with a quick-setting epoxy trowelled in place and the annular space is then pumped full of liquid epoxy resin. The entire annular space is allowed to fill. When the epoxy hardens, the anomaly beneath the shell is immobilized and it cannot undergo the further strain that would be necessary to cause it to fail. This technique is particularly well suited for repairing wrinkles because the annular space accommodates the radial protrusion, if any, of the wrinkle and it prevents further straining of the wrinkle.

The standard epoxy is adequate for operating temperatures up to 140° F. It is believed that a higher temperature epoxy (>160° F.) can be obtained within 6 weeks if necessary. Because the ends of the shell are not welded to the pipe, there is no chance for the stress-concentrating effect and metallurgical changes that accompany sleeve-end fillet welds to create potential problems.

Type-B sleeves ostensibly could be used to repair wrinkle anomalies if a stand-off configuration were to be used. This concept embodies fillet welding two steel rings of suitable thicknesses to the carrier pipe, one upstream and one downstream from a wrinkle anomaly. A bridging sleeve comprised of two half-cylinders joined longitudinally by welding is fillet welded to each of the two rings creating an annular space sufficient to accommodate any radial protrusion of the wrinkle. The stand-off sleeve must be and would be designed to the same pressure-carrying capacity as the carrier pipe. If the anomaly should ever develop a leak, the sleeve would become the pressure boundary. Alternatively, the sleeve can be pressurized intentionally by hot tapping through the sleeve and the carrier pipe. Pressurization of the annular space would relieve hoop stress on the anomaly. As a third possibility, the annular space could be filled with epoxy to immobilize the anomaly. In this case, it would not be necessary to fillet weld the first layer rings to the carrier pipe. The fillet welds create a stress-concentrating effect and metallurgical chances, and thereby a very small risk of a new mode of failure is created. Because of this slight increase in risk over an epoxy-filled shell and because it offers no real advantage over the shell, the Type-B sleeve concept is not recommended.

A "pumpkin" sleeve is a forged stand-off sleeve that has an enlarged-diameter central span to accommodate the radial protrusion, if any, of a wrinkle anomaly, but its ends are swaged down to fit the carrier pipe for the purpose of fillet welding the ends. The pumpkin must and would be designed to have the same pressure-carrying capacity as the carrier pipe. The pumpkin can function in the same ways as a stand-off Type-B sleeve. It can be pressurized if its ends are fillet welded to the carrier pipe, or it can be filled with epoxy in which case its ends need not be fillet welded to the carrier pipe. The pumpkin concept is not recommended because it has the same disadvantage as the Type-B sleeve.

A composite wrap (ClockSpring™ or Armor Plate) ostensibly could be used to repair a pipe containing a wrinkle anomaly. A single-width wrap could be used with sufficient hardenable grout to fill all radial gaps, or combination of wraps would be used. In the latter embodiment, single-width wraps are placed upstream and downstream from the anomaly, the annular space is filled with grout, and a third single-width wrap forms a bridge between the two first-layer wraps. The three-wrap configuration is believed to be more effective than the singlewrap configuration. The standard ClockSpring™ wraps and filler are said to be adequate for temperatures up to 140° F. A higher temperature configuration may be available. A higher temperature Armor-Plate configuration is said to be available. Composite-wrap repairs of this type are intended to immobilize the wrinkle anomaly. Because of the lower effective stiffnesses of these systems compared to steel sleeves, pumpkins, or the epoxy-filled shell, and the fact that they offer little or no strengthening in the longitudinal direction, it is believed that composite wraps do not offer a viable means of repair for wrinkled segments of pipe.

The following references are cited in this application:

(1) Bernstein, J., Materials Laboratory Factual Report, Pepco Chalk Point Pipeline Rupture, DCA00-MP006, National Transportation Safety Board (Jun. 19, 2000).
(2) Bouwkamp, G. J. and Stephen, R. M., "Large Diameter Pipe Under Combined Loading", *Transportation Engineering Journal*, ASCE (August 1973).
(3) Olson, R., Clark, T., and Odom, T., "Evaluation of the Structural Integrity of Cold FieldBent Line Pipe", *Ninth Symposium on Pipeline Research*, PRC International (1996).
(4) Peng, L., "Stress Analysis Methods for Underground Pipe Lines", *Pipe Line Industry*, "Part 1, Basic Calculations", pp 67–71 (April 1978), and "Part II, Soil-Pipe Interaction", pp 65–73 (May 1978).
(5) Fekete, L. A., "Structural Design of Pipe Lines Subject to Temperature Change", *Pipe Line Industry*, Part 1, pp 57–59 (August 1974), Part 2, pp 50–55 (September 1974).
(6) Karge, F., "Stresses in Buried Pipe Lines", *The Petroleum Engineer*, pp D-42 to D-46 (October 1952).
(7) McClure, G. M. and Jackson, L. R., "Slack in Buried Gas Pipe Lines", *Oil and Gas Journal* (Mar. 22, 1951).
(8) Ligon, J. B. and Mayer, G. R., "Friction Resistance of Buried Pipeline Coatings Studied", *Pipeline and Gas Journal*, pp 33–36 (February 1971).
(9) Schnackenberg, P. J., "How to Calculate Stress in Above/Below Ground Transition", *Pipe Line Industry*, pp 53–57 (November 1976).
(10) Wilbur, W. E., "Analyzing Pipe Line Stresses", *Pipe Line Industry*, pp 25–31 (February 1963).
(11) Yen, G. C., Tsao, C. H., and Hinkle, R. D., "Soil-Pipe Interaction of Heated Oil Pipelines", *Transportation Engineering Journal*, ASCE (January 1981).
(12) Syed, A., McMickle, R. W., and Brassow, C. L., "Soil-Pipe Interaction and Pipeline Design", *Transportation Engineering Journal*, ASCE (January 1981).
(13) Luscher, V., Thomas, H. P., and Maple, J. A., "Pipe-Soil Interaction, Trans-Alaska Pipeline", *Proceedings of ASCE Conference on Pipelines in Adverse Environments*, pp 486–502 (January 1979).
(14) Joodi, P. M. H., "Simplified Thermal Analysis for Embedded Piping", ASME, *Computers in Engineering* (1992).
(15) Kellner, J. D., "Laboratory Evaluation of the Effects of Soil Stress on Anti-Corrosion Pipeline Coatings" (no date or publication information).
(16) Qiang Kang, C., and YingMin, L., "The Effects of Various Parameters on Thermal Stresses in the Pipe Bends of Underground Pipelines", *International Meeting on Petroleum Engineering* (no date or publication information).
(17) Hetenyi, M., "Beams on Elastic Foundation" (1946).
(18) Timoshenko, S. P. and Gere, J. M., *Theory of Elastic Stability*, Second Edition (1961).
(19) Arav, F., "Evaluation of Pipe Bends Having Local Corrugations," *Third International Conference on Pressure Vessel Technology*, Part 1, Analysis, Design, and Inspection (1977).
(20) ASME Boiler and Pressure Vessel Code, Section VIII, Div. 2.
(21) Turner, A., "Evaluation of Risks Associated with Wrinkle Bends in Buried Pipelines," January 2001.
(22) ASME Boiler and Pressure Vessel Code, Section III, Nuclear Vessels, 1998 Edition with Addenda through Summer 2000.
(23) "ANSYS Engineering Analysis System," Revision 5.6, ANSYS, Inc.
(24) Bernstein, J., Materials Laboratory Factual Report No. 00-069, National Transportation Safety Board Office of Research and Engineering, November 2000.
(25) Boyer, H., "Atlas of Fatigue Curves," American Society for Metals, 1986.

While the invention has been disclosed in its preferred forms, it will be apparent to those skilled in the art that many modifications, additions, and deletions can be made therein without departing from the spirit and scope of the invention and its equivalents, as set forth in the following claims.

TABLE 1

| Reference No. | Coefficients of Friction, $\mu$ | Friction Force, f, lb/ft | Passive Soil Force, U, lb/ft | Coefficient of Subgrade Reaction, K, lb/in$^2$ | Active Length, L, feet | Movement at Free End, Y, inches | Thrust Force on Unyielding Anchor, F, lb |
|---|---|---|---|---|---|---|---|
| 4 | Silt 0.3 Sand 0.4 Gravel 0.5 | $\mu(\gamma HD/6 + W_p)$ | $\frac{\gamma}{2}\left(H + \frac{D}{12}\right)^2 \tan^2\left(45 + \frac{\varphi}{2}\right)$ | $0.2315\delta\left(H + \frac{D}{12}\right)\tan^2\left(45 + \frac{\varphi}{2}\right)$ | $F/f$ | $\dfrac{6F^2}{AEf}$ | $F = A\left(S_L + \dfrac{S_h}{2}\right)$ |
| 5 | 0.4 to 0.5 | $\mu(\gamma H\pi D/12)$ | | | $F'/f$ | $\dfrac{6F'^2}{AEf}$ | $F' = A(S_L)$ |

TABLE 1-continued

| Reference No. | Coefficients of Friction, $\mu$ | Friction Force, f, lb/ft | Passive Soil Force, U, lb/ft | Coefficient of Subgrade Reaction, K, lb/in² | Active Length, L, feet | Movement at Free End, Y, inches | Thrust Force on Unyielding Anchor, F, lb |
|---|---|---|---|---|---|---|---|
| 6 | 0.4 | $\mu(0.85\gamma B^2)$ | | | F''/f | | F'' = A(E $\varphi$ $\Delta$T) |
| 7 | | | | | | | |
| 8 | 0.59 to 0.91 Coal tar 0.51 to 0.71 FBE | $\mu(\gamma HD/6 + W_p)$ | | | | | |
| 9 | | $80\left(\dfrac{D}{12}\right)^2$ | | | F/f | $\dfrac{6F^2}{AEf}$ | $F = A\left(S_L + \dfrac{S_h}{2}\right)$ |
| 10 | | $80\left(\dfrac{D}{12}\right)^2$ | | | | | $F = A\left(S_L + \dfrac{S_h}{2}\right)$ |
| 12 | | | | | F/f | $\dfrac{6F^2}{AEf}$ | $F = A\left(S_L + \dfrac{S_h}{2}\right)$ |
| 13 | Tangent of soil-pipe friction angle | $k_{av} = \left[\gamma H + \dfrac{D}{24}\left(\dfrac{\pi D}{12}\right)\right]\tan\delta \quad \dfrac{\gamma}{2}\left(H + \dfrac{D}{12}\right)^2 \tan^2\!\left(45 + \dfrac{\varphi}{2}\right)$ | | | F/f | $\dfrac{6F^2}{AEf}$ | $F = A\left(S_L + \dfrac{S_h}{2}\right)$ |
| 14 | | $\mu\!\left(\dfrac{\gamma H\pi D}{12}\right)$ | | | | | |
| 15 | 0.33 bare 0.31 to 0.47 tape 0.38 to 0.45 FBE 0.62 to 0.83 coal tar | | | | | | |

TABLE 2

Forces, Active Lengths, and Displacements for the Piney Point Pipeline

| | Equation 4 Thrust Force, F, lb | Equation 7 Friction Force, f, lb/ft | Equation 7 Reference 6 Variation, lb/ft | Equation 8 Friction Force, f, lb/ft | Equation 8 Reference 13 Variation, lb/ft | Equation 9 Friction Force, lb/ft | Equation 5 Active Length, L, feet | Equation 6 Free-End Movement, y, inches |
|---|---|---|---|---|---|---|---|---|
| 12.75-inch OD by 0.203-inch w.t. X42 P = 400 psig $\Delta$T = 110° F. $W_p$ = 72.9 lb/ft | 194,843 | 260.9 | 452.0 | 375.5 | 442.0 | 90.3 | 746.8 | 3.58 |
| 16-inch OD by 0.219-inch w.t. X42 P = 400 psig $\Delta$T = 110° F. $W_p$ = 108.8 lb/ft | 268,295 | 332.6 | 578.5 | 471.2 | 499.2 | 142.2 | 806.7 | 3.93 |

All cases except Reference-13 variation $\mu$ = 0.3.
$\mu$ = tan $\gamma$ tan 20° = 0.36 for Reference-13 variation.
All cases use depth of cover, H, equal to 3 feet. Reference-6 variation B = (D + 12)/12.
All cases use unit weight of soil, $\gamma$, equal to 125 lb/ft³.

$$W_p = \frac{488\pi Dt}{144} + 0.82(62.4)\pi\left(\frac{D}{24}\right)^2,$$

0.82 is the assumed sp. gr. of oil.
Active lengths calculated using Equation-7 definition of f.

TABLE 3

Uplift Resistance, Passive Lateral Resistance and Straight Pipe Buckling Piney Point Pipeline

| | Equation 10 Uplift Resistance, $R_u$, lb/ft | Equation 11 Passive Lateral Resistance, $R_p$, lb/ft | Equation 12 Coefficient of Subgrade Reaction, K, lb/in² | Equation 13 Axial Buckling Load, $N_{cr}$, lb | Equation 14 Euler Buckling Length, l, inches | $\dfrac{l}{\bar{r}}$ | Equation 15 Axial Load for Uplift Buckling $P_u$, lb |
|---|---|---|---|---|---|---|---|
| 12.75-inch OD by 0.203-inch w.t. X42<br>P = 400 psig<br>ΔT = 110° F.<br>$W_p$ = 72.9 lb/ft<br>A = 8.13 in²<br>I = 165.23 in⁴ | 471.3 | 3,094 | 352.7 | 2,644,465 | 501 | 111 | 1,193,456 |
| 16-inch OD by 0.219-inch w.t. X42<br>P = 400 psig<br>ΔT = 110° F.<br>$W_p$ = 108.8 lb/ft<br>A = 11.01 in²<br>I = 352.26 in⁴ | 608.7 | 3,521 | 376.2 | 3,987,785 | 623 | 110 | 2,260,094 |

All cases use depth of cover, H, equal to 3 feet and unit weight of soil, γ, equal to 125 lb/ft³.

$$W_p = \frac{488\pi Dt}{144} + 0.82(62.4)\pi\left(\frac{D}{24}\right)^2,$$

0.82 is the assumed sp. gr. of oil.
Radius of gyration, $$\bar{r} = \sqrt{I/A}.$$

TABLE 4

Elastic Material Properties Analysis Results - Leg Length Tuned for 3.0 inches Displacement

| | | | | | Buckle Center | | Buckle Edge | | Free |
|---|---|---|---|---|---|---|---|---|---|
| Case | Pipe Dia (in) | Buckle Ht Pct. Wall | Circum. Ang. | l/h | ID Min. Axial (psi) | OD Max. Axial (psi) | ID Max. Axial (psi) | OD Min. Axial (psi) | Deflection (in) |
| 1 | 12.75 | 100% | 90 | 12 | −183,650 | 77,865 | 38,509 | −149,302 | 2.901 |
| 2 | 12.75 | 150% | 90 | 12 | −169,849 | 67,061 | 48,767 | −153,614 | 2.910 |
| 3 | 12.75 | 200% | 90 | 12 | −146,653 | 45,175 | 25,320 | −128,761 | 2.917 |
| 4 | 12.75 | 300% | 90 | 12 | −103,602 | 6,874 | 14,220 | −93,219 | 2.924 |
| 5 | 12.75 | 600% | 90 | 12 | −57,920 | 6,591 | 14,504 | −81,760 | 2.925 |
| 6 | 12.75 | 100% | 180 | 12 | −208,614 | 91,255 | 43,275 | −162,032 | 2.910 |
| 7 | 12.75 | 150% | 180 | 12 | −194,834 | 81,794 | 54,157 | −167,809 | 2.926 |
| 8 | 12.75 | 200% | 180 | 12 | −168,243 | 57,846 | 25,444 | −136,828 | 2.936 |
| 9 | 12.75 | 300% | 180 | 12 | −118,183 | 11,022 | 13,939 | −92,068 | 2.945 |
| 10 | 12.75 | 600% | 180 | 12 | −63,551 | 5,959 | 13,670 | −77,749 | 2.941 |
| 11 | 12.75 | 100% | 270 | 12 | −217,599 | 96,331 | 44,425 | −166,265 | 2.914 |
| 12 | 12.75 | 150% | 270 | 12 | −203,094 | 86,890 | 54,795 | −171,955 | 2.933 |
| 13 | 12.75 | 200% | 270 | 12 | −174,325 | 61,646 | 23,335 | −138,129 | 2.945 |
| 14 | 12.75 | 300% | 270 | 12 | −120,741 | 12,661 | 13,667 | −90,014 | 2.952 |
| 15 | 12.75 | 600% | 270 | 12 | −63,513 | 4,783 | 13,007 | −75,158 | 2.939 |
| 16 | 12.75 | 100% | 90 | 9 | −214,938 | 106,214 | 41,914 | −148,916 | 2.901 |
| 17 | 12.75 | 150% | 90 | 9 | −213,909 | 108,892 | 57,631 | −154,085 | 2.913 |
| 18 | 12.75 | 200% | 90 | 9 | −198,677 | 97,112 | 79,934 | −169,019 | 2.925 |
| 19 | 12.75 | 300% | 90 | 9 | −157,152 | 59,967 | 31,826 | −118,763 | 2.943 |
| 20 | 12.75 | 600% | 90 | 9 | −79,406 | 6,281 | 42,117 | −119,180 | 2.965 |
| 21 | 12.75 | 100% | 180 | 9 | −245,056 | 123,362 | 46,332 | −162,856 | 2.910 |
| 22 | 12.75 | 150% | 180 | 9 | −248,374 | 131,812 | 64,511 | −172,557 | 2.932 |
| 23 | 12.75 | 200% | 180 | 9 | −231,890 | 119,898 | 87,908 | −190,393 | 2.953 |
| 24 | 12.75 | 300% | 180 | 9 | −181,850 | 75,864 | 25,618 | −123,028 | 2.981 |
| 25 | 12.75 | 600% | 180 | 9 | −88,960 | 5,842 | 32,242 | −118,945 | 3.005 |
| 26 | 12.75 | 100% | 270 | 9 | −256,157 | 130,065 | 47,502 | −167,747 | 2.915 |
| 27 | 12.75 | 150% | 270 | 9 | −260,578 | 140,370 | 65,878 | −178,636 | 2.942 |
| 28 | 12.75 | 200% | 270 | 9 | −242,496 | 127,639 | 88,929 | −197,035 | 2.967 |
| 29 | 12.75 | 300% | 270 | 9 | −186,972 | 79,562 | 19,392 | −122,759 | 2.996 |
| 30 | 12.75 | 600% | 270 | 9 | −87,613 | 5,136 | 22,219 | −116,038 | 3.006 |
| 31 | 12.75 | 100% | 90 | 6 | −254,404 | 135,331 | 34,933 | −139,094 | 2.900 |

TABLE 4-continued

Elastic Material Properties Analysis Results - Leg Length Tuned for 3.0 inches Displacement

| Case | Pipe Dia (in) | Buckle Ht Pct. Wall | Circum. Ang. | l/h | Buckle Center ID Min. Axial (psi) | Buckle Center OD Max. Axial (psi) | Buckle Edge ID Max. Axial (psi) | Buckle Edge OD Min. Axial (psi) | Free Deflection (in) |
|---|---|---|---|---|---|---|---|---|---|
| 32 | 12.75 | 150% | 90 | 6 | −270,571 | 149,872 | 82,769 | −175,530 | 2.914 |
| 33 | 12.75 | 200% | 90 | 6 | −266,868 | 151,765 | 110,414 | −196,338 | 2.930 |
| 34 | 12.75 | 300% | 90 | 6 | −240,195 | 138,733 | 122,650 | −193,397 | 2.963 |
| 35 | 12.75 | 600% | 90 | 6 | −146,905 | 63,726 | 47,195 | −114,552 | 3.032 |
| 36 | 12.75 | 100% | 180 | 6 | −288,992 | 156,054 | 38,205 | −152,811 | 2.909 |
| 37 | 12.75 | 150% | 180 | 6 | −315,985 | 183,615 | 94,267 | −199,500 | 2.935 |
| 38 | 12.75 | 200% | 180 | 6 | −317,869 | 193,620 | 128,457 | −228,167 | 2.968 |
| 39 | 12.75 | 300% | 180 | 6 | −288,753 | 179,087 | 140,048 | −226,576 | 3.031 |
| 40 | 12.75 | 600% | 180 | 6 | −166,726 | 76,779 | 27,868 | −103,253 | 3.136 |
| 41 | 12.75 | 100% | 270 | 6 | −302,067 | 164,472 | 39,096 | −157,882 | 2.913 |
| 42 | 12.75 | 150% | 270 | 6 | −333,315 | 197,336 | 98,209 | −208,170 | 2.947 |
| 43 | 12.75 | 200% | 270 | 6 | −336,721 | 208,619 | 134,610 | −239,454 | 2.987 |
| 44 | 12.75 | 300% | 270 | 6 | −303,895 | 191,234 | 143,862 | −236,512 | 3.062 |
| 45 | 12.75 | 600% | 270 | 6 | −164,251 | 75,411 | 14,725 | −93,726 | 3.155 |
| 46 | 12.75 | 100% | 90 | 3 | −291,289 | 202,703 | 35,099 | −140,422 | 2.897 |
| 47 | 12.75 | 150% | 90 | 3 | −334,718 | 203,500 | 90,395 | −170,524 | 2.911 |
| 48 | 12.75 | 200% | 90 | 3 | −348,377 | 216,605 | 105,556 | −190,441 | 2.929 |
| 49 | 12.75 | 300% | 90 | 3 | −356,331 | 219,985 | 145,041 | −221,506 | 2.971 |
| 50 | 12.75 | 600% | 90 | 3 | −284,725 | 203,486 | 149,597 | −234,420 | 3.095 |
| 51 | 12.75 | 100% | 180 | 3 | −322,070 | 229,644 | 33,977 | −151,955 | 2.903 |
| 52 | 12.75 | 150% | 180 | 3 | −378,420 | 244,822 | 106,044 | −196,459 | 2.931 |
| 53 | 12.75 | 200% | 180 | 3 | −412,322 | 263,452 | 131,635 | −227,221 | 2.970 |
| 54 | 12.75 | 300% | 180 | 3 | −436,598 | 289,065 | 199,590 | −283,912 | 3.072 |
| 55 | 12.75 | 600% | 180 | 3 | −379,869 | 270,526 | 218,398 | −295,603 | 3.402 |
| 56 | 12.75 | 100% | 270 | 3 | −334,076 | 240,529 | 33,501 | −156,446 | 2.907 |
| 57 | 12.75 | 150% | 270 | 3 | −397,072 | 261,892 | 112,588 | −207,416 | 2.942 |
| 58 | 12.75 | 200% | 270 | 3 | −440,645 | 283,558 | 142,980 | −242,889 | 2.994 |
| 59 | 12.75 | 300% | 270 | 3 | −465,454 | 310,654 | 222,635 | −308,426 | 3.129 |
| 60 | 12.75 | 600% | 270 | 3 | −383,532 | 277,075 | 230,026 | −300,174 | 3.541 |
| 61 | 16 | 100% | 90 | 12 | −186,017 | 86,559 | 40,689 | −145,652 | 2.939 |
| 62 | 16 | 150% | 90 | 12 | −176,879 | 79,672 | 52,146 | −150,703 | 2.949 |
| 63 | 16 | 200% | 90 | 12 | −156,499 | 60,480 | 22,081 | −119,248 | 2.958 |
| 64 | 16 | 300% | 90 | 12 | −113,781 | 19,066 | 25,475 | −118,933 | 2.968 |
| 65 | 16 | 600% | 90 | 12 | −60,828 | 4,184 | 11,064 | −90,535 | 2.976 |
| 66 | 16 | 100% | 180 | 12 | −210,814 | 100,016 | 44,731 | −157,722 | 2.948 |
| 67 | 18 | 150% | 180 | 12 | −202,432 | 95,056 | 57,273 | −164,842 | 2.966 |
| 68 | 16 | 200% | 180 | 12 | −178,946 | 73,916 | 21,175 | −126,856 | 2.980 |
| 69 | 16 | 300% | 180 | 12 | −128,966 | 26,681 | 20,561 | −122,581 | 2.992 |
| 70 | 16 | 600% | 180 | 12 | −66,995 | 3,962 | 10,334 | −87,483 | 2.996 |
| 71 | 16 | 100% | 270 | 12 | −220,455 | 105,099 | 45,769 | −161,814 | 2.952 |
| 72 | 16 | 150% | 270 | 12 | −210,992 | 100,419 | 58,069 | −169,154 | 2.974 |
| 73 | 16 | 200% | 270 | 12 | −185,467 | 77,960 | 18,970 | −128,175 | 2.990 |
| 74 | 16 | 300% | 270 | 12 | −131,653 | 28,133 | 15,876 | −121,602 | 3.001 |
| 75 | 16 | 600% | 270 | 12 | −66,702 | 3,029 | 9,670 | −84,678 | 2.993 |
| 76 | 16 | 100% | 90 | 9 | −215,440 | 114,751 | 42,671 | −144,486 | 2.939 |
| 77 | 16 | 150% | 90 | 9 | −219,465 | 120,467 | 62,681 | −153,422 | 2.952 |
| 78 | 16 | 200% | 90 | 9 | −207,887 | 111,574 | 82,955 | −167,085 | 2.965 |
| 79 | 16 | 300% | 90 | 9 | −170,474 | 78,244 | 81,146 | −157,054 | 2.987 |
| 80 | 16 | 600% | 90 | 9 | −87,415 | 6,717 | 23,889 | −101,510 | 3.019 |
| 81 | 16 | 100% | 180 | 9 | −244,729 | 131,676 | 46,028 | −157,316 | 2.948 |
| 82 | 16 | 150% | 180 | 9 | −253,840 | 143,931 | 69,507 | −171,758 | 2.972 |
| 83 | 16 | 200% | 180 | 9 | −241,828 | 135,549 | 90,919 | −187,446 | 2.996 |
| 84 | 16 | 300% | 180 | 9 | −196,154 | 95,267 | 82,398 | −171,295 | 3.030 |
| 85 | 16 | 600% | 180 | 9 | −96,966 | 6,783 | 10,746 | −94,286 | 3.065 |
| 86 | 16 | 100% | 270 | 9 | −256,214 | 138,256 | 46,950 | −161,878 | 2.953 |
| 87 | 16 | 150% | 270 | 9 | −266,095 | 152,759 | 71,169 | −177,989 | 2.982 |
| 88 | 16 | 200% | 270 | 9 | −252,978 | 143,904 | 92,368 | −194,389 | 3.011 |
| 89 | 16 | 300% | 270 | 9 | −201,986 | 99,444 | 79,672 | −174,951 | 3.047 |
| 90 | 16 | 600% | 270 | 9 | −95,226 | 4,505 | 9,348 | −89,021 | 3.067 |
| 91 | 16 | 100% | 90 | 6 | −251,105 | 147,502 | 40,160 | −137,825 | 2.938 |
| 92 | 16 | 150% | 90 | 6 | −273,190 | 162,499 | 83,129 | −171,886 | 2.952 |
| 93 | 16 | 200% | 90 | 6 | −273,476 | 164,715 | 111,938 | −194,431 | 2.970 |
| 94 | 16 | 300% | 90 | 6 | −251,477 | 155,247 | 124,992 | −192,402 | 3.006 |
| 95 | 16 | 600% | 90 | 6 | −162,002 | 81,068 | 88,583 | −151,100 | 3.088 |
| 96 | 16 | 100% | 180 | 6 | −283,509 | 167,993 | 42,501 | −150,443 | 2.946 |
| 97 | 16 | 150% | 180 | 6 | −316,957 | 196,512 | 93,727 | −194,425 | 2.973 |
| 98 | 16 | 200% | 180 | 6 | −323,773 | 207,903 | 130,101 | −225,006 | 3.008 |
| 99 | 16 | 300% | 180 | 6 | −301,656 | 198,082 | 143,440 | −225,237 | 3.079 |
| 100 | 16 | 600% | 180 | 6 | −183,073 | 96,386 | 81,281 | −150,422 | 3.207 |
| 101 | 16 | 100% | 270 | 6 | −295,569 | 176,229 | 43,169 | −155,136 | 2.950 |
| 102 | 16 | 150% | 270 | 6 | −333,596 | 210,303 | 97,581 | −202,698 | 2.985 |
| 103 | 16 | 200% | 270 | 6 | −342,534 | 223,527 | 136,763 | −236,122 | 3.028 |

TABLE 4-continued

Elastic Material Properties Analysis Results - Leg Length Tuned for 3.0 inches Displacement

| | | | | | Buckle Center | | Buckle Edge | | Free |
|---|---|---|---|---|---|---|---|---|---|
| Case | Pipe Dia (in) | Buckle Ht Pct. Wall | Circum. Ang. | l/h | ID Min. Axial (psi) | OD Max. Axial (psi) | ID Max. Axial (psi) | OD Min. Axial (psi) | Deflection (in) |
| 104 | 16 | 300% | 270 | 6 | −318,144 | 211,662 | 148,420 | −235,525 | 3.113 |
| 105 | 16 | 600% | 270 | 6 | −181,534 | 95,319 | 70,739 | −143,311 | 3.232 |
| 106 | 16 | 100% | 90 | 3 | −293,458 | 229,017 | 32,440 | −132,549 | 2.934 |
| 107 | 16 | 150% | 90 | 3 | −326,114 | 243,416 | 31,535 | −129,768 | 2.947 |
| 108 | 16 | 200% | 90 | 3 | −343,225 | 243,558 | 121,253 | −194,352 | 2.966 |
| 109 | 16 | 300% | 90 | 3 | −361,334 | 243,729 | 150,876 | −221,824 | 3.012 |
| 110 | 16 | 600% | 90 | 3 | −300,916 | 222,259 | 155,535 | −229,360 | 3.149 |
| 111 | 16 | 100% | 180 | 3 | −327,093 | 254,276 | 32,332 | −142,847 | 2.940 |
| 112 | 16 | 150% | 180 | 3 | −368,303 | 295,148 | 31,012 | −142,095 | 2.965 |
| 113 | 16 | 200% | 180 | 3 | −398,097 | 298,938 | 150,124 | −232,429 | 3.006 |
| 114 | 16 | 300% | 180 | 3 | −439,201 | 313,115 | 209,835 | −284,796 | 3.112 |
| 115 | 16 | 600% | 180 | 3 | −398,184 | 295,872 | 227,710 | −295,308 | 3.477 |
| 116 | 16 | 100% | 270 | 3 | −340,214 | 264,234 | 32,230 | −146,723 | 2.943 |
| 117 | 16 | 150% | 270 | 3 | −385,812 | 316,803 | 30,745 | −146,713 | 2.976 |
| 118 | 16 | 200% | 270 | 3 | −421,779 | 322,499 | 162,844 | −248,987 | 3.030 |
| 119 | 16 | 300% | 270 | 3 | −467,121 | 341,194 | 235,838 | −313,146 | 3.170 |
| 120 | 16 | 600% | 270 | 3 | −405,459 | 307,065 | 243,769 | −302,812 | 3.632 |

TABLE III-2

Elastic-Plastic Material Properties Analysis Results - Outward Wrinkles

| | | | | | Buckle Center | | | | Buckle Edge | |
|---|---|---|---|---|---|---|---|---|---|---|
| | | | | | ID Max. SEQV (psi) | | OD Max. SEQV (psi) | | ID Max. SEQV (psi) | |
| Case | Pipe Dia | Height % Wall | Circ. Ang. | l/h | Loaded | Unloaded | Loaded | Unloaded | Loaded | Unloaded |
| Swanson Creek | 12.75 | 500% | 270 | 3 | 79,997 | 79,880 | 79,740 | 79,881 | 67,373 | 67,520 |
| 1 | 16 | 150% | 120 | 12 | 61,102 | 61,313 | 56,675 | 24,182 | 45,384 | 19,429 |
| 2 | 16 | 300% | 120 | 12 | 57,847 | 56,433 | 56,078 | 32,744 | 41,919 | 12,466 |
| 3 | 16 | 150% | 150 | 12 | 61,918 | 62,105 | 57,070 | 22,732 | 42,640 | 20,952 |
| 4 | 16 | 300% | 150 | 12 | 58,360 | 58,360 | 56,644 | 29,571 | 41,722 | 14,453 |
| 5 | 16 | 150% | 180 | 12 | 62,953 | 63,161 | 57,635 | 21,491 | 38,581 | 23,109 |
| 6 | 16 | 300% | 180 | 12 | 59,067 | 59,090 | 57,000 | 25,341 | 41,285 | 15,329 |
| 7 | 16 | 150% | 120 | 9 | 63,993 | 64,288 | 58,820 | 26,885 | 48,313 | 33,164 |
| 8 | 16 | 300% | 120 | 9 | 60,274 | 60,450 | 57,261 | 35,620 | 45,535 | 22,917 |
| 9 | 16 | 150% | 150 | 9 | 65,190 | 65,507 | 59,649 | 29,406 | 48,873 | 37,765 |
| 10 | 16 | 300% | 150 | 9 | 61,258 | 61,473 | 57,705 | 32,097 | 45,197 | 23,432 |
| 11 | 16 | 150% | 180 | 9 | 66,887 | 67,219 | 60,612 | 32,091 | 49,805 | 39,967 |
| 12 | 16 | 300% | 180 | 9 | 62,428 | 62,623 | 56,522 | 28,112 | 43,675 | 26,680 |
| e2 | 16 | 400% | 180 | 9 | 60,301 | 60,396 | 57,862 | 29,963 | 44,901 | 23,185 |
| e2 | 16 | 500% | 180 | 9 | 68,642 | 56,940 | 57,230 | 35,236 | 45,352 | 17,829 |
| e1 | 16 | 150% | 270 | 9 | 70,683 | 71,010 | 62,778 | 36,261 | 52,455 | 45,228 |
| e1 | 16 | 300% | 270 | 9 | 65,032 | 65,274 | 60,470 | 25,590 | 44,616 | 26,772 |
| e3 | 16 | 150% | 180 | 7.5 | 69,912 | 70,284 | 63,658 | 44,959 | 58,722 | 45,888 |
| e3 | 16 | 300% | 180 | 7.5 | 65,063 | 65,411 | 60,267 | 40,755 | 47,346 | 34,011 |
| e3 | 16 | 400% | 180 | 7.5 | 62,716 | 62,859 | 59,088 | 33,587 | 45,338 | 27,348 |
| e3 | 16 | 500% | 180 | 7.5 | 61,021 | 61,072 | 58,404 | 36,160 | 45,475 | 26,320 |
| 13 | 16 | 150% | 120 | 6 | 69,354 | 69,692 | 65,196 | 52,897 | 59,228 | 39,254 |
| 14 | 16 | 300% | 120 | 6 | 64,969 | 65,415 | 60,528 | 53,950 | 54,017 | 41,492 |
| 15 | 16 | 150% | 150 | 6 | 71,347 | 71,695 | 66,648 | 56,385 | 60,094 | 42,851 |
| 16 | 16 | 300% | 150 | 6 | 66,626 | 67,115 | 61,774 | 59,268 | 53,988 | 45,187 |
| 17 | 16 | 150% | 180 | 6 | 74,207 | 74,551 | 68,626 | 59,584 | 61,284 | 46,200 |
| 18 | 16 | 300% | 180 | 6 | 69,108 | 69,646 | 63,459 | 63,378 | 55,040 | 45,693 |
| e1 | 16 | 150% | 270 | 6 | 79,981 | 79,787 | 73,253 | 61,698 | 63,199 | 50,809 |
| e1 | 16 | 300% | 270 | 6 | 75,059 | 75,627 | 67,689 | 67,764 | 56,524 | 48,707 |
| 19 | 12.75 | 150% | 120 | 12 | 61,187 | 61,372 | 56,811 | 25,083 | 45,651 | 22,127 |
| 20 | 12.75 | 300% | 120 | 12 | 57,677 | 51,999 | 56,029 | 32,139 | 44,423 | 13,321 |
| 21 | 12.75 | 150% | 150 | 12 | 61,964 | 62,131 | 57,151 | 22,701 | 45,083 | 22,855 |
| 22 | 12.75 | 300% | 150 | 12 | 58,162 | 55,356 | 56,632 | 29,281 | 44,266 | 15,040 |
| 23 | 12.75 | 150% | 180 | 12 | 62,907 | 63,097 | 57,690 | 20,762 | 40,770 | 23,501 |
| 24 | 12.75 | 300% | 180 | 12 | 58,855 | 58,380 | 58,976 | 25,944 | 44,915 | 16,768 |
| 25 | 12.75 | 150% | 120 | 9 | 64,111 | 64,393 | 58,407 | 23,677 | 46,975 | 29,732 |
| 26 | 12.75 | 300% | 120 | 9 | 60,110 | 60,234 | 57,342 | 35,954 | 45,424 | 22,116 |
| 27 | 12.75 | 150% | 150 | 9 | 65,280 | 65,588 | 59,096 | 25,645 | 46,180 | 34,747 |
| 28 | 12.75 | 300% | 150 | 9 | 61,069 | 61,232 | 57,744 | 32,323 | 45,250 | 24,792 |

TABLE III-2-continued

Elastic-Plastic Material Properties Analysis Results - Outward Wrinkles

| | | | | | | | | | |
|---|---|---|---|---|---|---|---|---|---|
| 29 | 12.75 | 150% | 1809 | 66,948 | 67,274 | 60,118 | 28,076 | 46,394 | 37,010 |
| 30 | 12.75 | 300% | 1809 | 62,155 | 62,308 | 58,451 | 27,059 | 45,238 | 26,817 |
| e2 | 12.75 | 400% | 1809 | 59,955 | 59,994 | 57,740 | 31,798 | 45,476 | 22,623 |
| e2 | 12.75 | 500% | 1809 | 58,170 | 51,882 | 66,995 | 35,284 | 45,483 | 16,779 |
| e1 | 12.75 | 150% | 2709 | 70,733 | 71,059 | 62,303 | 32,042 | 47,787 | 43,447 |
| e1 | 12.75 | 300% | 2709 | 64,639 | 64,838 | 60,235 | 25,356 | 45,248 | 28,116 |
| 31 | 12.75 | 150% | 1206 | 69,647 | 70,018 | 64,582 | 45,242 | 59,428 | 40,103 |
| 32 | 12.75 | 300% | 1206 | 64,877 | 65,285 | 60,017 | 46,793 | 53,350 | 38,340 |
| 33 | 12.75 | 150% | 1506 | 71,640 | 72,021 | 65,684 | 49,544 | 60,281 | 44,262 |
| 34 | 12.75 | 300% | 1506 | 66,527 | 66,980 | 61,369 | 50,545 | 52,857 | 44,135 |
| 35 | 12.75 | 150% | 1806 | 74,472 | 74,853 | 67,701 | 53,711 | 61,465 | 47,260 |
| 36 | 12.75 | 300% | 1806 | 69,021 | 69,603 | 63,041 | 57,612 | 53,367 | 45,427 |
| e1 | 12.75 | 150% | 2706 | 79,984 | 79,821 | 72,148 | 57,111 | 63,492 | 51,709 |
| e2 | 12.75 | 300% | 2706 | 75,072 | 75,551 | 67,256 | 66,413 | 55,194 | 46,853 |

| | Buckle Edge OD Max. SEQV (psi) | | Reversed Plastic Strain | | | | Free Deflection (in) | |
|---|---|---|---|---|---|---|---|---|
| | | | Buckle Center | | Buckle Edge | | | |
| Case | Loaded | Unloaded | ID | OD | ID | OD | Loaded | Unloaded |
| Swanson Creek | 69,030 | 69,520 | 0.0271 | 0.0158 | 0.0040 | 0.0074 | 9.352 | 7.240 |
| 1 | 57,208 | 40,609 | 0.0020 | 0 | 0 | 0 | 1.733 | 0.243 |
| 2 | 49,121 | 34,053 | 0.0001 | 0 | 0 | 0 | 1.733 | 0.232 |
| 3 | 57,392 | 42,340 | 0.0023 | 0 | 0 | 0 | 1.781 | 0.289 |
| 4 | 48,847 | 34,703 | 0.0002 | 0 | 0 | 0 | 1.773 | 0.269 |
| 5 | 57,648 | 44,016 | 0.0025 | 0 | 0 | 0 | 1.856 | 0.360 |
| 6 | 48,536 | 35,033 | 0.0004 | 0 | 0 | 0 | 1.835 | 0.327 |
| 7 | 57,915 | 44,527 | 0.0037 | 0 | 0 | 0 | 1.798 | 0.304 |
| 8 | 55,300 | 47,251 | 0.0023 | 0 | 0 | 0 | 1.898 | 0.377 |
| 9 | 58,284 | 47,011 | 0.0040 | 0 | 0 | 0 | 1.867 | 0.370 |
| 10 | 55,183 | 48,969 | 0.0026 | 0 | 0 | 0 | 1.991 | 0.463 |
| 11 | 58,784 | 49,634 | 0.0043 | 0 | 0 | 0 | 1.975 | 0.474 |
| 12 | 55,018 | 50,937 | 0.0029 | 0 | 0 | 0 | 2.138 | 0.603 |
| e2 | 49,480 | 40,282 | 0.0013 | 0 | 0 | 0 | 2.059 | 0.516 |
| e2 | 46,589 | 24,694 | 0.0001 | 0 | 0 | 0 | 1.961 | 0.416 |
| e1 | 60,117 | 52,953 | 0.0044 | 0 | 0.0002 | 0 | 2.240 | 0.730 |
| e1 | 54,805 | 53,664 | 0.0031 | 0 | 0 | 0 | 2.520 | 0.973 |
| e3 | 62,041 | 60,177 | 0.0052 | 0 | 0.0001 | 0 | 2.033 | 0.529 |
| e3 | 57,064 | 57,086 | 0.0046 | 0 | 0 | 0.0008 | 2.392 | 0.836 |
| e3 | 50,057 | 47,643 | 0.0030 | 0 | 0 | 0 | 2.357 | 0.786 |
| e3 | 51,992 | 47,401 | 0.0015 | 0 | 0 | 0 | 2.256 | 0.677 |
| 13 | 61,540 | 60,811 | 0.0055 | 0 | 0 | 0 | 1.855 | 0.360 |
| 14 | 58,189 | 58,008 | 0.0056 | 0 | 0 | 0.0012 | 2.194 | 0.644 |
| 15 | 62,344 | 62,291 | 0.0058 | 0 | 0 | 0.0002 | 1.942 | 0.442 |
| 16 | 58,364 | 58,118 | 0.0063 | 0 | 0.0003 | 0.0018 | 2.395 | 0.830 |
| 17 | 63,516 | 63,521 | 0.0060 | 0 | 0 | 0.0004 | 2.078 | 0.573 |
| 18 | 58,725 | 58,494 | 0.0070 | 0.0005 | 0.0008 | 0.0023 | 2.732 | 1.150 |
| e1 | 66,354 | 66,291 | 0.0060 | 0 | 0.0003 | 0.0005 | 2.414 | 0.900 |
| e1 | 59,345 | 59,256 | 0.0077 | 0.0012 | 0.0013 | 0.0030 | 3.696 | 2.084 |
| 19 | 57,466 | 42,260 | 0.0018 | 0 | 0 | 0 | 1.778 | 0.292 |
| 20 | 46,904 | 26,504 | 0 | 0 | 0 | 0 | 1.760 | 0.266 |
| 21 | 57,591 | 44,027 | 0.0021 | 0 | 0 | 0 | 1.825 | 0.337 |
| 22 | 46,647 | 27,258 | 0 | 0 | 0 | 0 | 1.794 | 0.297 |
| 23 | 57,802 | 45,669 | 0.0023 | 0 | 0 | 0 | 1.898 | 0.407 |
| 24 | 46,357 | 27,760 | 0.0001 | 0 | 0 | 0 | 1.844 | 0.344 |
| 25 | 57,768 | 44,993 | 0.0035 | 0 | 0 | 0 | 1.853 | 0.364 |
| 26 | 49,257 | 38,921 | 0.0018 | 0 | 0 | 0 | 1.931 | 0.418 |
| 27 | 58,023 | 47,536 | 0.0038 | 0 | 0 | 0 | 1.925 | 0.432 |
| 28 | 46,950 | 40,081 | 0.0021 | 0 | 0 | 0 | 2.015 | 0.496 |
| 29 | 58,495 | 50,249 | 0.0041 | 0 | 0 | 0 | 2.037 | 0.539 |
| 30 | 48,591 | 41,594 | 0.0024 | 0 | 0 | 0 | 2.148 | 0.622 |
| e2 | 47,052 | 30,82 | 0.0008 | 0 | 0 | 0 | 2.051 | 0.521 |
| e2 | 48,606 | 32,138 | 0 | 0 | 0 | 0 | 1.948 | 0.416 |
| e1 | 59,634 | 53,533 | 0.0043 | 0 | 0 | 0 | 2.311 | 0.807 |
| e1 | 47,687 | 42,910 | 0.0025 | 0 | 0 | 0 | 2.494 | 0.959 |
| 31 | 61,929 | 60,823 | 0.0054 | 0 | 0 | 0 | 1.924 | 0.431 |
| 32 | 58,426 | 58,441 | 0.0051 | 0 | 0 | 0.0012 | 2.255 | 0.713 |
| 33 | 62,780 | 62,744 | 0.0057 | 0 | 0 | 0.0002 | 2.018 | 0.521 |
| 34 | 58,643 | 58,462 | 0.0058 | 0 | 0.0001 | 0.0018 | 2.454 | 0.899 |
| 35 | 64,023 | 63,997 | 0.0060 | 0 | 0.0001 | 0.0004 | 2.164 | 0.662 |
| 36 | 58,707 | 58,655 | 0.0062 | 0 | 0.0005 | 0.0024 | 2.786 | 1.215 |
| e1 | 66,958 | 66,920 | 0.0061 | 0 | 0.0005 | 0.0005 | 2.528 | 1.017 |

TABLE III-2-continued

Elastic-Plastic Material Properties Analysis Results - Outward Wrinkles

| e2 | 59,415 | 59,347 | 0.0064 | 0.0001 | 0.0011 | 0.0030 | 3.738 | 2.141 |

TABLE III-3

Elastic-Plastic Material Properties Analysis Results - Inward Wrinkles

| Case | Pipe Dia | Height % Wall | Circ. Ang. | I/h | Buckle Center ID Max. SEQV Loaded | Buckle Center ID Max. SEQV Unloaded | Buckle Center OD Max. SEQV Loaded | Buckle Center OD Max. SEQV Unloaded | Buckle Edge ID Max. SEQV Loaded | Buckle Edge ID Max. SEQV Unloaded |
| --- | --- | --- | --- | --- | --- | --- | --- | --- | --- | --- |
| 1 | 16 | -150% | 1202 | | 57,889 | 34,719 | 63,576 | 63,737 | 57,487 | 48,758 |
| 2 | 16 | -300% | 1202 | | 57,089 | 44,577 | 59,337 | 58,446 | 55,331 | 36,871 |
| 3 | 16 | -150% | 1502 | | 57,697 | 34,324 | 63,817 | 63,997 | 57,696 | 51,879 |
| 4 | 16 | -300% | 1502 | | 56,688 | 43,227 | 59.196 | 58,739 | 55,880 | 37,294 |
| 5 | 16 | -150% | 1802 | | 57,342 | 32,884 | 64,270 | 64,465 | 57,997 | 53,973 |
| 6 | 16 | -300% | 1802 | | 55,135 | 37,911 | 59,077 | 58,773 | 56,304 | 37,323 |
| 7 | 16 | -150% | 1209 | | 62,762 | 44,784 | 67,319 | 67,634 | 58,001 | 51,557 |
| 8 | 16 | -300% | 1209 | | 60,068 | 49,058 | 63,018 | 63,114 | 57,827 | 57,258 |
| 9 | 16 | -150% | 1509 | | 62,631 | 47,976 | 67,941 | 68,280 | 58,326 | 53,864 |
| 10 | 16 | -300% | 1509 | | 60,027 | 46,542 | 63,301 | 63,342 | 58,071 | 57,448 |
| 11 | 16 | -150% | 1809 | | 62,607 | 50,980 | 68,791 | 69,151 | 58,744 | 56,674 |
| 12 | 16 | -300% | 1809 | | 59,841 | 47,641 | 63,625 | 63,746 | 58,486 | 57,982 |
| e1 | 16 | -150% | 2709 | | 62,816 | 56,129 | 70,667 | 71,043 | 59,699 | 59,562 |
| e1 | 16 | -300% | 2709 | | 59,269 | 48,248 | 64,274 | 64,459 | 58,955 | 58,725 |
| e4 | 16 | -150% | 1807.5 | | 66,608 | 60,394 | 71,960 | 72,397 | 61,477 | 60,325 |
| e4 | 16 | -300% | 1807.5 | | 62,843 | 62,984 | 68,696 | 66,962 | 60,023 | 60,026 |
| 13 | 16 | -150% | 1206 | | 70,133 | 64,068 | 73,505 | 73,930 | 60,924 | 52,382 |
| 14 | 16 | -300% | 1206 | | 64,471 | 64,116 | 69,313 | 69,756 | 60,291 | 60,454 |
| 15 | 16 | -150% | 1506 | | 70,913 | 66,512 | 74,758 | 75,177 | 61,965 | 55,193 |
| 16 | 16 | -300% | 1506 | | 65,634 | 65,832 | 70,057 | 70,543 | 61,122 | 61,167 |
| 17 | 16 | -150% | 1806 | | 72,014 | 68,487 | 76,527 | 76,937 | 63,266 | 58,360 |
| 18 | 16 | -300% | 1806 | | 66,651 | 66,921 | 71,286 | 71,884 | 61,720 | 61,853 |
| e1 | 16 | -150% | 2706 | | 74,820 | 71,865 | 79,998 | 79,861 | 65,749 | 63,522 |
| e1 | 16 | -300% | 2706 | | 68,768 | 69,151 | 75,009 | 75,646 | 62,759 | 62,944 |
| 19 | 12.75 | -150% | 1202 | | 57,858 | 40,558 | 63,966 | 64,091 | 57,755 | 51,800 |
| 20 | 12.75 | -300% | 1202 | | 57,225 | 44,430 | 59,636 | 58,632 | 51,437 | 26,353 |
| 21 | 12.75 | -150% | 1502 | | 57,490 | 37,756 | 64,234 | 64,382 | 57,988 | 54,380 |
| 22 | 12.75 | -300% | 1502 | | 56,674 | 44,717 | 59,338 | 58,404 | 51,934 | 26,791 |
| 23 | 12.75 | -150% | 1802 | | 57,272 | 36,408 | 64,509 | 64,677 | 58,331 | 56,938 |
| 24 | 12.75 | -300% | 1802 | | 53,944 | 42,143 | 58,976 | 58,057 | 52,287 | 27,302 |
| 25 | 12.75 | -150% | 1209 | | 62,599 | 41,438 | 68,054 | 68,333 | 58,162 | 53,508 |
| 26 | 12.75 | -300% | 1209 | | 60,231 | 49,494 | 63,267 | 63,350 | 56,507 | 42,319 |
| 27 | 12.75 | -150% | 1509 | | 62,313 | 44,262 | 68,634 | 68,942 | 58,500 | 55,752 |
| 28 | 12.75 | -300% | 1509 | | 60,090 | 50,157 | 63,519 | 63,516 | 56,662 | 43,060 |
| 29 | 12.75 | -150% | 1809 | | 62,081 | 47,612 | 69,289 | 69,629 | 58,899 | 57,678 |
| 30 | 12.75 | -300% | 1809 | | 59,688 | 43,228 | 63,783 | 63,863 | 56,848 | 42,499 |
| e1 | 12.75 | -150% | 2709 | | 61,985 | 52,494 | 70,930 | 71,297 | 59,666 | 59,550 |
| e1 | 12.75 | -300% | 2709 | | 58,821 | 38,580 | 64,126 | 64,275 | 56,983 | 42,285 |
| 31 | 12.75 | -150% | 1206 | | 70,344 | 59,782 | 74,783 | 75,215 | 61,264 | 58,500 |
| 32 | 12.75 | -300% | 1206 | | 64,620 | 64,212 | 70,191 | 70,613 | 60,711 | 60,878 |
| 33 | 12.75 | -150% | 1506 | | 70,815 | 61,843 | 75,769 | 76,217 | 62,253 | 61,297 |
| 34 | 12.75 | -300% | 1506 | | 65,817 | 65,075 | 70,884 | 71,321 | 61,733 | 61,791 |
| 35 | 12.75 | -150% | 1806 | | 71,600 | 64,755 | 77,334 | 77,788 | 63,477 | 63,540 |
| 36 | 12.75 | -300% | 1806 | | 68,808 | 88,890 | 71,895 | 72,328 | 62,377 | 62,498 |
| e1 | 12.75 | -150% | 2706 | | 73,984 | 68,164 | 79,998 | 79,933 | 65,838 | 65,920 |
| e1 | 12.75 | -300% | 2706 | | 68,373 | 68,548 | 75,292 | 75,834 | 63,524 | 63,651 |

| Case | Buckle Edge OD Max. SEQV Loaded | Buckle Edge OD Max. SEQV Unloaded | Reversed Plastic Strain Buckle Center ID | Reversed Plastic Strain Buckle Center OD | Reversed Plastic Strain Buckle Edge ID | Reversed Plastic Strain Buckle Edge OD | Free Deflection Loaded | Free Deflection Unloaded |
| --- | --- | --- | --- | --- | --- | --- | --- | --- |
| 1 | 51,462 | 39,748 | 0 | 0.0020 | 0 | 0 | 1.745 | 0.249 |
| 2 | 53,874 | 17,102 | 0.0003 | 0.0010 | 0 | 0 | 1.894 | 0.362 |
| 3 | 51,885 | 40,401 | 0 | 0.0022 | 0 | 0 | 1.770 | 0.271 |
| 4 | 54,613 | 19,863 | 0.0001 | 0.0007 | 0 | 0 | 1.908 | 0.374 |
| 5 | 52,214 | 38,649 | 0 | 0.0023 | 0 | 0 | 1.807 | 0.306 |
| 6 | 55,153 | 23,717 | 0 | 0.0004 | 0 | 0 | 1.925 | 0.388 |
| 7 | 52,066 | 41,991 | 0 | 0.0038 | 0 | 0 | 1.795 | 0.295 |
| 8 | 56,744 | 31,407 | 0 | 0.0033 | 0.0002 | 0 | 2.049 | 0.500 |
| 9 | 52,131 | 40,695 | 0 | 0.0040 | 0 | 0 | 1.835 | 0.331 |

TABLE III-3-continued

Elastic-Plastic Material Properties Analysis Results - Inward Wrinkles

| | | | | | | | | |
|---|---|---|---|---|---|---|---|---|
| 10 | 56,831 | 31,188 | 0 | 0.0032 | 0.0003 | 0 | 2.102 | 0.545 |
| 11 | 52,001 | 39,094 | 0 | 0.0043 | 0 | 0 | 1.893 | 0.385 |
| 12 | 56,894 | 31,476 | 0 | 0.0031 | 0.0004 | 0 | 2.175 | 0.611 |
| e1 | 52,511 | 37,501 | 0 | 0.0045 | 0.0001 | 0 | 2.033 | 0.519 |
| e1 | 57,015 | 25,976 | 0 | 0.0029 | 0.0005 | 0 | 2.350 | 0.776 |
| e4 | 55,826 | 40,333 | 0 | 0.0052 | 0 | 0 | 1.938 | 0.428 |
| e4 | 57,205 | 33,713 | 0.0004 | 0.0049 | 0.0012 | 0 | 2.379 | 0.794 |
| 13 | 57,960 | 43,668 | 0 | 0.0053 | 0 | 0.0001 | 1.841 | 0.340 |
| 14 | 56,973 | 42,857 | 0 | 0.0062 | 0.0018 | 0 | 2.289 | 0.713 |
| 15 | 58,739 | 41,765 | 0.0001 | 0.0056 | 0 | 0 | 1.897 | 0.391 |
| 16 | 57,343 | 39,977 | 0.0007 | 0.0070 | 0.0021 | 0 | 2.431 | 0.838 |
| 17 | 59,644 | 38,461 | 0.0007 | 0.0062 | 0 | 0 | 1.981 | 0.469 |
| 18 | 57,274 | 36,018 | 0.0023 | 0.0079 | 0.0024 | 0 | 2.653 | 1.040 |
| e1 | 61,186 | 36,442 | 0.0005 | 0.0060 | 0.0001 | 0 | 2.184 | 0.663 |
| e1 | 57,800 | 36,081 | 0.0038 | 0.0086 | 0.0029 | 0 | 3.264 | 1.620 |
| 19 | 53,106 | 38,616 | 0 | 0.0018 | 0 | 0 | 1.809 | 0.316 |
| 20 | 53,349 | 21,185 | 0.0004 | 0.0009 | 0 | 0 | 1.978 | 0.449 |
| 21 | 53,700 | 40,291 | 0 | 0.0020 | 0 | 0 | 1.834 | 0.338 |
| 22 | 54,097 | 22,471 | 0.0002 | 0.0006 | 0 | 0 | 1.989 | 0.457 |
| 23 | 54,123 | 38,278 | 0 | 0.0021 | 0 | 0 | 1.868 | 0.370 |
| 24 | 54,785 | 20,211 | 0 | 0.0003 | 0 | 0 | 1.996 | 0.463 |
| 25 | 54,205 | 41,851 | 0 | 0.0036 | 0 | 0 | 1.868 | 0.372 |
| 26 | 56,727 | 25,970 | 0.0006 | 0.0032 | 0 | 0 | 2.150 | 0.605 |
| 27 | 54,328 | 40,788 | 0 | 0.0038 | 0 | 0 | 1.909 | 0.409 |
| 28 | 56,895 | 25,991 | 0 | 0.0030 | 0 | 0 | 2.200 | 0.648 |
| 29 | 54,139 | 39,127 | 0 | 0.0041 | 0.0001 | 0 | 1.968 | 0.464 |
| 30 | 57,008 | 23,718 | 0 | 0.0028 | 0 | 0 | 2.260 | 0.702 |
| e1 | 54,523 | 37,608 | 0 | 0.0044 | 0.0003 | 0 | 2.109 | 0.598 |
| e1 | 57,189 | 24,012 | 0 | 0.0025 | 0 | 0 | 2.400 | 0.834 |
| 31 | 57,813 | 46,127 | 0 | 0.0054 | 0 | 0.0001 | 1.922 | 0.424 |
| 32 | 57,416 | 41,891 | 0 | 0.0061 | 0.0019 | 0 | 2.417 | 0.846 |
| 33 | 58,218 | 45,058 | 0 | 0.0058 | 0 | 0 | 1.982 | 0.479 |
| 34 | 57,892 | 41,023 | 0 | 0.0064 | 0.0021 | 0 | 2.564 | 0.978 |
| 35 | 58,738 | 41,079 | 0.0001 | 0.0059 | 0.0001 | 0 | 2.071 | 0.561 |
| 36 | 57,826 | 37,732 | 0.0006 | 0.0068 | 0.0024 | 0 | 2.782 | 1.177 |
| e1 | 59,800 | 35,788 | 0.0002 | 0.0060 | 0.0005 | 0 | 2.286 | 0.767 |
| e1 | 58,191 | 34,224 | 0.0021 | 0.0072 | 0.0028 | 0 | 3.376 | 1.742 |

TABLE III-4

ASME Code Fatigue Analysis Results

| Case | Pipe Dia | Buckle Ht Pct. Wall | Circum. Ang. | l/h | Max. Alt. Stress Int. | Code Fatigue Life |
|---|---|---|---|---|---|---|
| Swanson Creek | 12.75 | 600% | 270 | 3 | 216.66 | 90 |
| 1 | 16 | 150% | 180 | 12 | 110.07 | 450 |
| 2 | 16 | 300% | 180 | 12 | 89.34 | 800 |
| 3 | 16 | 450% | 180 | 12 | 68.22 | 1,690 |
| 4 | 16 | 600% | 180 | 12 | 56.52 | 2,970 |
| 5 | 16 | 150% | 180 | 9 | 125.34 | 330 |
| 6 | 16 | 300% | 180 | 9 | 118.05 | 380 |
| 7 | 16 | 450% | 180 | 9 | 92.91 | 720 |
| 8 | 16 | 600% | 180 | 9 | 73.55 | 1,380 |
| 9 | 16 | 150% | 180 | 7.5 | 137.22 | 270 |
| 10 | 16 | 300% | 180 | 7.5 | 135.05 | 280 |
| 11 | 16 | 450% | 180 | 7.5 | 112.62 | 420 |
| 12 | 16 | 600% | 180 | 7.5 | 90.41 | 780 |
| 13 | 16 | 150% | 180 | 6 | 151.21 | 210 |
| 14 | 16 | 300% | 180 | 6 | 153.31 | 210 |
| 15 | 16 | 450% | 180 | 6 | 138.92 | 260 |
| 16 | 16 | 600% | 180 | 6 | 116.34 | 390 |
| 17 | 12.75 | 150% | 180 | 12 | 109.32 | 450 |
| 18 | 12.75 | 300% | 180 | 12 | 85.82 | 910 |
| 19 | 12.75 | 450% | 180 | 12 | 65.82 | 1,860 |
| 20 | 12.75 | 600% | 180 | 12 | 55.02 | 3,240 |
| 21 | 12.75 | 150% | 180 | 9 | 125.52 | 330 |
| 22 | 12.75 | 300% | 180 | 9 | 113.29 | 420 |
| 23 | 12.75 | 450% | 180 | 9 | 87.62 | 850 |
| 24 | 12.75 | 600% | 180 | 9 | 71.20 | 1,510 |
| 25 | 12.75 | 150% | 180 | 7.5 | 135.07 | 280 |
| 26 | 12.75 | 300% | 180 | 7.5 | 131.12 | 300 |
| 27 | 12.75 | 450% | 180 | 7.5 | 106.42 | 480 |
| 28 | 12.75 | 600% | 180 | 7.5 | 84.52 | 950 |
| 29 | 12.75 | 150% | 180 | 6 | 149.59 | 220 |
| 30 | 12.75 | 300% | 180 | 6 | 149.93 | 220 |
| 31 | 12.75 | 450% | 180 | 6 | 131.87 | 290 |
| 32 | 12.75 | 600% | 180 | 6 | 108.02 | 470 |
| 33 | 16 | -150% | 180 | 12 | 123.77 | 340 |
| 34 | 16 | -300% | 180 | 12 | 93.31 | 710 |
| 35 | 16 | -450% | 180 | 12 | 78.71 | 1,150 |
| 36 | 16 | -600% | 180 | 12 | 73.81 | 1,370 |
| 37 | 16 | -150% | 180 | 9 | 147.90 | 220 |
| 38 | 16 | -300% | 180 | 9 | 125.20 | 330 |
| 39 | 16 | -450% | 180 | 9 | 100.24 | 570 |
| 40 | 16 | -600% | 180 | 9 | 89.51 | 800 |
| 41 | 16 | -150% | 180 | 7.5 | 161.28 | 180 |
| 42 | 16 | -300% | 180 | 7.5 | 148.30 | 220 |
| 43 | 16 | -450% | 180 | 7.5 | 119.70 | 370 |
| 44 | 16 | -600% | 180 | 7.5 | 102.88 | 530 |
| 45 | 16 | -150% | 180 | 6 | 175.18 | 150 |
| 46 | 16 | -300% | 180 | 6 | 176.59 | 140 |
| 47 | 16 | -450% | 180 | 6 | 149.26 | 220 |
| 48 | 16 | -600% | 180 | 6 | 126.46 | 320 |
| 49 | 12.75 | -150% | 180 | 12 | 122.33 | 350 |
| 50 | 12.75 | -300% | 180 | 12 | 91.78 | 740 |
| 51 | 12.75 | -450% | 180 | 12 | 79.85 | 1,110 |
| 52 | 12.75 | -600% | 180 | 12 | 77.06 | 1,220 |

TABLE III-4-continued

ASME Code Fatigue Analysis Results

| Case | Pipe Dia | Buckle Ht Pct. Wall | Circum. Ang. | l/h | Max. Alt. Stress Int. | Code Fatigue Life |
|---|---|---|---|---|---|---|
| 53 | 12.75 | −150% | 180 | 9 | 147.36 | 230 |
| 54 | 12.75 | −300% | 180 | 9 | 122.19 | 350 |
| 55 | 12.75 | −450% | 180 | 9 | 98.82 | 600 |
| 56 | 12.75 | −600% | 180 | 9 | 92.12 | 740 |
| 57 | 12.75 | −150% | 180 | 7.5 | 161.42 | 180 |
| 58 | 12.75 | −300% | 180 | 7.5 | 144.75 | 230 |
| 59 | 12.75 | −450% | 180 | 7.5 | 117.02 | 390 |
| 60 | 12.75 | −600% | 180 | 7.5 | 103.77 | 520 |
| 61 | 12.75 | −150% | 180 | 6 | 175.81 | 150 |
| 62 | 12.75 | −300% | 180 | 6 | 173.09 | 150 |
| 63 | 12.75 | −450% | 180 | 6 | 145.61 | 230 |
| 64 | 12.75 | −600% | 180 | 6 | 127.01 | 320 |

What is claimed is:

1. A method of pipeline inspection comprising the following steps:
   (a) running an ultrasonic testing inspection pig in a length of pipeline, the pipeline having a wall thickness;
   (b) gathering ultrasonic test data from the inspection pig;
   (c) correlating the ultrasonic test data gathered from the inspection pig to actual anomaly characteristics of the pipeline; and
   (d) determining the acceptability without repair of pipeline anomalies in pipe bends through a series of finite element models for varying anomaly geometries.

2. The method of pipeline inspection according to claim 1, further comprising the step of identifying locations along the pipeline that warrant remedial action from the step (c) of correlating the ultrasonic test data gathered from the inspection pig to actual anomaly characteristics of the pipeline.

3. A method of pipeline inspection comprising the following steps:
   (a) running an ultrasonic testing inspection pig in a length of pipeline, the pipeline having a wall thickness;
   (b) gathering ultrasonic test data from the inspection pig, identifying locations along the pipeline that warrant remedial action by identifying those locations where an anomaly has a surface waveform with both an inside and outside displacement component, the surface waveform height being greater than approximately 1.5 times the wall thickness of the pipeline location;
   (c) correlating the ultrasonic test data gathered from the inspection pig to actual anomaly characteristics of the pipeline.

4. The method of pipeline inspection according to claim 3, wherein the anomaly further has a ratio of surface waveform length/surface waveform height of less than approximately 12.

5. The method of pipeline inspection according to claim 3, wherein the anomaly further has a ratio of surface waveform length/surface waveform height of less than approximately 7.5.

6. The method of pipeline inspection according to claim 1, further comprising the step of identifying locations along the pipeline that warrant remedial action from the step (c) of correlating the ultrasonic test data gathered from the inspection pig to actual anomaly characteristics of the pipeline and, wherein the step of identifying locations along the pipeline that warrant remedial action identifies those locations where an anomaly has a circumferential extent greater than approximately 135°.

7. A method of pipeline inspection comprising the following steps:
   (a) running an ultrasonic testing inspection pig in a length of pipeline, the pipeline having a wall thickness;
   (b) gathering ultrasonic test data from the inspection pig;
   (c) correlating the ultrasonic test data gathered from the inspection pig to actual anomaly characteristics of the pipeline, wherein the step of correlating the ultrasonic test data gathered from the inspection pig to actual anomaly characteristics of the pipeline comprises the substeps of:
      (i) sorting the ultrasonic test data in a manner that categorizes physical deformation features into six (6) distinct pattern types (U, A, B, C, D and E) based on the geometric shape of the data signal;
      (ii) sequencing by seriousness of the pattern type ranked from U to E; and
      (iii) sub-sorting the data by degree of signal intensity from the most intense to the least intense (0, 1, 2, and 3).

8. A method of pipeline inspection comprising the following steps:
   (a) running an ultrasonic testing inspection pig in a length of pipeline, the pipeline having a wall thickness;
   (b) gathering ultrasonic test data from the inspection pig;
   (c) determining the acceptability without repair of pipeline anomalies in pipe bends through a series of finite element models for varying anomaly geometries using both elastic and elastic-plastic material properties; and
   (d) repairing pipeline anomalies uncovered by the ultrasonic test data that are not acceptable without repair as determined by step (c).

9. The method of pipeline inspection according to claim 8, wherein the step of determining the acceptability without repair of pipeline anomalies in pipe bends comprises the substeps of:
   (i) analyzing through finite element analyses the anomalies in the pipe bends;
   (ii) modeling the anomalies to be a residual-stress free discontinuity on the pipe bend intrados;
   (iii) analyzing aspect ratios of the anomalies, treating the height of the anomaly as an independent variable;
   (iv) analyzing circumferential extents of the anomalies;
   (v) analyzing the effects of soil restraint; and
   (vi) utilizing boundary conditions and loading properties.

* * * * *